United States Patent
Shinobu et al.

(10) Patent No.: US 9,086,338 B2
(45) Date of Patent: Jul. 21, 2015

(54) SENSING DEVICE

(75) Inventors: Wakako Shinobu, Sayama (JP); Hiroyuki Kukita, Sayama (JP); Tomoya Yorita, Sayama (JP); Shunichi Wakamatsu, Sayama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 940 days.

(21) Appl. No.: 13/134,866

(22) Filed: Jun. 20, 2011

(65) Prior Publication Data

US 2011/0316522 A1  Dec. 29, 2011

(30) Foreign Application Priority Data

Jun. 25, 2010  (JP) .................. 2010-144757
Jun. 30, 2010  (JP) .................. 2010-150215
Jun. 30, 2010  (JP) .................. 2010-150224

(51) Int. Cl.
  *G01N 5/02*  (2006.01)
(52) U.S. Cl.
  CPC ........................ *G01N 5/02* (2013.01)
(58) Field of Classification Search
  CPC ....... G01N 5/02; G01N 29/02; G01N 29/036; G01N 29/222; G01N 2291/0256
  USPC .................. 73/61.45, 61.49, 61.79, 64.53
  See application file for complete search history.

(56) References Cited

U.S. PATENT DOCUMENTS

| | | | |
|---|---|---|---|
| 5,892,143 A | 4/1999 | Namerikawa et al. | |
| 6,047,590 A | 4/2000 | Namerikawa et al. | |
| 6,490,911 B1 | 12/2002 | Namerikawa et al. | |
| 7,055,377 B2* | 6/2006 | Paul et al. | 73/54.41 |
| 7,204,139 B2 | 4/2007 | Takayama | |
| 8,176,772 B2 | 5/2012 | Wakamatsu | |
| 8,176,773 B2 | 5/2012 | Yamakawa et al. | |
| 8,230,724 B2* | 7/2012 | Gehring | 73/61.49 |
| 2003/0194709 A1 | 10/2003 | Yang | |
| 2005/0229696 A1 | 10/2005 | Takayama | |
| 2006/0141608 A1 | 6/2006 | Aastrup et al. | |
| 2009/0071847 A1 | 3/2009 | Edelbrock et al. | |
| 2009/0288488 A1 | 11/2009 | Yamakawa et al. | |
| 2010/0236331 A1 | 9/2010 | Wakamatsu | |

(Continued)

FOREIGN PATENT DOCUMENTS

| | | |
|---|---|---|
| JP | 58-092908 | 6/1983 |
| JP | 10-038788 | 2/1998 |

(Continued)

*Primary Examiner* — Daniel S Larkin
(74) *Attorney, Agent, or Firm* — Jordan and Hamburg LLP

(57) ABSTRACT

To provide a sensing device that holds a piezoelectric sensor and a channel forming member placed on the sensor in a closely contacted state while maintaining a shape of space of a passage space formed inside the device. In a sensing device 1100 that senses a substance to be sensed based on a variation in an oscillation frequency caused by an absorption of the substance to be sensed in an absorption layer provided on a piezoelectric resonator 1720 of a piezoelectric sensor 1700, a holding member 1600 holds the piezoelectric sensor 1700 and a channel forming member 1730 that forms a passage space through which a sample fluid passes on an upper surface side of the sensor, in a vertically stacked state. A cover member 1510 is placed on the channel forming member 1730, and a pressing part 1350 which is raised/lowered by a first raising/lowering mechanism 1300 presses the cover member 1510 placed on the channel forming member 1730 downward with a previously set force.

7 Claims, 34 Drawing Sheets

(56) References Cited

U.S. PATENT DOCUMENTS

| | | | |
|---|---|---|---|
| 2010/0313636 A1* | 12/2010 | Wakamatsu et al. | 73/64.53 |
| 2010/0329928 A1* | 12/2010 | Yorita et al. | 422/68.1 |
| 2010/0329932 A1* | 12/2010 | Yorita et al. | 422/82.01 |
| 2011/0064614 A1 | 3/2011 | Watanabe et al. | |

FOREIGN PATENT DOCUMENTS

| | | |
|---|---|---|
| JP | 11-183479 | 7/1999 |
| JP | 2000-258324 | 9/2000 |
| JP | 2000-283905 | 10/2000 |
| JP | 2003-307481 | 10/2003 |
| JP | 2004-279150 | 10/2004 |
| JP | 2004/113903 | 12/2004 |
| JP | 2005-522219 | 7/2005 |
| JP | 2006-033195 | 2/2006 |
| JP | 2006-510901 | 3/2006 |
| JP | 2006-194867 | 7/2006 |
| JP | 2006-220606 | 8/2006 |
| JP | 2006-250926 | 9/2006 |
| JP | 2007-040717 | 2/2007 |
| JP | 2007-108170 | 4/2007 |
| JP | 2007-521498 | 8/2007 |
| JP | 2007-327931 | 12/2007 |
| JP | 2008-058086 | 3/2008 |
| JP | 2008-102118 | 5/2008 |
| JP | 2009-008690 | 1/2009 |
| JP | 2009-213965 | 9/2009 |
| JP | 2009-536734 | 10/2009 |
| JP | 2010-002413 | 1/2010 |
| JP | 2010-004388 | 1/2010 |
| JP | 2011-27716 * | 2/2011 |
| JP | 2011-27717 * | 2/2011 |
| WO | WO-2004/057319 | 7/2004 |

* cited by examiner

AREA IMMERSED IN LIQUID  42  42  5

55A  52  55B 53  54

44

SENSING DEVICE

BACKGROUND OF THE INVENTION

1. Field of the Invention

The present invention relates to a sensing device for sensing a substance to be sensed contained in a sample solution based on an oscillation frequency of a piezoelectric resonator such as a quartz-crystal resonator.

2. Description of the Related Art

As a sensing device for sensing and measuring a trace substance contained in a sample solution, there has been known one which uses a quartz-crystal sensor being a piezoelectric sensor. As this type of sensing device, one that detects a substance to be sensed while letting a sample solution flow, as disclosed in Patent Document 1, has been known. Meanwhile, as a quartz-crystal sensor, there has been known a quartz-crystal sensor of twin sensor type capable of reducing an influence of an external factor of measurement environment such as a temperature, for instance (Patent Document 2). In this quartz-crystal sensor, an oscillation area for measurement and an oscillation area for reference are formed on a quartz-crystal piece, and on a front surface of the oscillation area for measurement, there is formed an absorption layer formed of a biological substance or the like. Accordingly, since only the oscillation area for measurement is affected by a mass change caused by an absorption of a substance to be sensed, by subtracting an oscillation frequency taken out from the oscillation area for reference from an oscillation frequency taken out from the oscillation area for measurement, it is possible to obtain a highly accurate measured result from which the external factor is removed.

Here, the applicant of the present application has been studying a method of reducing a height of a reaction channel (distance from a front surface of a quartz-crystal resonator and an opposing surface within a case body), as an example of a method of performing measurement of trace substance with higher sensitivity and higher accuracy. For example, even if the height of the reaction channel corresponds to a small size of 1 mm, a ratio in which an antigen reacts with an antibody in a liquid flow on the opposing surface side is smaller than a ratio in which an antigen reacts with an antibody in a liquid flow on the quartz-crystal resonator side. For this reason, a ratio of a substance to be sensed which is absorbed in an absorption layer, out of the substance to be sensed contained in a supplied sample solution is small, and thus it cannot be said that it is advantageous in terms of both sensitivity and accuracy.

Accordingly, it can be considered that by setting the distance between the front surface of the quartz-crystal sensor and the opposing surface, namely, the height of the reaction channel to 0.2 mm or less, for example, the ratio of sample solution which is brought into contact with the absorption layer of a quartz-crystal piece or flows in the vicinity of the absorption layer, out of the supplied sample solution, is increased. By setting as above, an amount of substance to be sensed contained in the sample solution that is absorbed in the absorption layer is increased, and an amount of substance to be sensed that is discharged without being absorbed is decreased, which leads to enhance the measurement sensitivity and accuracy of the substance to be sensed. Further, the reduction in the height of the reaction channel leads to reduce a volume of the reaction channel, which enables to reduce an amount of sample solution required for the measurement, so that in terms of elimination of necessity of diluting the sample solution as well, the reduction in height contributes to the enhancement in the measurement sensitivity and accuracy of the substance to be sensed.

However, when a case in which the height of the reaction channel is made very small as above is applied to the aforementioned quartz-crystal sensor of twin sensor type, because of a difference in wettability between the two oscillation areas (for example, the hydrophilic oscillation area for measurement having the absorption layer formed of the biological substance or the like formed on the front surface thereof and the hydrophobic oscillation area for reference made of gold), an air bubble is not discharged and remained on the side of the oscillation area with higher hydrophobic property out of the two oscillation areas, which is, for example, the oscillation area for reference made of gold, as shown in FIG. 34, which makes it difficult to conduct the measurement with high reliability.

Further, there is a flow cell system in which a flow cell including supply and discharge channels of a sample fluid (sample solution) is provided to a sensing device, a piezoelectric resonator is disposed in a space formed in the flow cell, and the sample fluid is continuously supplied to a surface of the piezoelectric resonator by using the space as a reaction channel of the sample fluid (Patent Document 3, for example). Since a flow-cell sensing device can continuously supply a sample fluid, it is easy to stabilize a frequency characteristic, and further, a displacement of liquids can be smoothly conducted, so that an amount of sample fluid used can be reduced, which is advantageous.

In such a flow-cell sensing device, it is required to perform operation to dispose a piezoelectric sensor on a flow cell, and mount the piezoelectric sensor to the sensing device by connecting a terminal of electrode of a piezoelectric resonator provided to the piezoelectric sensor to an oscillator circuit. Conventionally, such a mounting operation has been conducted by a user by hand, but, in order to avoid a phenomenon such that a good sensing result cannot be obtained due to a mounting failure and to reduce a period of time of the mounting operation, an automation of process of mounting the piezoelectric sensor has been required.

In Patent Document 4, there is described a sensing device in which a main body part (first part) including a casing in which a piezoelectric sensor is to be inserted (a unit of housing a sensor element) is disposed between opening/closing parts capable of being opened/closed in a horizontal direction (which are described as "second parts" in the specification of Patent Document 4, and in the following citation of Patent Document 4, a name in the specification is described within parentheses). In the casing, there is formed an opening portion at a position corresponding to a position of a piezoelectric resonator of the piezoelectric sensor inserted in the casing, and on one side of the opening/closing parts, a flow cell (flow cell element) capable of being fitted in the opening portion is provided. Further, it is designed such that by moving, after inserting the piezoelectric sensor in the aforementioned casing, the opening/closing parts to a closed position so as to sandwich the main body part from the left and right, the flow cell is fitted in the opening portion of the casing, which enables to supply a sample fluid to the piezoelectric resonator.

In the sensing device described in Patent Document 4, although the operation to connect the flow cell to the casing that houses the piezoelectric sensor is automated, there is no description regarding a method of disposing the piezoelectric sensor in the casing. Therefore, when the operation is conducted by hand, there still remains problems such as an operation loss and a mounting failure.

[Patent Document 1] Japanese Patent Application Laid-open No. 2008-58086 (paragraph 0014, FIG. 11 and FIG. 13)

[Patent Document 2] Japanese Patent Application Laid-open No. 2007-108170

[Patent Document 3] Japanese Patent Application Laid-open No. H11-183479: paragraph 0002, paragraph 0024, and FIG. 2

[Patent Document 4] Translated National Publication of Patent Application No. 2006-510901: Claim 1, paragraph 0026, FIG. 2, FIG. 4 and FIG. 7

SUMMARY OF THE INVENTION

The present invention has been made based on such circumstances, and an object thereof is to provide a sensing device capable of performing measurement, with high reliability, of a substance to be sensed while letting a sample solution flow.

Further, an another object of the present invention is to provide a sensing device that automatically mounts a piezoelectric sensor to make it possible to obtain a uniform connection state every time a mounting operation is conducted.

A sensing device of the present invention that senses a substance to be sensed in a sample solution by using a piezoelectric sensor having a common piezoelectric piece on which a piezoelectric resonator is formed by providing two pairs of excitation electrodes are provided to be arranged in an X direction to form a first oscillation area and a second oscillation area, in which an absorption layer absorbing the substance to be sensed in the sample solution is formed on the first oscillation area out of the excitation electrodes on one surface side of the piezoelectric piece, and the absorption layer is not formed on the second oscillation area on the one surface side, the sensing device includes: a channel forming member being closely contacted on one surface side of the piezoelectric sensor, having an opposing surface opposing the first oscillation area and the second oscillation area via a gap, and forming a reaction channel on an area facing the one surface side; a liquid supply port being provided on one end side in a Y direction orthogonal to the X direction in the reaction channel and supplying the sample solution to the reaction channel; a liquid discharge port being provided on the other end side in the Y direction in the reaction channel and discharging the sample solution from the reaction channel; and a groove part formed on the opposing surface to control a liquid flow for the purpose of suppressing a concentration of liquid flow caused because the first oscillation area has a hydrophilic property and the second oscillation area has a hydrophobic property due to the presence/absence of the absorption layer, in which the first oscillation area and the second oscillation area are provided to sense, when the piezoelectric sensor is oscillated by oscillator circuits, the substance to be sensed based on oscillation frequencies of these oscillation areas.

Further, as concrete examples of the sensing device, there can be cited the following examples.

1. A height of the reaction channel facing the one surface side of the piezoelectric sensor is 0.3 mm or less.

2. The groove part has a first groove portion extending from the liquid discharge port side toward the first oscillation area, and a second groove portion extending from the liquid discharge port side toward the second oscillation area, in which end portions on the sides of the oscillation areas of the first groove portion and the second groove portion are respectively positioned not to overlap with the first oscillation area and the second oscillation area.

At this time, in the present invention, the first groove portion and the second groove portion may also be formed to have a distance therebetween gradually increasing toward the sides of the oscillation areas from the liquid discharge port, when seen from the above, and further, it is also possible that the first groove portion is on the side of a line connecting the liquid supply port and the liquid discharge port, from an edge of the reaction channel extending from the liquid discharge port to the first oscillation area side, and the second groove portion is on the side of the line, from an edge of the reaction channel extending from the liquid discharge port to the second oscillation area side.

Further, a sensing device according to an another invention being a sensing device that makes a piezoelectric sensor having a piezoelectric resonator and used in a state of being stacked with the aforementioned channel forming member move forward to mount the sensor to a measuring device main body, makes the piezoelectric sensor move backward to detach the sensor from the measuring device main body, and senses a substance to be sensed based on a variation in an oscillation frequency of the piezoelectric resonator caused by an absorption of the substance to be sensed in an absorption layer provided on an absorption surface of the piezoelectric resonator, the sensing device includes: a connecting part being provided to the measuring device main body and connecting terminals to be connected of the piezoelectric resonator to oscillator circuits; a holding member detachably holding the piezoelectric sensor; a movable body to which the holding member is mounted with an allowance with which it can move in a longitudinal direction; a moving mechanism moving the movable body forward and backward in a horizontal direction between a holding position set on a near side of the connecting part and at which the holding member holds the piezoelectric sensor and a connecting position at which the terminals to be connected are connected to the connecting part to mount the piezoelectric sensor to the measuring device main body; and a guide member by which the holding member is guided forward in a state of being placed on the guide member when the movable body is moved from the holding position to the connecting position.

The sensing device may have characteristics as follows.

(a) The holding position is set on a near side of the guide member, an upper surface of a tip portion on the near side of the guide member is provided with a guide surface formed of an inclined surface formed to have an inclination gradually increasing from a near side to a far side, the holding member is provided with, on its lower surface of an area opposing the guide surface, a surface to be guided formed of an inclined surface formed to have an inclination gradually increasing from the near side to the far side, and when the movable body is moved from the holding position to the connecting position, the holding member is guided forward in a state of being placed on the guide member after the surface to be guided thereof runs upon the guide member while being guided by the guide surface of the guide member.

(b) There are provided a fixing member fixing the channel forming member stacked on the piezoelectric sensor mounted to the measuring device main body by pressing it against the piezoelectric sensor, and a raising/lowering mechanism raising/lowering the fixing member between a fixing position at which the channel forming member is fixed and a retreat position retreating from the fixing position.

(c) There are formed, on the fixing member, a supply channel for supplying the sample solution into a passage space through a liquid supply port provided to the channel forming member, and a discharge channel for discharging the sample solution through a liquid discharge port provided to the channel forming member.

(d) The raising/lowering mechanism stops, when a load greater than a previously set load is applied at a time of raising/lowering the fixing member between the fixing position and the retreat position, the raising/lowering of the fixing member.

(e) A temperature adjusting mechanism for keeping a temperature of the piezoelectric resonator connected to the oscillator circuits at a previously set temperature, is provided to the measuring device main body.

(f) The piezoelectric resonator is provided with a first oscillation area and a second oscillation area disposed in an area different from the first oscillation area via an elastic boundary area, and there are provided a first oscillator circuit and a second oscillator circuit for oscillating these first oscillation area and second oscillation area, respectively.

(g) The moving mechanism stops, when a load greater than a previously set load is applied at a time of moving the movable body between the holding position and the connecting position, the movement of the movable body.

A sensing device according to the present invention that connects a piezoelectric resonator of the aforementioned piezoelectric sensor to oscillator circuits via a connecting part provided to a measuring device main body, and senses a substance to be sensed based on a variation in an oscillation frequency of the piezoelectric resonator caused by an absorption of the substance to be sensed in an absorption layer provided on an upper surface of the piezoelectric resonator, the sensing device includes: a holding member holding the piezoelectric sensor to create a state where the piezoelectric resonator is detachable with respect to the connecting part, and holding the aforementioned channel forming member in a state of being stacked on the piezoelectric sensor, the channel forming member forming a passage space through which a sample solution passes on the upper surface side of the piezoelectric resonator by being placed on the piezoelectric sensor, being made of an elastic material and provided with a liquid supply port and a liquid discharge port of the sample solution; a sample solution supply part having a supply channel of the sample solution communicated with the liquid supply port and a sample solution discharge part having a discharge channel of the sample solution communicated with the liquid discharge port; a cover member placed on the channel forming member in a state where the piezoelectric resonator is connected to the connecting part; a pressing part pressing the cover member placed on the channel forming member with a previously set force toward the channel forming member; and a first raising/lowering mechanism raising/lowering the pressing part between a pressing position at which the pressing part presses the cover member and a release position retreating from the pressing position and at which the cover member is released from the pressed state.

The sensing device may have characteristics as follows.

(h) The sample solution supply part and the sample solution discharge part are made common with the cover member.

(i) The pressing part has a spring member biased in a direction of pressing the cover member and an abutting member provided at a tip portion of the spring member and abutting on the cover member.

(j) There is provided a second raising/lowering mechanism raising/lowering the cover member between a placing position at which the cover member is placed on the channel forming member and an attaching/detaching position retreating from the placing position and at which the piezoelectric sensor held to the holding member can be attached/detached to/from the connecting part.

(k) The first raising/lowering mechanism and the second raising/lowering mechanism are made common.

(l) There is provided a moving mechanism moving the holding member forward and backward in a horizontal direction between a holding position set on a near side of the connecting part and at which the holding member holds the piezoelectric sensor and a connecting position at which the piezoelectric sensor is mounted to a measuring device main body in a state where the piezoelectric resonator is connected to the connecting part.

The present invention forms, in a sensing device in which a reaction channel is formed to face a twin-type piezoelectric sensor having an oscillation area for measurement (first oscillation area) and an oscillation area for reference (second oscillation area) arranged in an X direction, and a flow-in port and a flow-out port of a sample solution in the reaction channel are arranged in a Y direction, a groove part on the flow-out port side in an opposing surface opposing the piezoelectric sensor, to thereby suppress a concentration of liquid flow caused by a difference in a level of wettability of both the oscillation areas. Therefore, it is possible to prevent an air bubble from remaining in the reaction channel, which enables to perform measurement with high reliability.

DETAILED DESCRIPTION OF THE PREFERRED EMBODIMENT(S)

Figure 1:
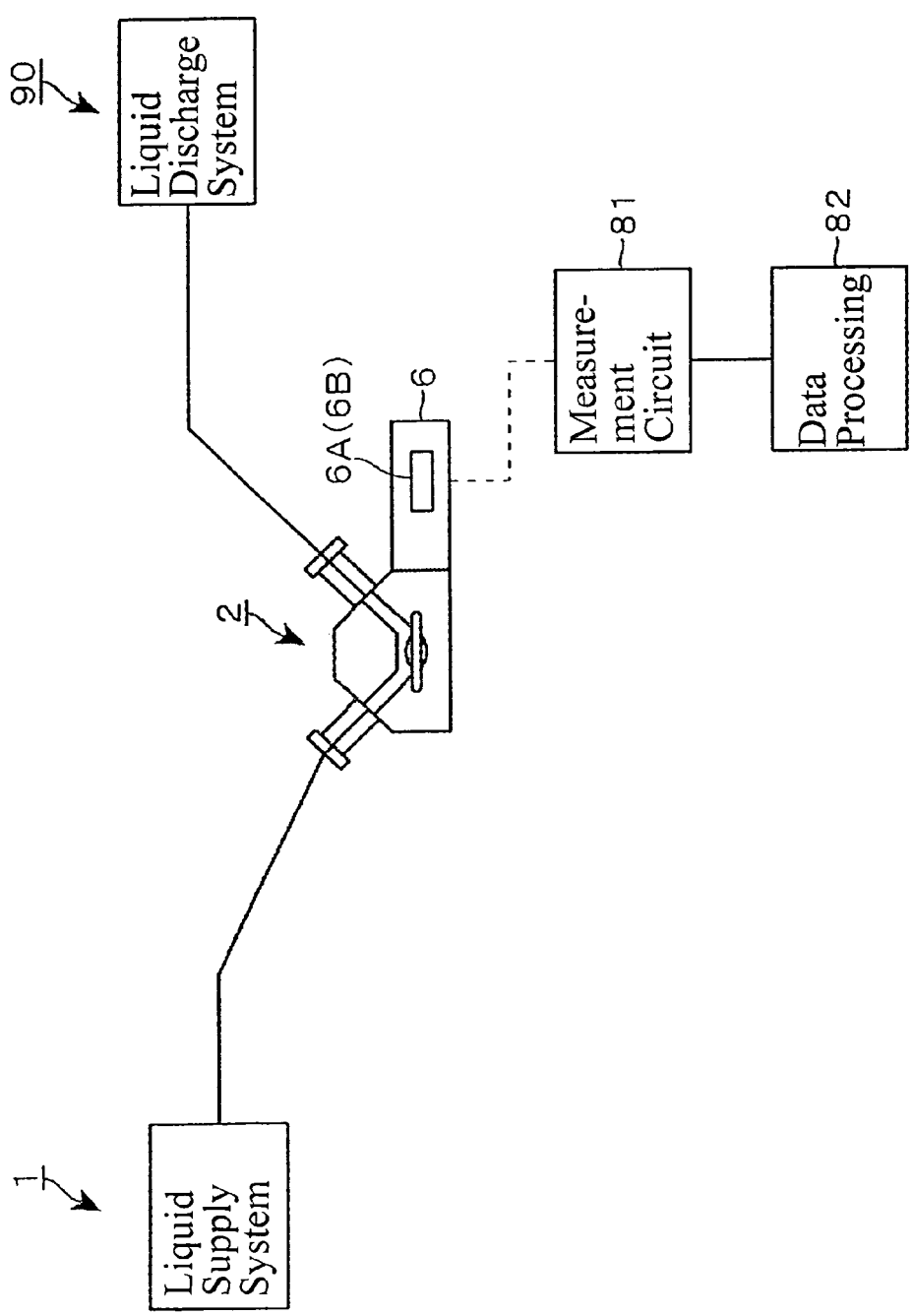
FIG. 1 is a schematic diagram showing an entire structure of a sensing device according to the present invention.

As shown in FIG. 1, an embodiment of a sensing device of the present invention includes: a sensor unit 2; a liquid supply system 1 that supplies a liquid (sample solution and buffer solution) to the sensor unit 2; a liquid discharge system 90 that stores the liquid discharged from the sensor unit 2; a quartz-crystal sensor 7 being a piezoelectric sensor mounted to the sensor unit 2; and an oscillator circuit unit 6 provided adjacent to the sensor unit 2.

Figure 2:
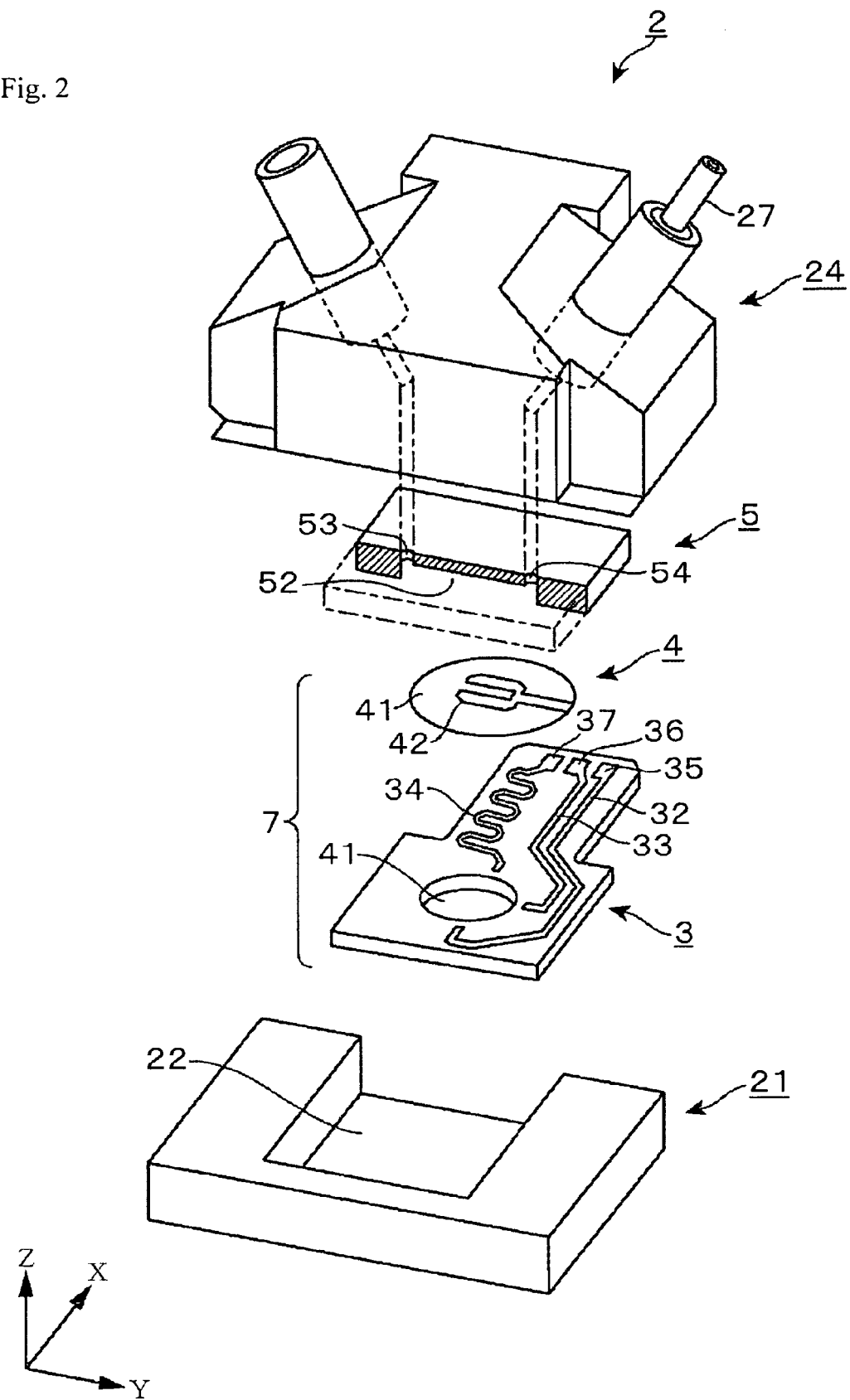
FIG. 2 is an exploded perspective view showing a sensor unit including a piezoelectric sensor according to the present invention.

As shown in FIG. 2, the sensor unit 2 is formed of a support 21, a wiring board 3, a quartz-crystal resonator 4, a channel forming member 5 and a cover 24, which are stacked in this order from the bottom. In the support 21, there is formed a concave portion of support 22 in which the quartz-crystal sensor 7 and the channel forming member 5 are fitted and held. Therefore, by pressing the channel forming member 5 against the quartz-crystal sensor 7 in a state where the quartz-crystal sensor 7 is fitted in the concave portion of support 22, a lower surface of the channel forming member 5 presses the quartz-crystal resonator 4 against the wiring board 3, to thereby fix the quartz-crystal resonator. Further, the support 21 is covered from above by the cover 24.

Figure 3:
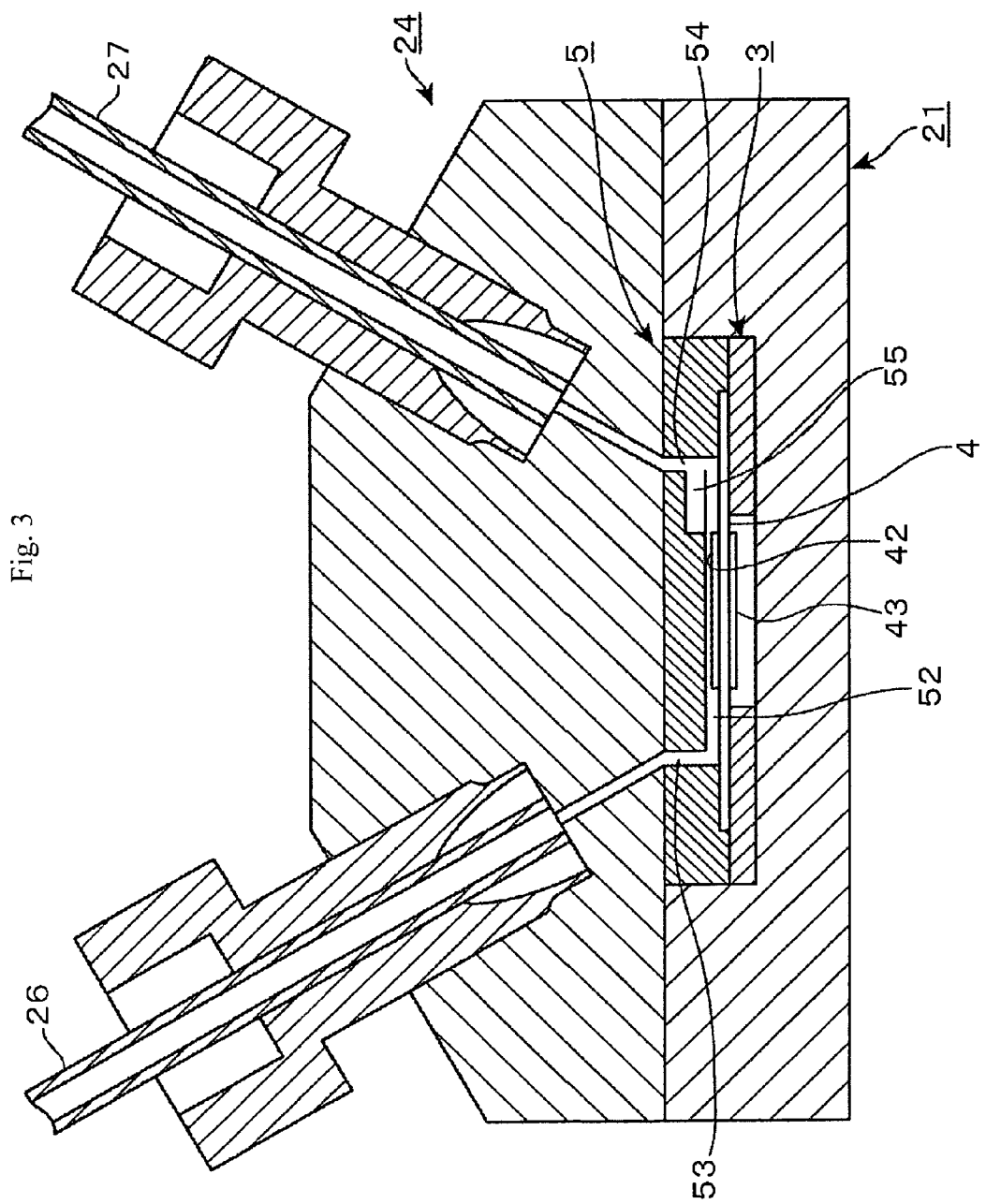
FIG. 3 is vertical sectional side view showing the sensor unit.
Figure 26:
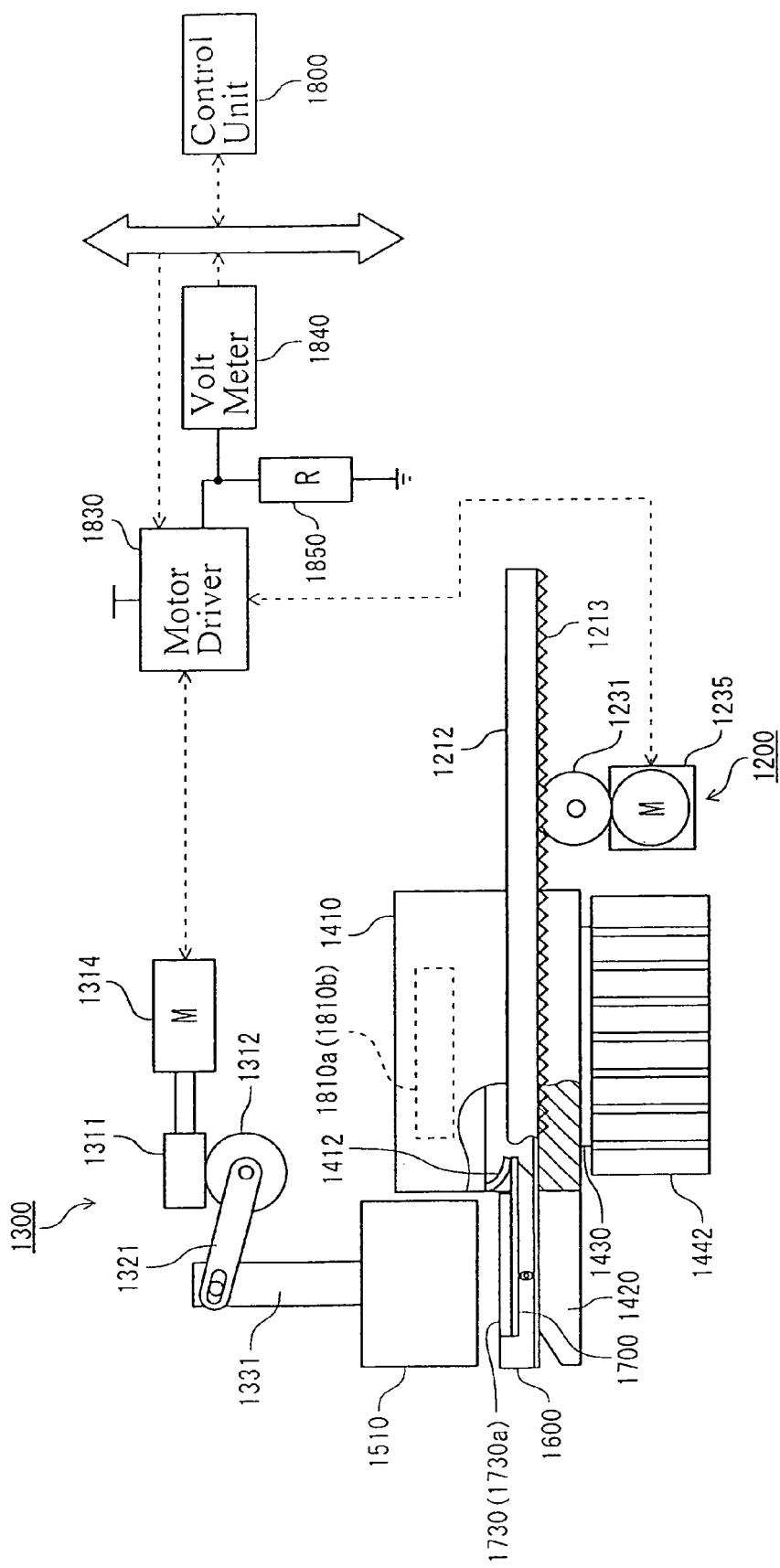
FIG. 26 is a block diagram showing an electrical structure according to the moving mechanism and the raising/lowering mechanism provided to the sensing device.

In FIG. 2 and FIG. 3, 26 denotes a liquid supply pipe and 27 denotes a liquid discharge pipe being a discharge unit, in which it is structured such that a liquid supplied to a reaction channel 52 from the liquid supply system 1 through the liquid supply pipe 26 passes through the liquid discharge pipe 27 to be discharged to the liquid discharge system 90. The liquid supply system 1 includes a buffer solution supply part and a sample solution supply part which supply the buffer solution as a reference solution and the sample solution, respectively, to the quartz-crystal sensor 7, and the liquid discharge system 90 includes a waste liquid reservoir part.

Figure 4A:
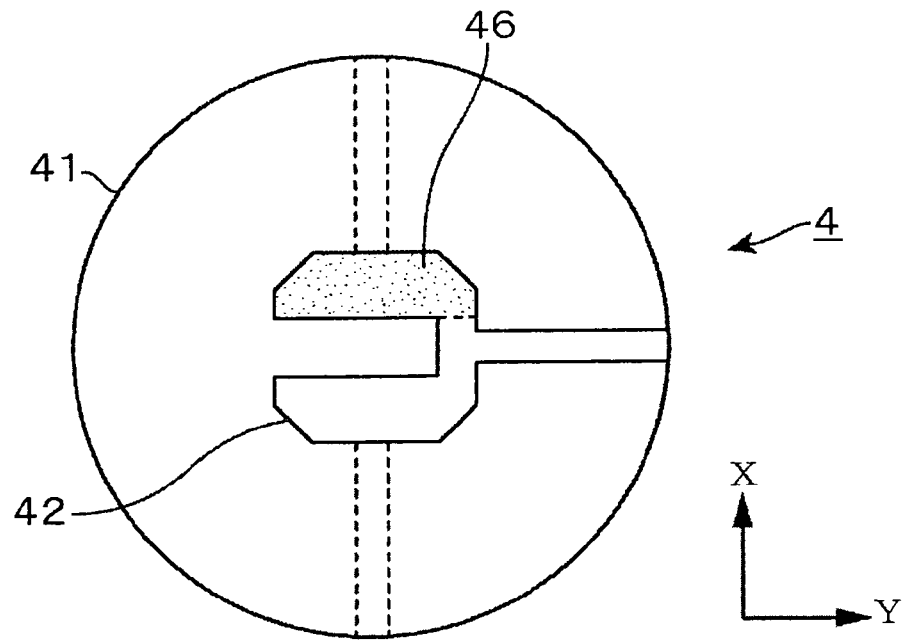
FIGS. 4(a) and 4(b) are a front surface view and a rear surface view showing a quartz-crystal resonator that forms a part of the piezoelectric sensor.
Figure 4B:
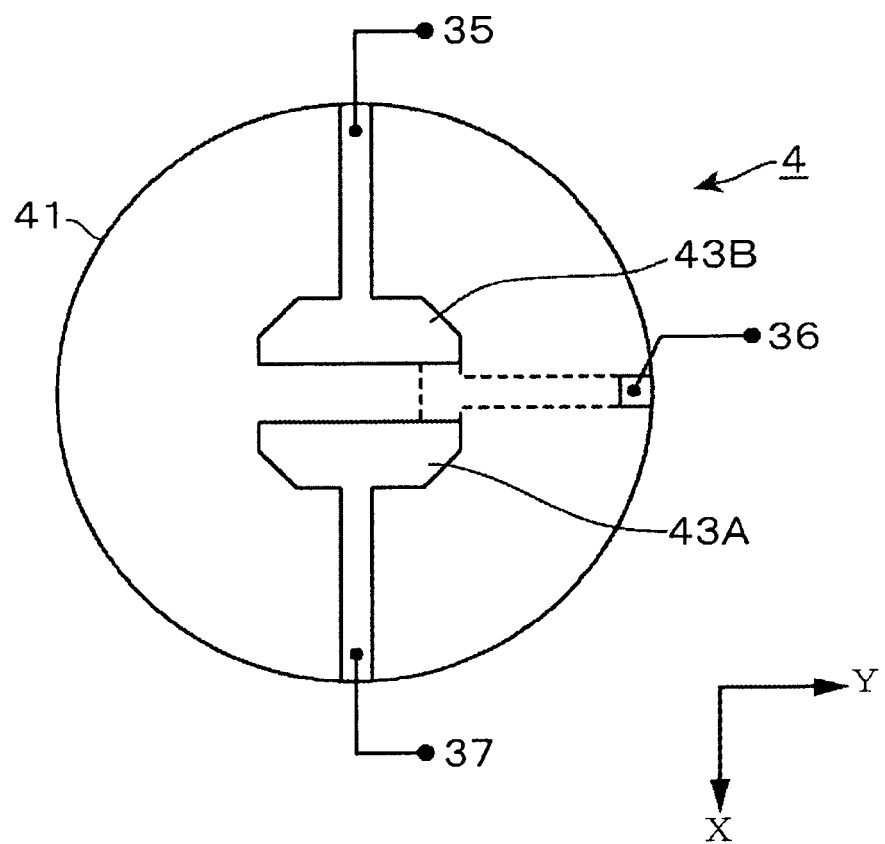
Figure 5:
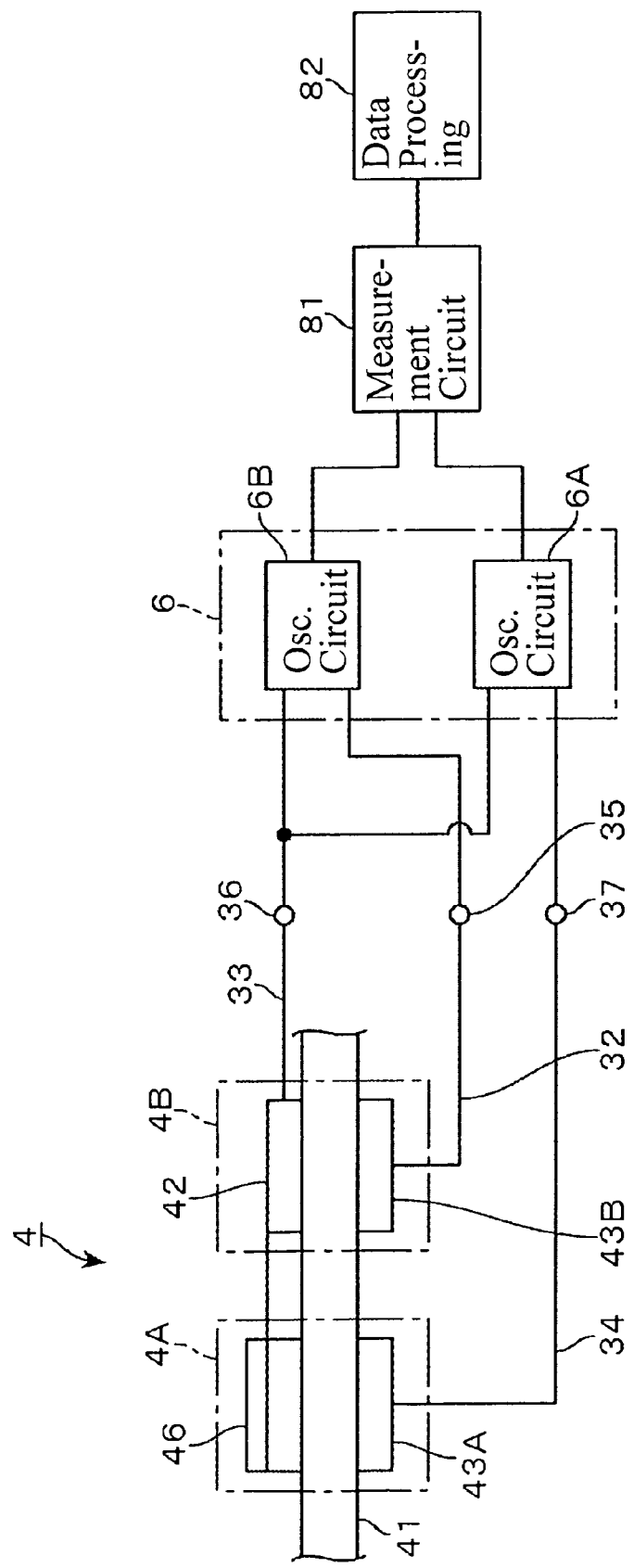
FIG. 5 is a block diagram explaining a connection between the quartz-crystal resonator that forms a part of the sensing device and a frequency measuring part.

The quartz-crystal sensor 7 is formed by providing the quartz-crystal resonator 4 being a piezoelectric resonator on the wiring board 3. As shown in FIG. 4, the quartz-crystal resonator 4 is formed by providing excitation electrodes 42, 43 on both surfaces of a quartz-crystal piece 41 in a disk shape being a piezoelectric piece and, in this example, a first excitation electrode 43A and a second excitation electrode 43B are disposed to be arranged in an X direction by being separated from each other on a rear surface side (FIG. 4(b)) and an excitation electrode (common electrode) 42 common to the aforementioned two excitation electrodes 43A, 43B is disposed on a front surface side (FIG. 4(a)) of the quartz-crystal piece. Accordingly, the first excitation electrode 43A and the common electrode 42 form a first oscillation area 4A, and the second excitation electrode 43B and the common electrode 42 form a second oscillation area 4B. Note that an equivalent thickness of each of the common electrode 42 and the excitation electrodes 43A, 43B is, for example, 0.2 μm, and as an electrode material, gold, silver or the like is used, for example. When the quartz-crystal sensor 7 is mounted to the sensor unit 2, the first excitation electrode 43A and the second excitation electrode 43B are respectively connected to two oscillator circuits 6A, 6B via conductive paths 32, 34 on the wiring board 3, and the common electrode 42 is connected to a ground side of the oscillator circuits 6A, 6B via a conductive path 33 on the wiring board 3, as shown in FIG. 5. On an end area of the aforementioned wiring board 3, connection terminals 35 to 37 respectively connected to the respective conductive paths 32 to 34 are formed.

Further, on an area corresponding to the first excitation electrode 43A of the common electrode 42 of the quartz-crystal sensor 7, an absorption layer (reactant) 46 formed of an antibody for absorbing an antigen being a substance to be sensed is formed. Therefore, when a substance to be sensed in a sample solution, for instance, is absorbed in the aforementioned absorption layer 46, an oscillation frequency in the first oscillation area 4A is lowered by a mass load effect. Meanwhile, in the second oscillation area 4B, a front surface of the common electrode is exposed and the absorption layer 46 is not provided thereon, so that the substance to be sensed is not absorbed in the common electrode 42. Accordingly, by comparing the oscillation frequencies in the respective areas 4A, 4B before and after the absorption of the substance to be sensed, it becomes possible to sense a variation (amount of decrease) in the oscillation frequency corresponding to an amount of the substance to be sensed absorbed in the absorption layer 46, by reducing an influence of disturbance such as a temperature surrounding the sensor unit 2, a viscosity of the sample solution, and an adhesion of a substance other than the substance to be sensed contained in the sample solution. Note that it is also possible to design such that the front surface of the common electrode in the area that forms the second oscillation area is not exposed, and, for example, a blocking layer formed of a protein that does not react with the substance to be sensed is formed thereon.

Figure 6:
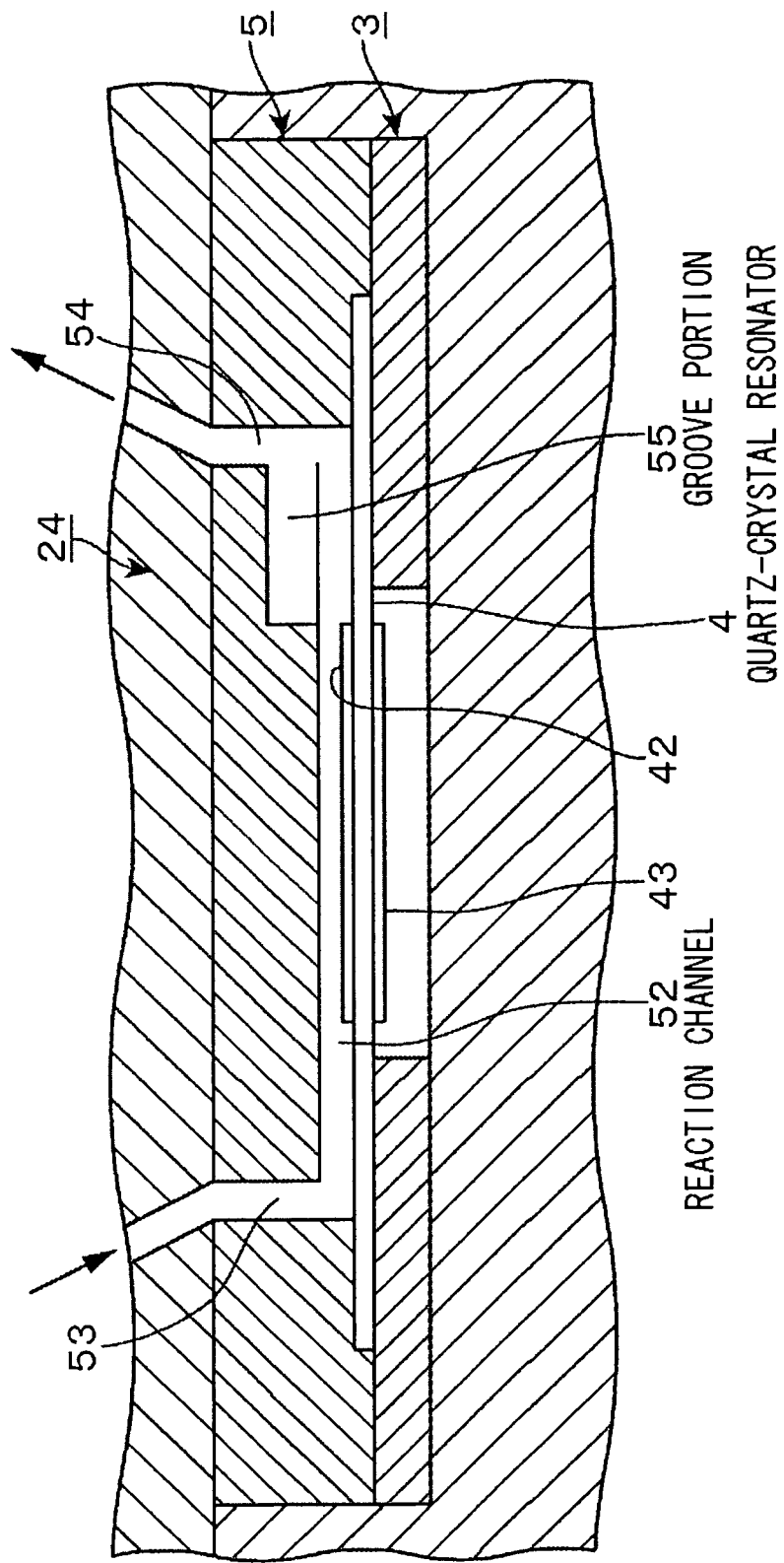
FIG. 6 is a vertical sectional side view showing the sensor unit in an enlarged manner.
Figure 7A:
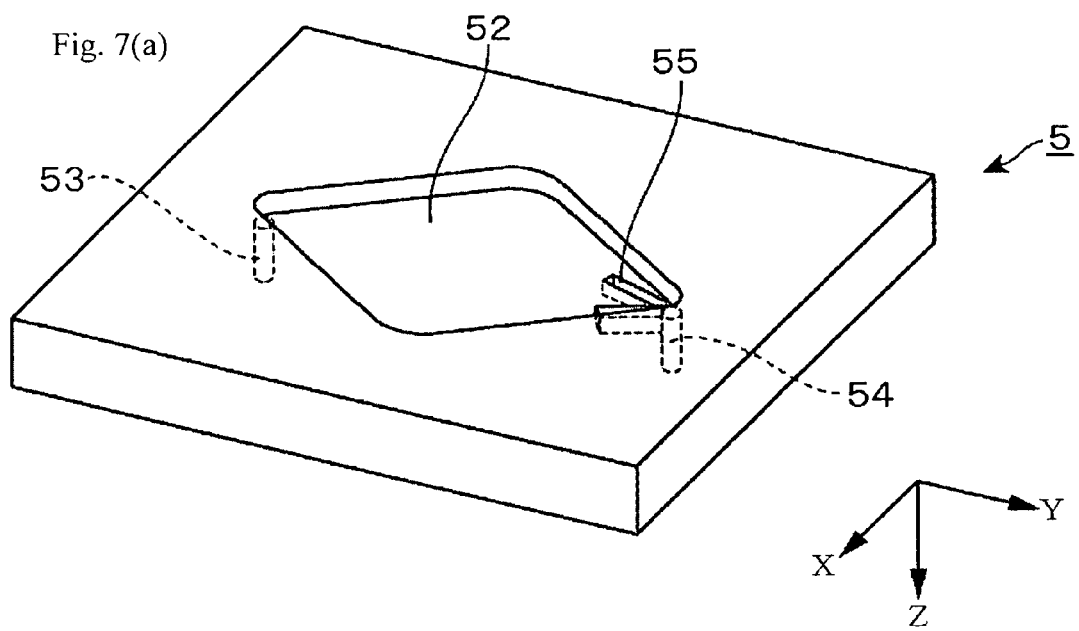
FIGS. 7(a) and 7(b) are perspective views showing a rear surface and a front surface, respectively, of a channel forming member that forms a part of the sensor unit.
Figure 7B:
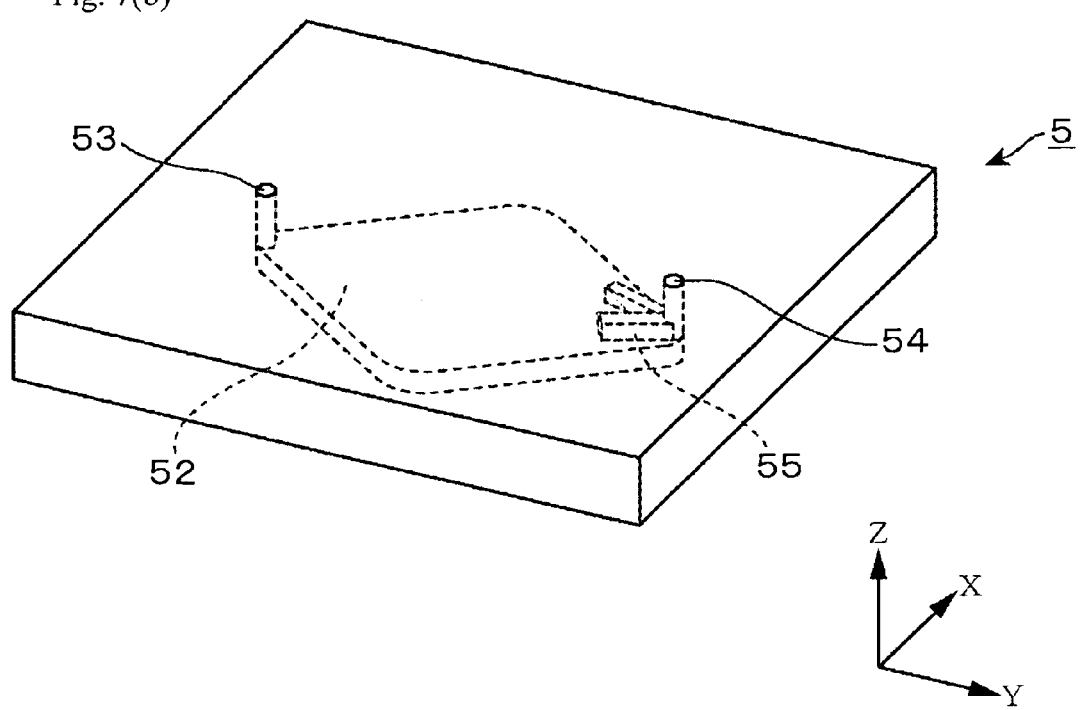

Next, the channel forming member 5 will be explained using FIG. 6 and FIG. 7. FIG. 6 is a view showing a vertical section of the sensor unit 2 in an enlarged manner. FIGS. 7(a) and 7(b) show a rear surface side and a front surface side, respectively, of the channel forming member 5, in which a height of a concave portion 52 is illustrated in an exaggerated manner. The channel forming member 5 is formed in a shape corresponding to that of one end side of the wiring board 3, by using an elastic material which is, for example, polydimethylsiloxane (PDMS). On a center portion on the rear surface side of the channel forming member 5, there is formed the concave portion 52, and by laying the channel forming member 5 and the wiring board 3 one on the other so that the rear surface side of the channel forming member 5 is brought into contact with the wiring board 3 and pressing them against the quartz-crystal resonator 4, the concave portion 52 serves as a reaction channel. Specifically, at this time, a ceiling surface of the concave portion 52 is an opposing surface opposing the oscillation areas on the front surface side being one surface side of the quartz-crystal resonator 4 via a gap, and the reaction channel is formed in an area between the opposing surface and the quartz-crystal resonator 4 so as to be surrounded by an inner peripheral surface along a contour of the concave portion 52. For this reason, both the concave portion and the reaction channel are set to be denoted by a reference numeral 52. The concave portion 52 has a shape of rhombus with curved corners, so that a dead space with respect to a flow of liquid in the reaction channel 52 is not generated. A center portion of the concave portion 52 is set to be slightly larger than an area of the quartz-crystal resonator 4 including the first oscillation area 4A and the second oscillation area 4B, and when the channel forming member 5 abuts on the wiring board 3, the areas 4A, 4B are designed to be located at the center portion in the concave portion 52. Further, the height of the concave portion 52 is set to 0.3 mm or less, for example, and is set to 0.15 mm in this example. Further, at places corresponding to both ends on a diagonal line in a Y direction of the opposing surface of the concave portion 52, there are formed channels in a vertical direction with respect to the opposing surface (Z direction) from the rear surface toward the front surface of the channel forming member 5. One of the channels vertical with respect to the opposing surface corresponds to a liquid supply port 53, and the other thereof corresponds to a liquid discharge port 54.

Figure 8:
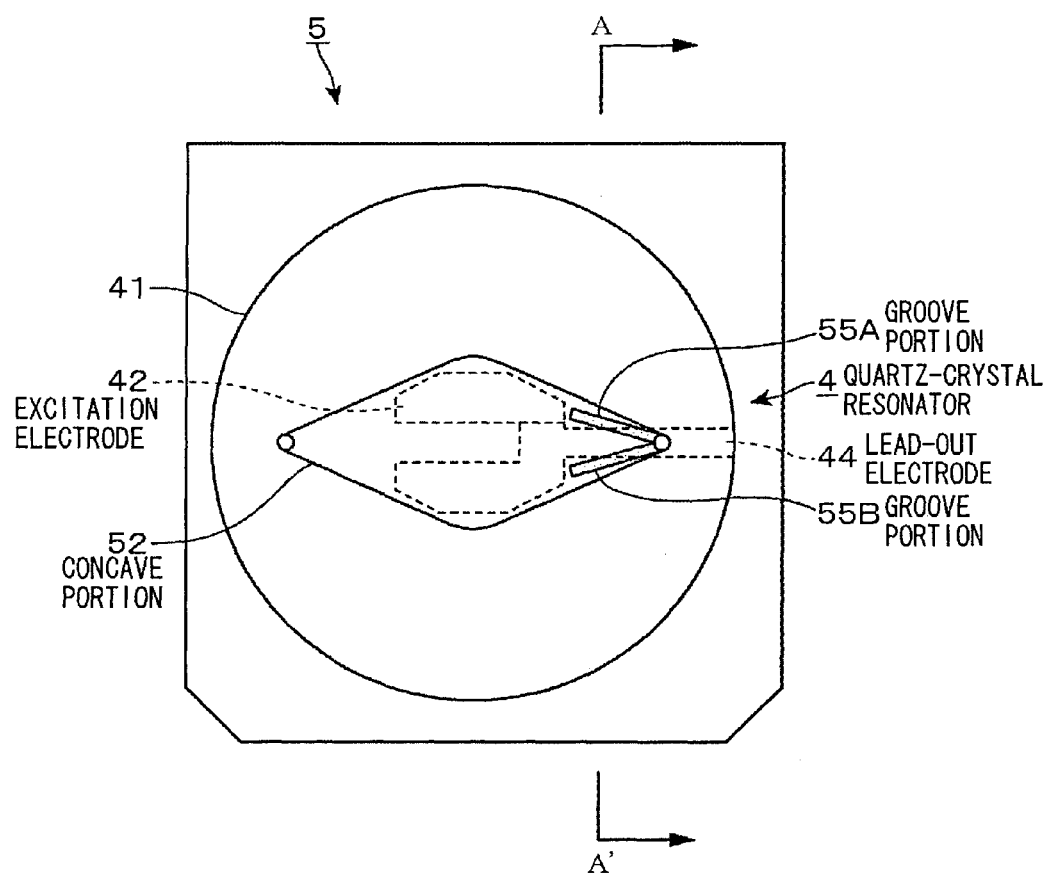
FIG. 8 is an explanatory diagram showing a positional relationship among groove portions and excitation electrodes when the channel forming member and the quartz-crystal resonator abut.
Figure 9:
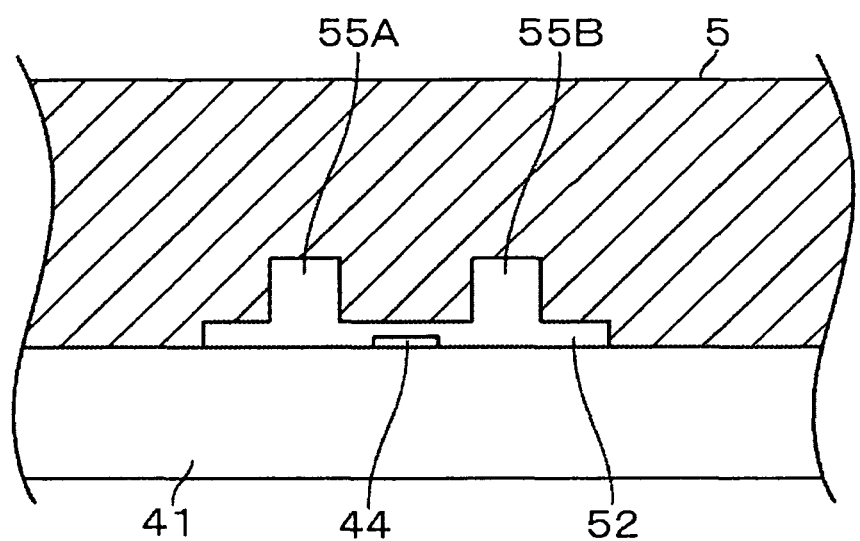
FIG. 9 is an arrow sectional view taken along a line A-A' showing a cross section of the groove portions in FIG. 8.

Further, as shown in FIG. 8 and FIG. 9, on the opposing surface of the concave portion 52, there are formed two groove portions 55A, 55B extending linearly from the liquid discharge port 54 toward the first oscillation area 4A and the second oscillation area 4B. These groove portions 55A, 55B are formed to oppose a quartz-crystal part of the quartz-crystal resonator 4, and end portions on the sides of the oscillation areas 4A, 4B of the groove portions 55A, 55B are respectively positioned not to oppose both the oscillation areas 4A, 4B. Further, these groove portions 55A, 55B are formed to have a distance therebetween (distance in the X direction) increasing from the liquid discharge port 54 toward the sides of the oscillation areas 4A, 4B, respectively, to form an entire planar shape of V shape, and are on the side of a line connecting the liquid supply port 53 and the liquid discharge port 54 from edges of the reaction channel 52 extending from the liquid discharge port 54 to the respective oscillation areas 4A, 4B sides. In this example, each size of the two groove portions 55A, 55B is set to, for example, a length of 3 mm, a width of 0.5 mm and a depth of 0.5 mm.

Further, when the oscillator circuit unit 6 is inserted in the sensor unit 2, it is electrically connected to connection terminal portions of the wiring board 3, as shown in FIG. 5. On a subsequent stage of the oscillator circuit unit 6, a measurement circuit part 81 and a data processing part 82 are provided. The measurement circuit part 81 has a function to perform digital processing on a frequency signal being an input signal, for instance, to measure an oscillation frequency. Note that the measurement circuit part 81 may be a frequency counter, and a measuring method thereof can be appropriately selected. The data processing part 82 is a part that stores time-series data of the measured frequency and displays the time-series data, and is formed of, for instance, a personal computer.

Next, operations of the sensing device will be explained by using FIG. 10. When a liquid is supplied into the sensor unit 2 from the liquid supply system 1, the liquid flows in the reaction channel 52 through the liquid supply port 53. Thereafter, when the inflowed liquid reaches the first oscillation area 4A and the second oscillation area 4B while radially spreading on both sides toward the liquid discharge port 54 in the reaction channel 52 (FIG. 10(a)), the flow of liquid is concentrated on the side of the hydrophilic first oscillation area 4A, due to a difference in wettability between both the oscillation areas 4A and 4B (FIG. 10(b)). Here, when there is no groove portion 55A, a large part of the liquid passes through the hydrophilic oscillation area 4A as above, and further, a part thereof enters around the hydrophobic oscillation area 4B side from the vicinity of the liquid discharge port 54, resulting in that an air bubble sometimes remains on the hydrophobic oscillation area 4B side, which is a cause to reduce the reliability of measurement.

On the contrary, when the reaction channel 52 was actually manufactured in a size of this embodiment, no air bubble was confirmed in the present sensing device. A reason thereof can be estimated as follows. Since there is the groove portion 55A, an action to spread out the liquid on both sides from below the groove portion 55A in the reaction channel 52 acts due to an influence of surface tension, which results in suppressing one-sided outflow of liquid from the hydrophilic area 4A side. For this reason, the thrust of liquid entering the hydrophobic area 4B side is increased according thereto, resulting in that the liquid starts entering the hydrophobic area 4B as well (FIG. 10(c)). After that, the liquid from the hydrophilic area 4A side passes over a lead-out electrode 44 made of gold with hydrophobic property to enter the hydrophobic area 4B side, and also at this point, the liquid is obstructed by the groove portion 55B on the hydrophobic area 4B side, and is bypassed in a direction opposite to that of the liquid discharge port 54 along the groove portion 55B.

Figure 10A:
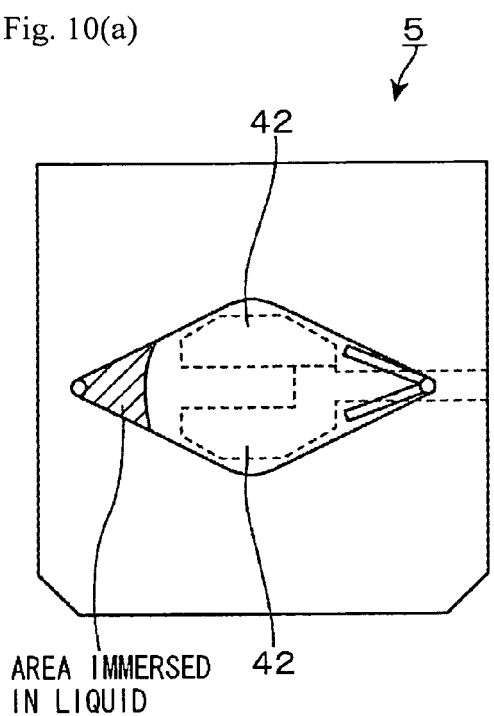
FIGS. 10(a), 10(b), 10(c) and 10(d) are plan views showing an inflow state of liquid over time, for explaining an operation of the groove portions.
Figure 10B:
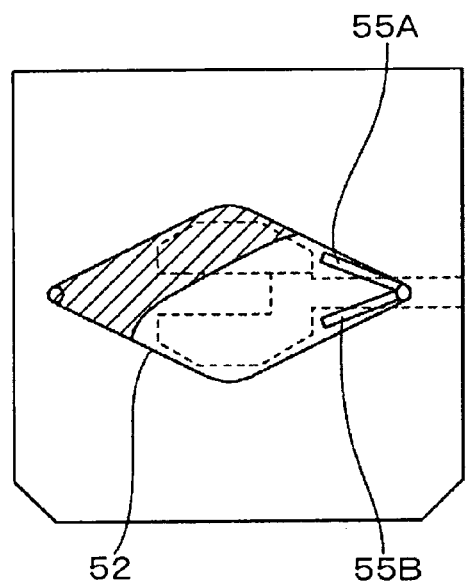
Figure 10C:
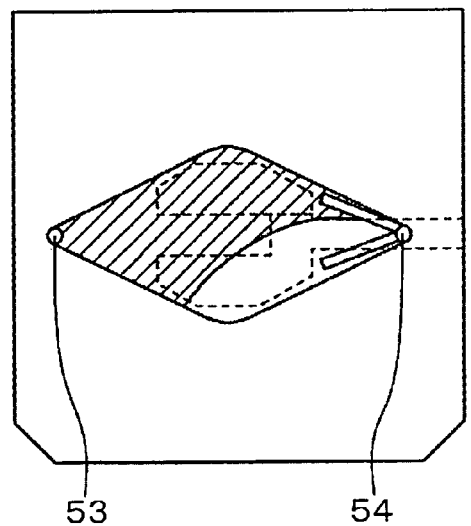
Figure 10D:
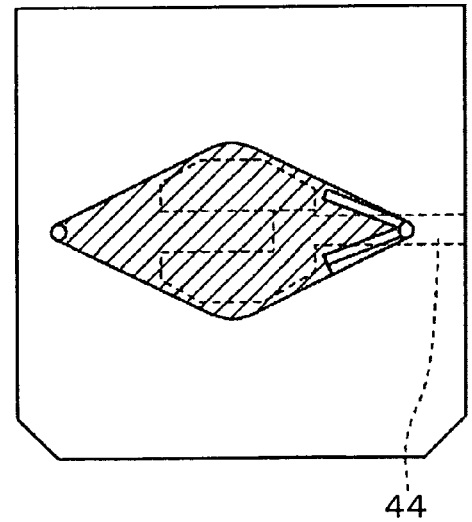

During the period of time, the liquid from the hydrophobic area 4B side also reaches the groove portion 55B on the hydrophobic area 4B side, and further, since an area between the groove portion 55B on the hydrophobic area 4B side and an edge of the reaction channel 52 on the hydrophobic area 4B side functions as an escape route of air bubble to the end (FIG. 10(d)), there is no chance that the air bubble remains, which realizes a uniform extrusion flow in both the oscillation areas 4A, 4B in the reaction channel 52. After that, until when the liquid enters an area under the groove portions 55A, 55B, the flow of liquid concentrates in the vicinity of the edge of the reaction channel 52 in which the air bubble is likely to remain and a flow speed of liquid is increased, which also contributes to prevent the air bubble from remaining in the channel. Further, since the groove portions 55A, 55B do not overlap with both the oscillation areas 4A, 4B, respectively, they do not obstruct the measurement such that they disturb the flow of liquid in the oscillation areas 4A, 4B, for example. Further, the liquid reached the liquid discharge port 54 is discharged to the liquid discharge system 90.

Meanwhile, the first oscillation area 4A and the second oscillation area 4B of the quartz-crystal sensor 7 are respectively oscillated by the oscillator circuit unit 6, and oscillation frequencies thereof are taken into the measurement circuit part 81. Subsequently, a difference between the oscillation frequency in the first oscillation area 4A and the oscillation frequency in the second oscillation area 4B is taken out by the data processing part 82, and the difference is evaluated as an absorption amount of substance to be sensed.

According to the aforementioned embodiment, in the sensing device in which the reaction channel 52 is formed to face the twin-type quartz-crystal sensor 7 on which the oscillation area for measurement (first oscillation area) 4A and the oscillation area for reference (second oscillation area) 4B are arranged in the X direction, and the liquid supply port 53 and the liquid discharge port 54 of sample solution are arranged in the Y direction, the groove portions 55A, 55B are respectively formed on the liquid discharge port 54 side in the opposing surface opposing the quartz-crystal sensor 7, thereby suppressing the concentration of liquid flow caused by the difference in the level of wettability of both the oscillation areas 4A, 4B. Therefore, it is possible to prevent the air bubble from remaining in the reaction channel 52, which enables to perform measurement with high reliability.

Figure 11A:
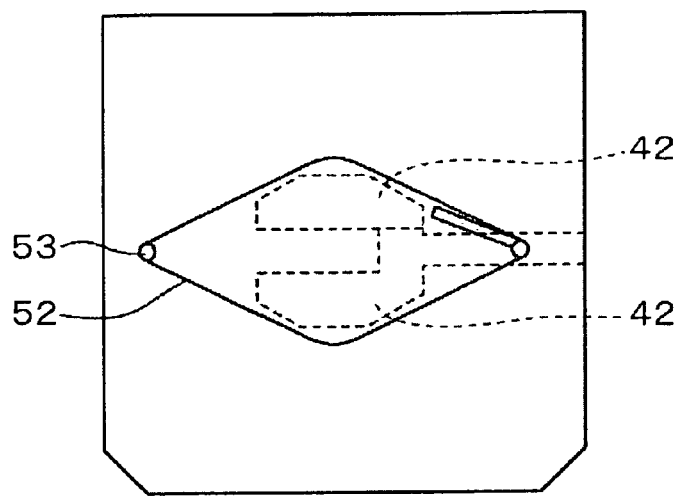
FIGS. 11(a), 11(b) and 11(c) are plan views of channel forming members showing examples of other embodied shapes regarding the groove portion.
Figure 11B:
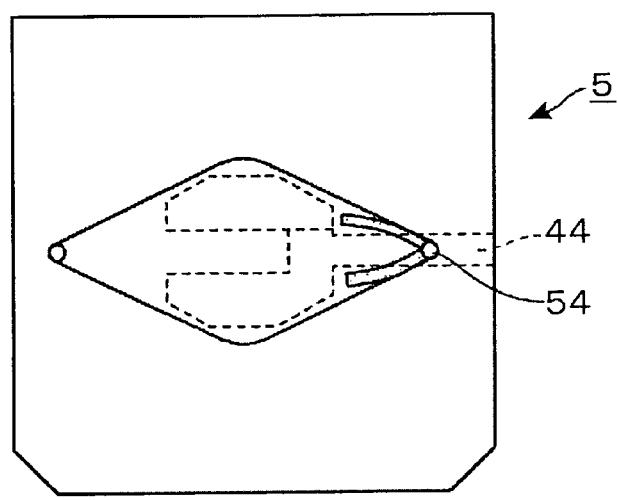
Figure 11C:
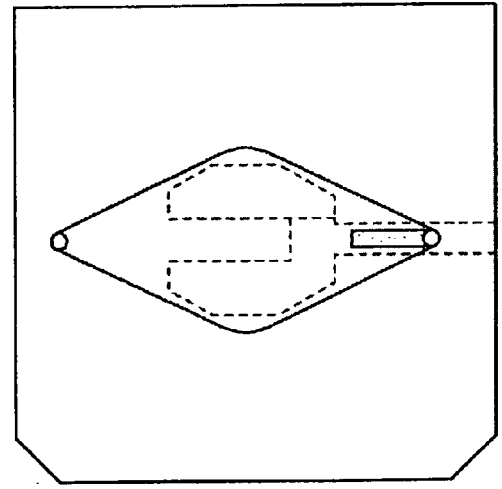

In the above-described example, the groove portions 55 in the channel forming member 5 are formed linearly from the liquid discharge port 54 toward both the oscillation areas 4A, 4B, but, it is not limited to this structure. As one of the functions of the groove portions 55, there can be cited a prevention of liquid from entering around the hydrophobic area 4B side from the hydrophilic area 4A side, so that it is also possible that only one groove portion 55 is formed only on the hydrophilic first oscillation area 4A side, as shown in FIG. 11(a). Further, it is also possible that the groove portions 55 have a curved shape (FIG. 11(b)), or only one groove portion is formed from a point between both the oscillation areas 4A and 4B, namely, the liquid discharge port 54, toward the liquid supply port 53 (FIG. 11(c)).

Figure 12:
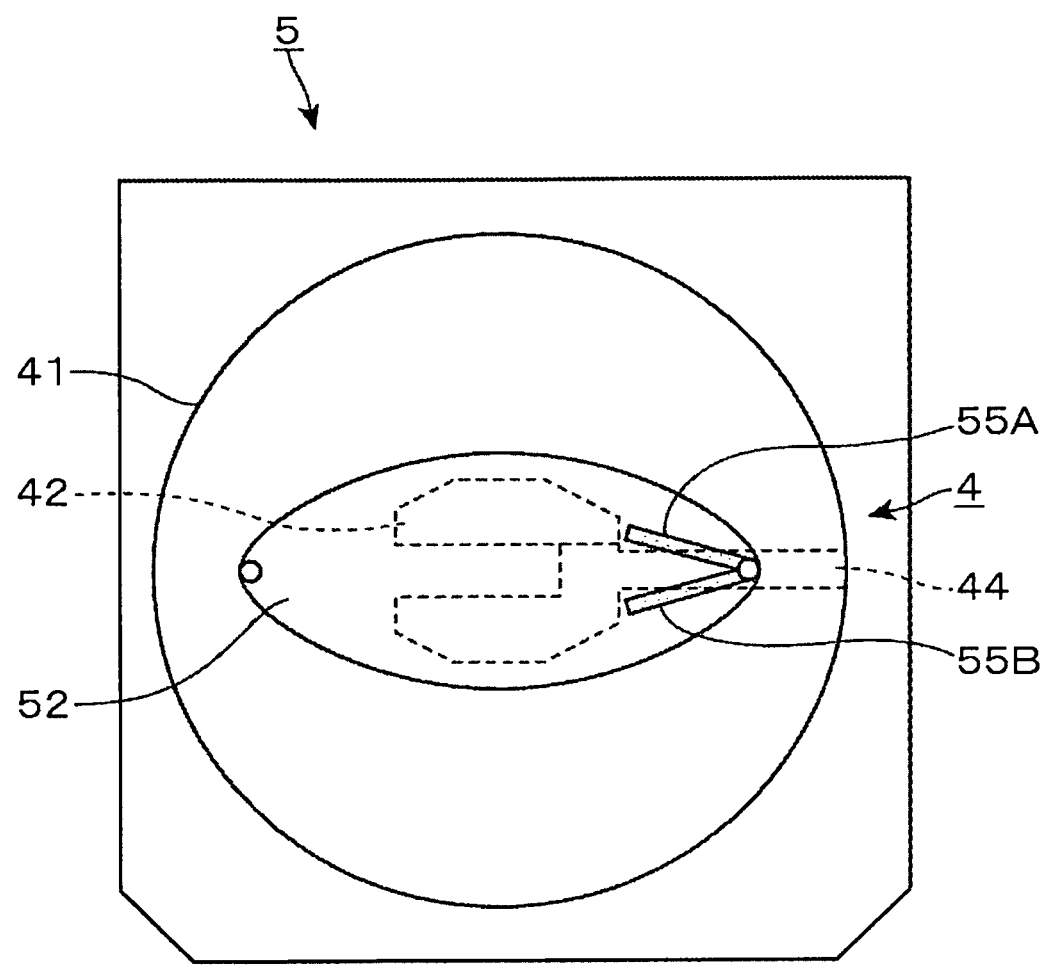
FIG. 12 is a plan view of a channel forming member showing an example of an another embodied shape regarding a concave portion.

In the aforementioned embodiment, the concave portion 52 has a shape of rhombus with curved corners, but, it may also have an elliptical shape as shown in FIG. 12, a rectangular shape or a square shape.

Figure 13:
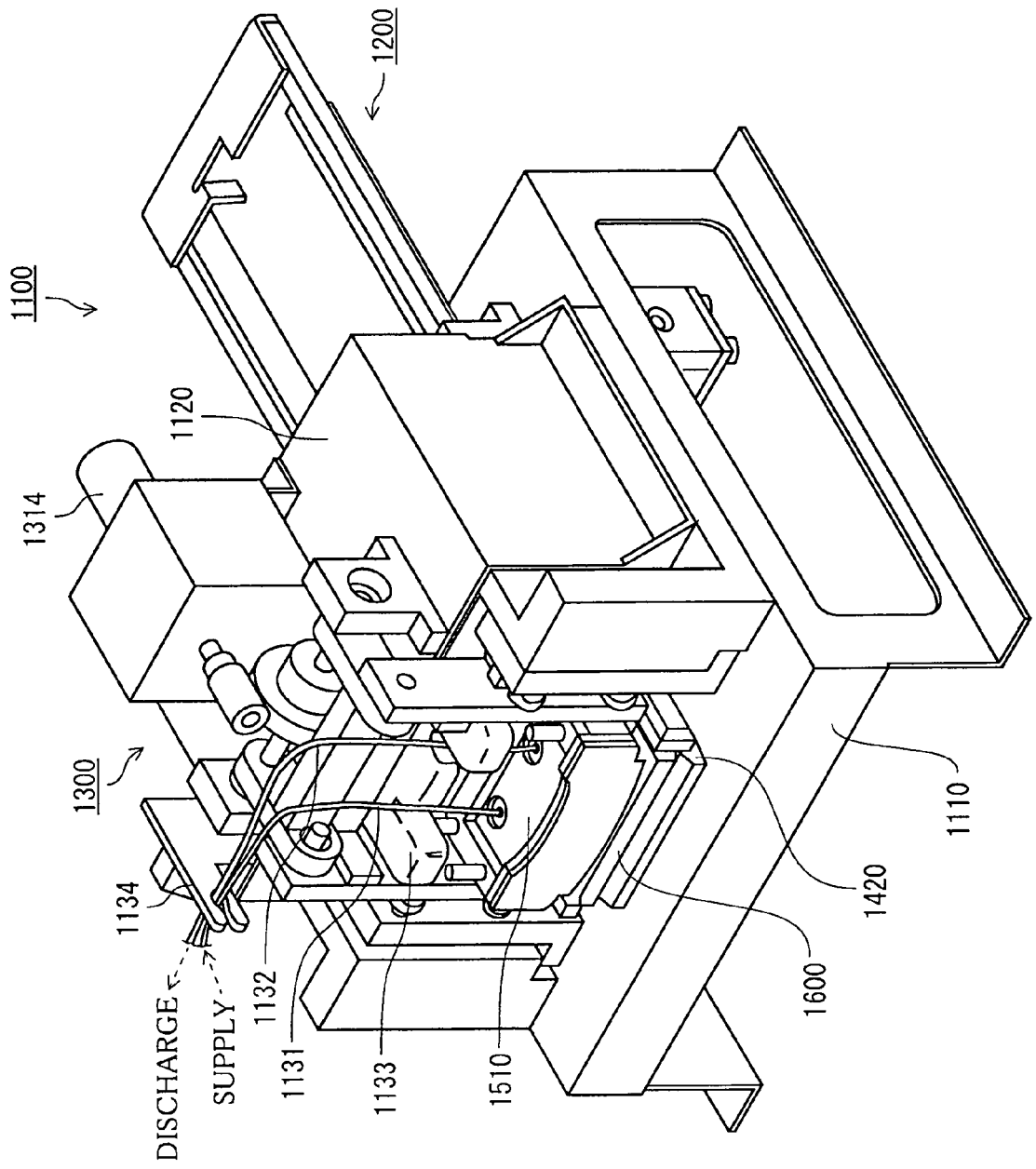
FIG. 13 is a perspective view showing an external appearance structure of a sensing device according to an embodiment of the present invention.
Figure 14:
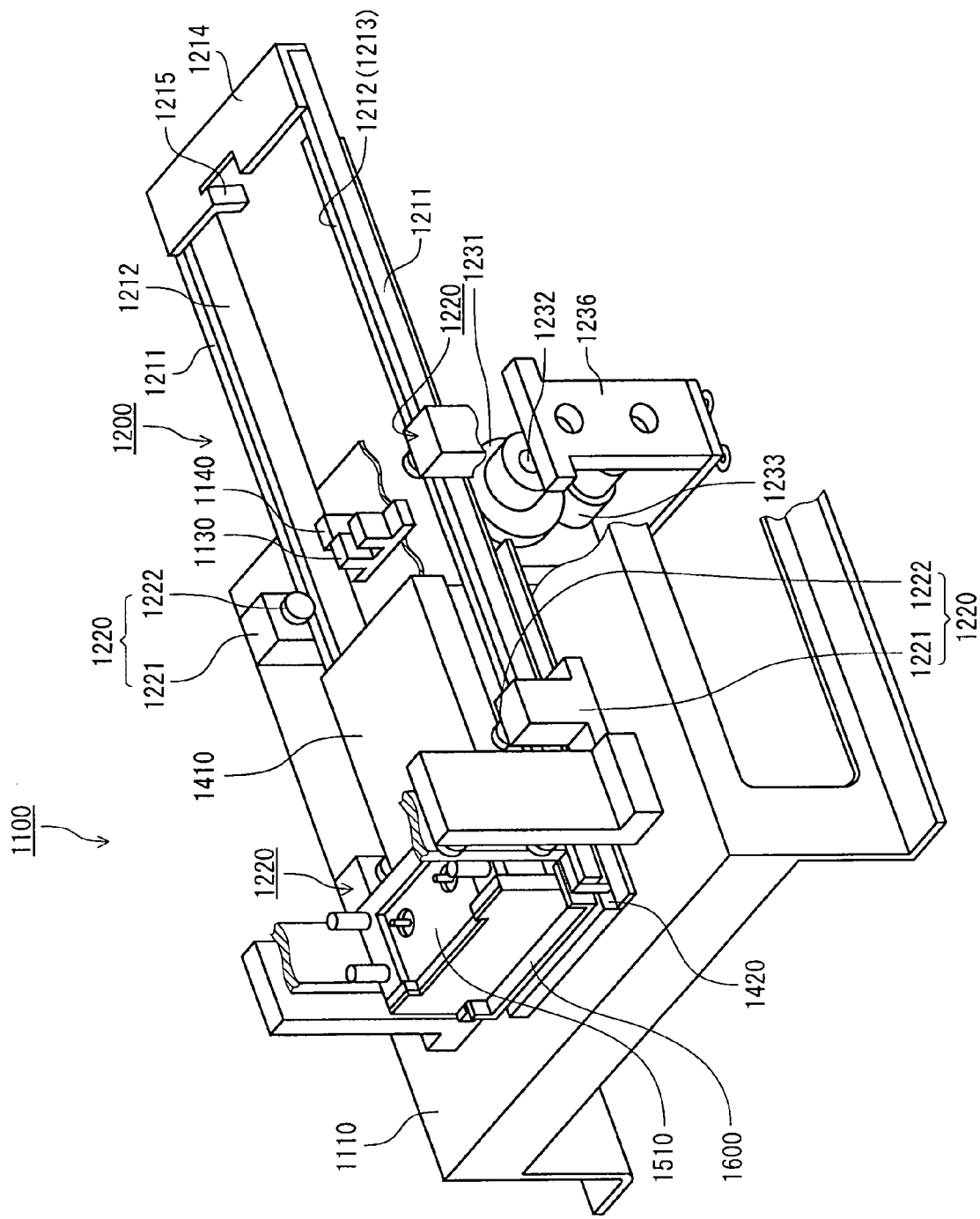
FIG. 14 is a perspective view showing an internal structure of the sensing device.

Hereinafter, explanation will be made on a structure of a sensing device 1100 including a mechanism to automatically mount the quartz-crystal sensor 7 (described as a piezoelectric sensor 1700, hereinafter) which is used in a state of being stacked with the aforementioned channel forming member 5, while referring to FIG. 13 to FIG. 27. As shown in FIG. 13 and FIG. 14, the sensing device 1100 includes: a chassis part 1410 being a measuring device main body that houses later-described oscillator circuit portions 1810a, 1810b oscillating the piezoelectric sensor 1700; a moving mechanism 1200 mounting a flow cell base 1600 being a holding member that detachably holds the piezoelectric sensor 1700 to arm members 1212 and moving the flow cell base forward and backward in a horizontal direction toward the chassis part 1410; a flow cell cover 1510 being not only a fixing member fixing the channel forming member 5 (described as a micro-channel chip 1730, hereinafter) or a rubber packing 1730a that forms, with the piezoelectric sensor 1700, a passage space of sample fluid (sample solution), by pressing it against a plate surface of the piezoelectric sensor 1700, but also a cover member placed on these members; and a raising/lowering mechanism 1300 raising/lowering the flow cell cover 1510, and these are disposed on a common base 1110. Hereinafter, in each of the drawings in FIG. 13 to FIG. 17, FIG. 21, FIGS. 28 to 29 and FIG. 33, explanation will be made by setting a left side and a right side in the drawing to a near side and a far side, respectively.

Figure 15:
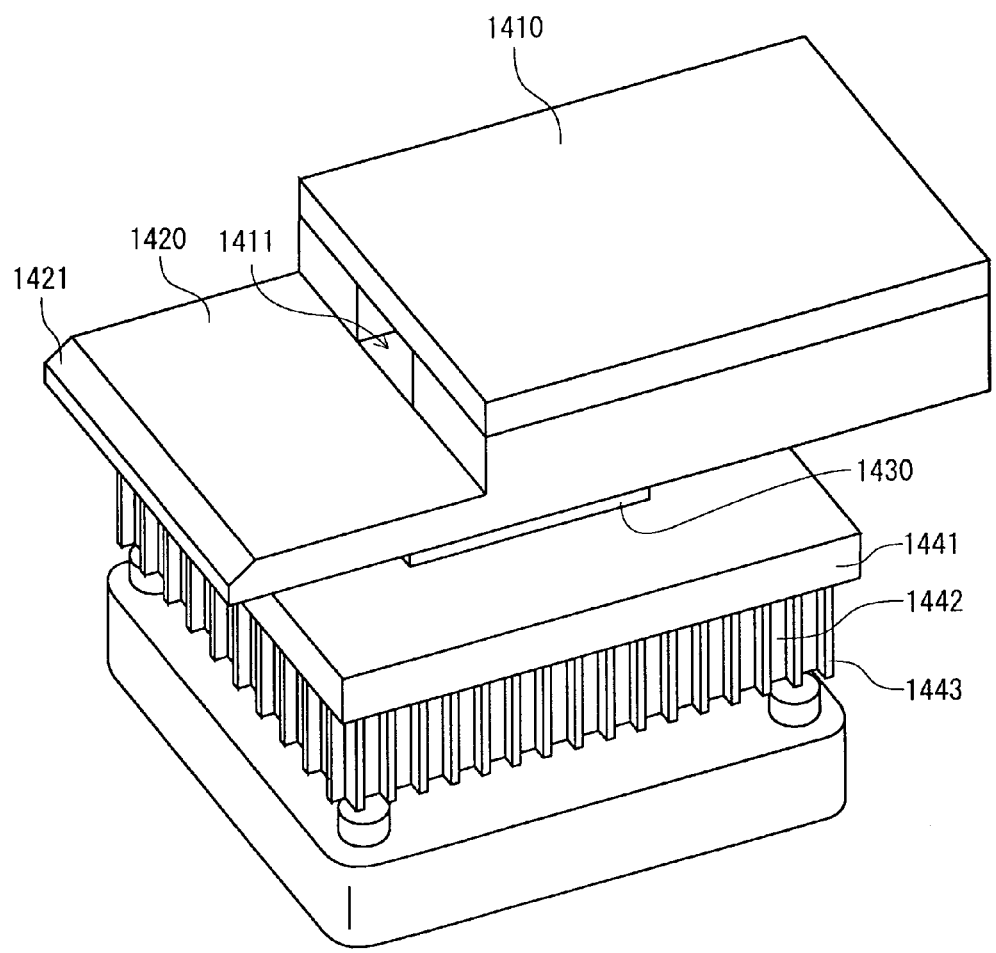
FIG. 15 is an external perspective view showing a chassis part provided to the sensing device.

FIG. 15 shows a state where the chassis part 1410 is removed from the base 1110, and the chassis part 1410 is structured as a casing made of metal. On a sidewall surface on the near side of the chassis part 1410, there is provided a connection port 1411 in which the piezoelectric sensor 1700 is to be inserted, and in the connection port 1411, there is disposed a terminal portion 1412 serving as a connecting part for connecting the piezoelectric sensor 1700 to the oscillator circuit portions 1810a, 1810b (refer to FIG. 26).

As shown in FIG. 15, on the near side of the connection port 1411, there is disposed a guide member 1420 made of a plate-shaped member that extends in a horizontal direction, starting from a lower end portion of the connection port 1411, toward the near side. The guide member 1420 has an upper surface that is processed to be flat, and the later-described flow cell base 1600 holding the piezoelectric sensor 1700 is designed to be moved toward the connection port 1411 in a state of being placed on the upper surface of the guide member 1420. Further, on an upper surface of a tip potion on the near side of the guide member 1420, there is provided a guide surface 1421 formed of an inclined surface formed to have an inclination gradually increasing from the near side to the far side.

In order to keep a temperature of the quartz-crystal resonator 1720 and a sample fluid that flows through the passage space constant, there is provided, under a lower surface of the chassis part 1410, a Peltier element 1430 serving as a temperature adjusting mechanism for adjusting a temperature of the chassis part 1410 and the guide member 1420 brought into contact with the piezoelectric sensor 1700 via the flow cell base 1600 and the like. The Peltier element 1430 is connected to a not-shown power supply part and a later-described control unit 1800, and by increasing/decreasing, with the use of a not-shown thermocouple, an electric power applied by the power supply part based on a result of detecting the temperature of the chassis part 1410 and the guide member 1420, an amount of heat absorption from a heat absorbing surface of the Peltier element 1430 is adjusted, resulting in that the temperature of the quartz-crystal resonator 1720 and the sample fluid can be kept constant via the chassis part 1410 and the guide member 1420.

In FIG. 15, 1442 denotes a radiator for radiating heat received from a radiating surface of the Peltier element 1430, and the radiator 1442 is provided with a large number of fins 1443 for increasing a heat radiation efficiency. Further, 1441 denotes a heat transfer plate that transfers heat to the radiator 1442 from the radiating surface of the Peltier element 1430.

Here, the temperature adjusting mechanism for keeping the temperature of the quartz-crystal resonator 1720 constant is not limited to the case of using the Peltier element 1430, and it is also possible to use a heating unit such as a tape heater, depending on a set temperature.

As shown in FIG. 14, the sensing device 1100 of the present example is designed to have the chassis part 1410 projecting on an upper surface side of the base 1110 and the heat transfer plate 1441 and the radiator 1442 positioned on a lower surface side of the base 1110. Further, as shown in FIG. 13, the chassis part 1410 is disposed in a cover 1120 that supports a rotation motor 1314 and the like of the raising/lowering mechanism 1300.

Figure 16:
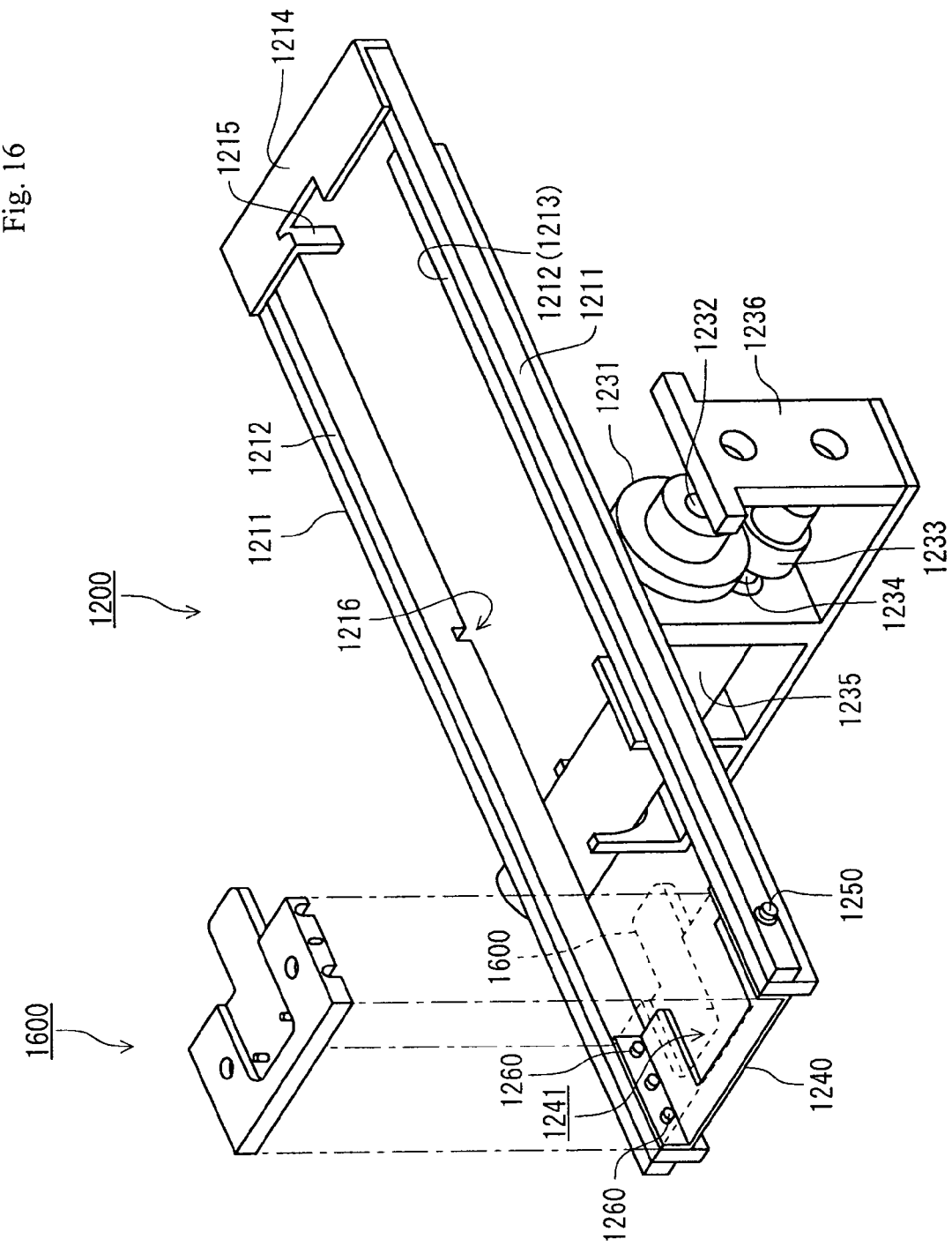
FIG. 16 is a perspective view showing structures of a flow cell base and a moving mechanism thereof provided to the sensing device.

Next, the moving mechanism 1200 will be explained. As shown in FIG. 14, if the chassis part 1410 disposed to project on the upper surface side of the base 1110 is seen from the near side, there are disposed, on both left and right sides of the chassis part, two arm members 1212 extending in forward and backward directions along both left and right sidewalls of the chassis part 1410. As shown in FIG. 16, these arm members 1212 are mutually coupled by a support plate 1240 provided at a tip position of the members on the near side and a coupling member 1214 provided at a rear end position on the far side. These arm members 1212 serve as a movable body to which the flow cell base 1600 holding the piezoelectric sensor 1700 is mounted, and the support plate 1240 coupling the two arm members 1212 at the tip position serves to support the flow cell base 1600 from the lower surface side, and details thereof will be described later together with a structure of the flow cell base 1600.

To the respective arms members 1212, there are mounted rail members 1211 on outer side surfaces thereof with the chassis part 1410 therebetween, and these rail members 1211 are designed to be able to move in forward and backward directions by being guided by guide parts 1220 disposed on the base 1110. The guide part 1220 includes a guide wheel 1222 that clips the rail member 1211 from upper and lower directions and guides the member while rotating in a moving direction of the rail member 1211, and a support member 1221 that supports the guide wheel 1222. As shown in FIG. 14, there are disposed two guide parts 1220 on the left, two guide parts 1220 on the right, in forward and backward directions along the moving direction of the rail members 1211 with the chassis part 1410 therebetween.

As shown in FIG. 16, under a lower surface of one side of the two arm members 1212, which is, for example, the arm member 1212 on the right side seen from the near side, there is formed a rack gear 1213, and the rack gear 1213 forms a pinion-rack mechanism by engaging with a pinion member 1231 disposed on the lower surface side of the base 1110. The pinion member 1231 further engages with a gear portion 1233 that is rotated by a rotation motor 1235, and by rotating the gear portion 1233, it is possible to move the arm members 1212 via the pinion member 1231.

Further, the rotation motor 1235 can switch a rotational direction of the gear portion 1233, which enables to switch the moving direction of the arm members 1212. In the drawing, 1232 denotes a rotation shaft of the pinion member 1231, 1234 denotes a rotation shaft of the gear portion 1233, and 1236 denotes a support table that supports these rotation shafts 1232, 1234 and the rotation motor 1235.

As shown in FIG. 16, to the coupling member 1214 coupling the two arm members 1212 at the rear end position, there is provided a projecting piece portion 1215 that extends downward. Meanwhile, on a substantially center portion of the arm member 1212 on the left side seen from the near side, there is provided a cut-out portion 1216 formed by cutting out a lower edge side of the arm member 1212. On the other hand, as shown in FIG. 14, there is disposed, on the base 1110, an infrared blocking-type sensor 1130 in an orbit of the projecting piece portion 1215 that moves in forward and backward directions in accordance with the movement of the arm members 1212, for example. Further, in a movement orbit of the arm member 1212 on the left side, an infrared transmission-type sensor 1140 is disposed, for example.

Further, when the projecting piece portion 1215 reaches the blocking-type sensor 1130 by making the arm members 1212 move forward from the far side to the near side, a conduction state of infrared ray is blocked by the projecting piece portion 1215. The change in the conduction state is output to the later-described control unit 1800, and when a stop signal is output from the control unit 1800 to the rotation motor 1235 based on the change in the state, the forward movement of the arm members 1212 can be stopped. At this time, a position at which the support plate 1240 provided to the tip of the arm members 1212 is stopped, corresponds to a holding position at which the piezoelectric sensor 1700 is held to the flow cell base 1600 supported on the support plate 1240.

Meanwhile, when the cut-out portion 1216 reaches the transmission-type sensor 1140 by making the arm members 1212 move backward from the near side to the far side, the infrared ray blocked by the arm member 1212 becomes in a conduction state. The change in the state is output to the later-described control unit 1800, and when a stop signal is output from the control unit 1800 to the rotation motor 1235 based on the change in the state, the backward movement of the arm members 1212 is stopped. At this time, the flow cell base 1600 supported on the support plate 1240 is stopped at a position below the flow cell cover 1510, and this position corresponds to a connecting position at which the piezoelectric sensor 1700 held to the flow cell base 1600 is connected to the oscillator circuit portions 1810*a*, 1810*b*.

Next, explanation will be made on a structure of the raising/lowering mechanism 1300 for raising/lowering the flow cell cover 1510, while referring to FIG. 17. As will be explained later in detail, the flow cell cover 1510 is structured as a member having a substantially rectangular parallelepiped shape, and is placed on an upper surface of the flow cell base 1600 that is moved to the connecting position. On both left and right sides of the flow cell cover 1510 seen from the near side, support members 1331 for raising/lowering the flow cell cover 1510 are provided so as to extend in a longitudinal direction, and on a lower end portion of each of the support members 1331, there is formed a chuck portion 1334 that is bent inward toward a direction of the flow cell cover 1510.

By placing the flow cell cover 1510 on the chuck portions 1334, the flow cell cover 1510 is supported to the support members 1331, and the flow cell cover 1510 can be raised/lowered in accordance with a raising/lowering operation of the support members 1331. As shown in FIG. 14, FIG. 17, FIG. 18 and the like, there are provided, to the support members 1331, spring plungers 1350 serving as a pressing part for pressing the flow cell cover 1510 toward the micro-channel chip 1730 disposed under the flow cell cover 1510. Here, FIG. 18 shows vertical sections of the flow cell cover 1510, the micro-channel chip 1730, the piezoelectric sensor 1700 and the flow cell base 1600.

Figure 17:
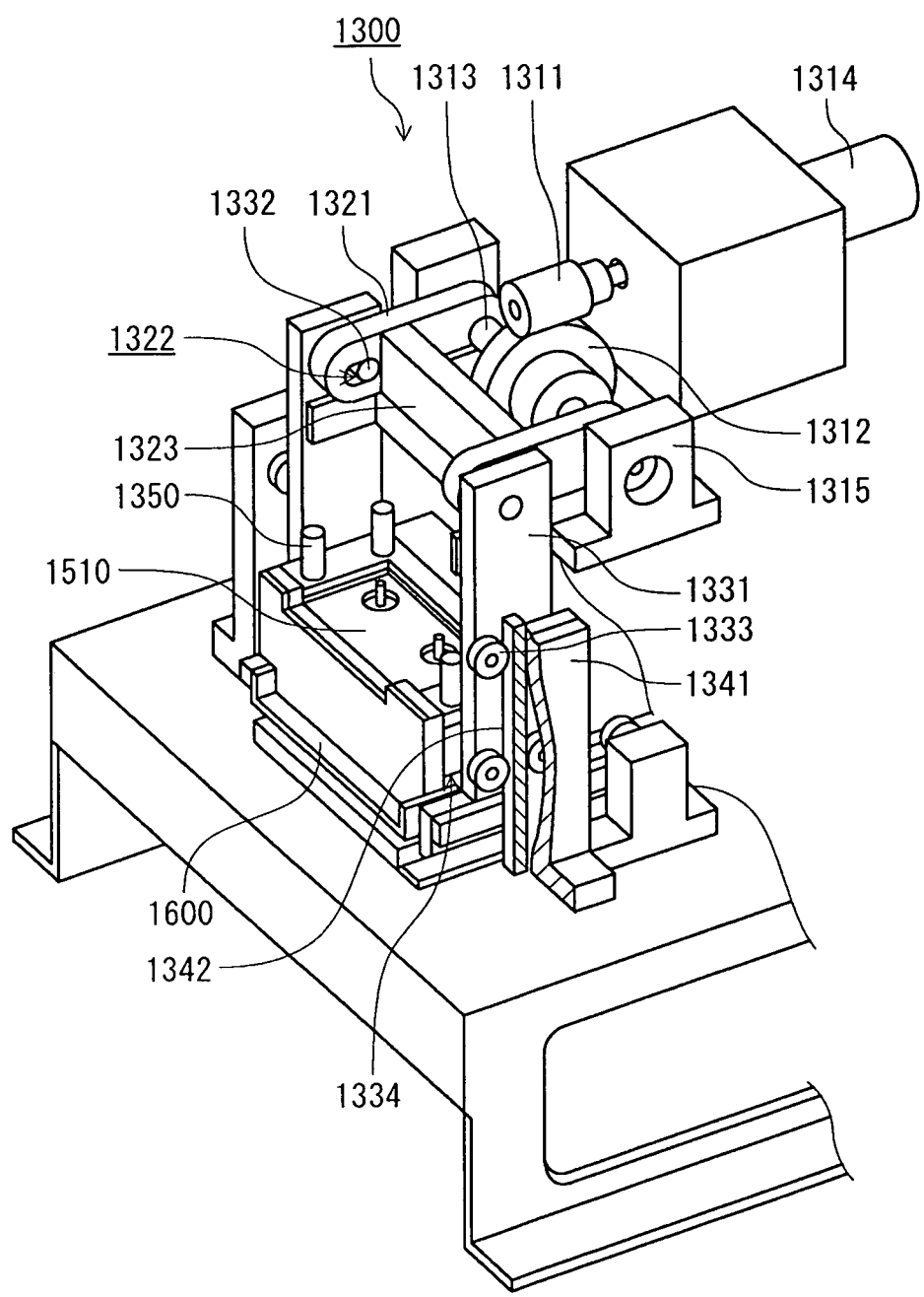
FIG. 17 is a partial cutaway perspective view showing a flow cell cover and a raising/lowering mechanism thereof provided to the sensing device.
Figure 18:
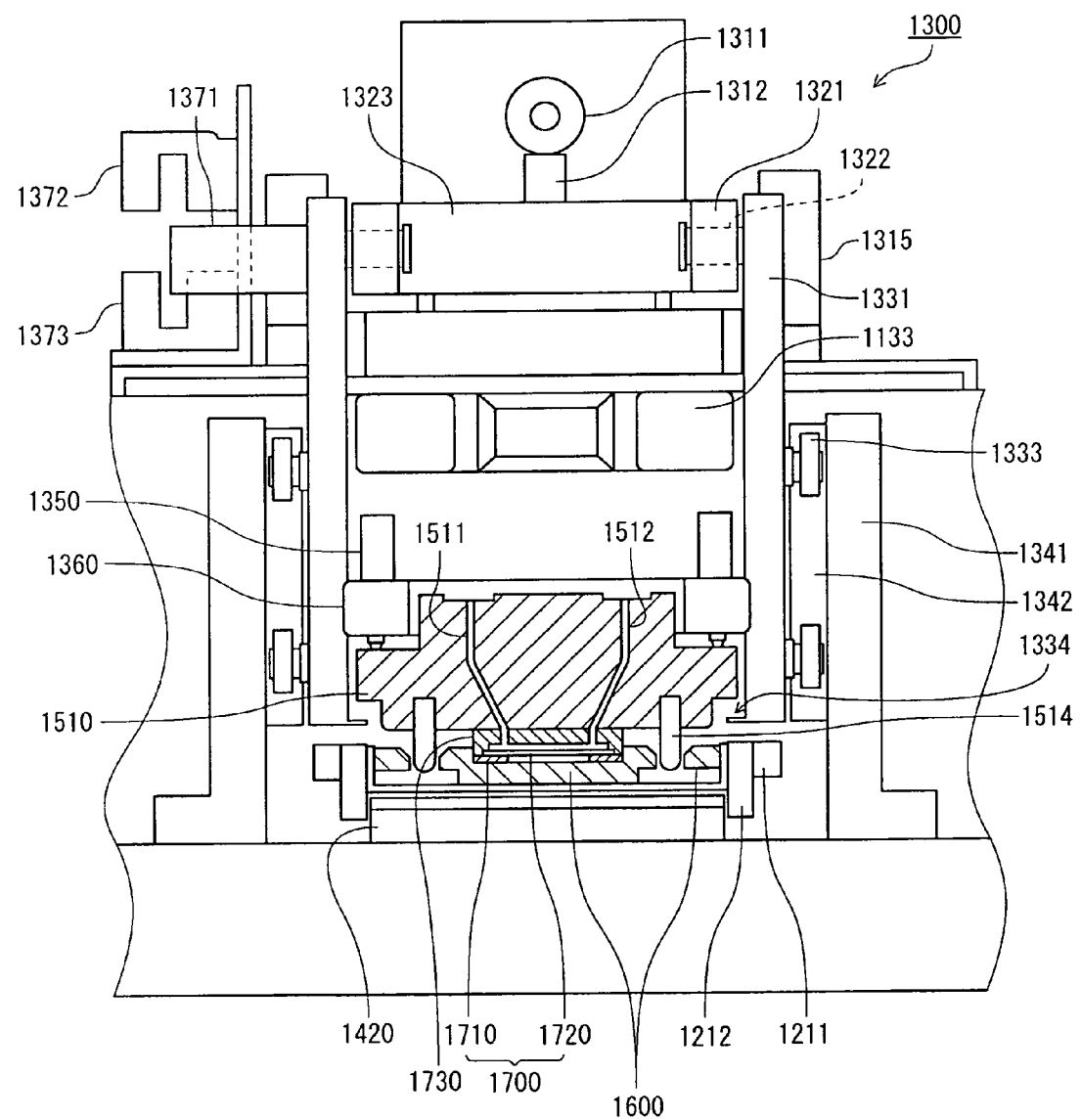
FIG. 18 is a partial vertical sectional side view showing the flow cell cover and the raising/lowering mechanism thereof.

As shown in FIG. 14 and FIG. 17, one spring plunger 1350 is provided on each of four corners of a holder 1360 that is formed to have a planar shape of U form. Further, by fixing the holder 1360 to the support members 1331 by directing the U-shaped cut-out portion to the near side, it is possible to press an upper surface of the flow cell cover 1510 with a uniform force by simultaneously raising/lowering these four spring plungers 1350 in a state where height positions of their lower end portions are aligned.

Figure 19:
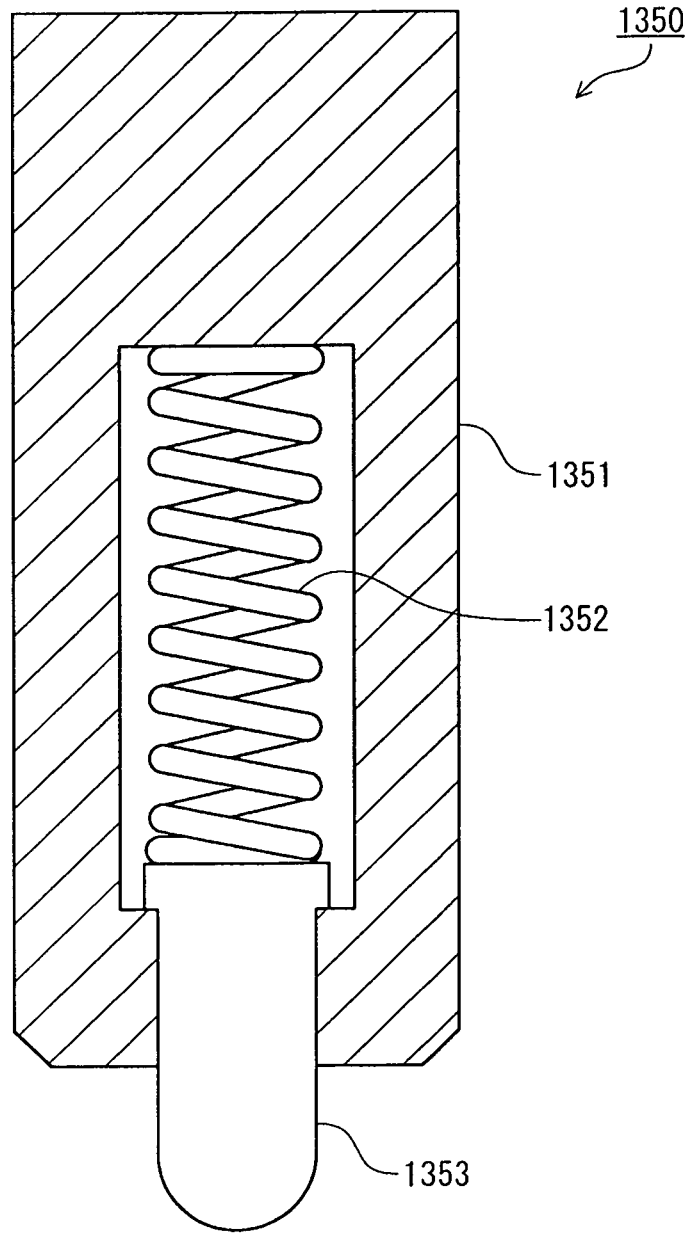
FIG. 19 is a vertical sectional side view showing a structure of a spring plunger that forms a pressing part of the flow cell cover.

As shown in FIG. 19, the spring plunger 1350 is structured to provide a spring member 1352 inside a cylindrical-shaped plunger main body 1351 whose lower end surface is opened, and provide, to a lower end portion of the spring member 1352, a column-shaped abutting member 1353 whose tip portion is round-processed in a hemispherical shape. The spring member is biased in a direction in which the abutting member 1353 is pushed out downward, and in a state where a load is not applied, the abutting member 1353 is in a state in which a lower half thereof projects from the opening portion of the plunger main body 1351, as shown in FIG. 19.

Further, within a moving range of the abutting member from a state where the lower end portion of the abutting member 1353 projects from the plunger main body 1351 to a state where the entire abutting member 1353 is housed inside the plunger main body 1351, the abutting member 1353 can press the flow cell cover 1510 downward with a constant force in accordance with a spring constant of the spring member 1352.

Further, as shown in FIG. 18, a distance between an upper surface of the chuck portion 1334 supporting the flow cell cover 1510 from the lower surface side and the lower end portion of the spring plunger 1350 pressing the flow cell cover 1510 from the upper surface side is greater than a distance between the upper and lower surfaces of the flow cell cover 1510 brought into contact with these chuck portion 1334 and spring plunger 1350. For this reason, as shown in FIG. 18, when the flow cell cover 1510 is placed on the micro-channel chip 1730, the chuck portions 1334 separate from the flow cell cover 1510 to move downward, which creates a state where the spring plungers 1350 press the flow cell cover 1510 from the upper surface side, changed from a state where the chuck portions 1334 support the flow cell cover. As a result of this, almost all of the force of the spring plungers 1350 to press the flow cell cover 1510 is utilized as a force with which the micro-channel chip 1730 is closely contacted to the piezoelectric sensor 1700.

Returning to the explanation of the entire raising/lowering mechanism 1300, on an upper end portion of each of the support members 1331, there is provided a crankshaft 1332, and the crankshaft 1332 is inserted in a bearing hole 1322 of an arm member 1321. The arm member 1321 extends to the far side from a position at which the crankshaft 1332 is provided, and is connected to a rotation shaft 1313 at its rear end portion. The rotation shaft 1313 extends in a horizontal direction so as to penetrate the two arm members 1321, and the arm members 1321 are disposed on both left and right end portions of the rotation shaft 1313.

Further, to the rotation shaft 1313, there is provided a worm wheel 1312 at an intermediate position sandwiched by the arm members 1321 disposed on both the left and right end portions. A worm 1311 is engaged with the worm wheel 1312, and these worm 1311 and worm wheel 1312 structure a worm gear mechanism. The worm 1311 is rotary-driven by the rotation motor 1314, and the worm wheel 1312 engaged with the worm 1311 is rotated by the rotation of the worm 1311, resulting in that the arm members 1321 coupled to the worm wheel 1312 via the rotation shaft 1313 are rotated around the rotation shaft 1313. Further, the rotation operation of the arm members 1321 is converted into the raising/lowering operation of the support members 1331 via the crankshafts 1332, which enables to raise/lower the flow cell cover 1510 supported by the support members 1331 between a fixing position on the flow cell base 1600 (piezoelectric sensor 1700) and a retreat position retreating upward from the fixing position.

Further, in parallel with the raising/lowering operation of the flow cell cover 1510, the support members 1331 also serve to raise/lower the spring plungers 1350 between a pressing position at which the flow cell cover 1510 is pressed and a release position retreating upward from the pressing position and at which the flow cell cover 1510 is released from the pressed state. From a viewpoint described above, it can be said that the raising/lowering mechanism 1300 realizes both a function as a first raising/lowering mechanism for raising/lowering the spring plungers 1350 and a function as a second raising/lowering mechanism for raising/lowering the flow cell cover 1510.

Here, the bearing hole 1322 provided to the arm member 1321 and through which the crankshaft 1332 is penetrated, is formed to be elongated in a radial direction of a circle formed with the rotation shaft 1313 as its center. Accordingly, it is designed such that, when converting the rotation operation of the arm members 1321 into the raising/lowering operation of the support members 1331, the crankshafts 1332 can freely move within the bearing holes 1322 without interfering with the bearing holes 1322.

Further, 1323 in the drawing denotes a coupling member coupling the left and right arm members 1321. To the raising/lowering mechanism 1300, there is also provided a not-shown stop mechanism that stops the driving of the rotation motor 1314 after raising/lowering the flow cell cover 1510 to a previously set height position, similar to the blocking-type sensor 1130 and the projecting piece portion 1215, and the transmission-type sensor 1140 and the cut-out portion 1216 in the moving mechanism 1200 shown in FIG. 14.

Further, in FIG. 17, components denoted by 1342 are guide rails being disposed to extend in a longitudinal direction at positions of left and right lateral sides of the respective support members 1331 and guiding an orbit along which the support members 1331 are raised/lowered, and components denoted by 1341 are support post members fixing the guide rails 1342 onto the base 1110. Further, on a surface of each of the support members 1331 opposing the support post member 1341, traveling wheels 1333 are provided so as to clip the guide rails 1342 from both forward and backward sides, and when these traveling wheels 1333 travel while rotating along the guide rails 1342 at the time of the raising/lowering operation of the support members 1331, the raising/lowering direction of the support members 1331 is guided.

Figure 20:
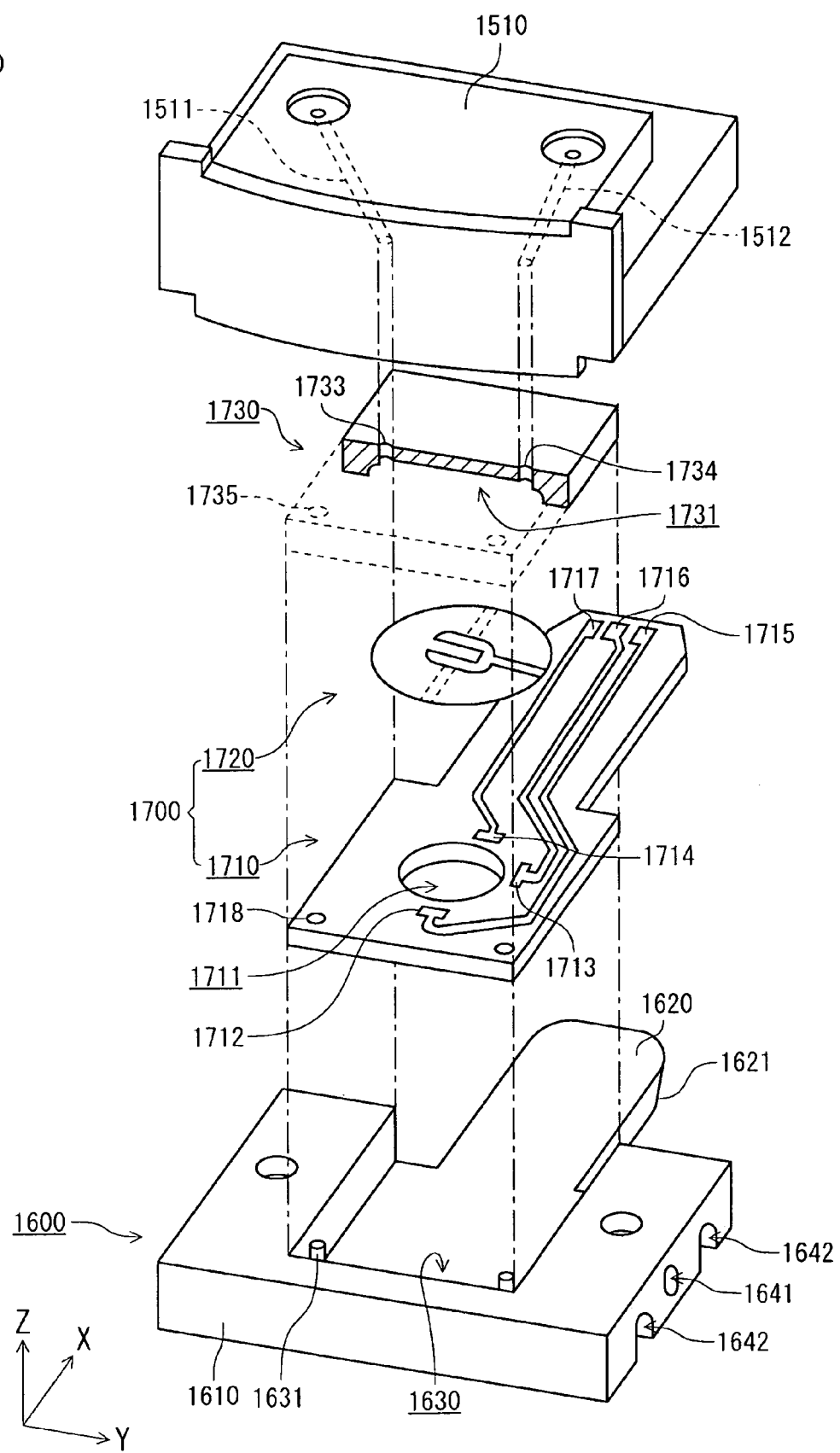
FIG. 20 is an exploded perspective view showing a structural example of the flow cell base, the flow cell cover and a piezoelectric sensor mounted therebetween.

Next, explanation will be made on each structure of the piezoelectric sensor 1700, the flow cell base 1600 that holds the piezoelectric sensor 1700, the micro-channel chip 1730 that forms the passage space of sample fluid with the piezoelectric sensor 1700, and the flow cell cover 1510 that fixes the micro-channel chip 1730 by pressing it against a plate surface of the piezoelectric sensor 1700, while referring to FIG. 20 to FIG. 24. FIG. 20 illustrates, in an order from the bottom, the flow cell base 1600, the piezoelectric sensor 1700, the quartz-crystal resonator 1720 and the flow cell cover 1510.

Figure 21:
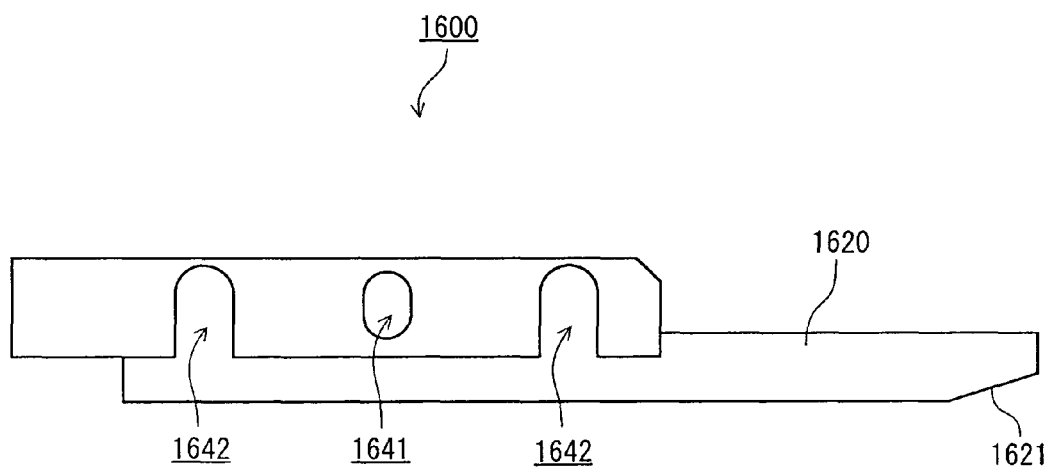
FIG. 21 is a side view of the flow cell base.

The flow cell base 1600 is structured from a square plate-shaped small piece made of metal or the like, and is formed to have a size capable of being disposed on an upper surface of the support plate 1240 provided at the tip portion of the two arm members 1212. The flow cell base 1600 is structured from a base main body portion 1610 and a projecting piece portion 1620, and on the base main body portion 1610, there is formed a concave portion 1630 for disposing the piezoelectric sensor 1700. The projecting piece portion 1620 is formed to project in a lateral direction from the concave portion 1630, and on the projecting piece portion 1620, a rear portion of the piezoelectric sensor 1700 is placed (FIG. 20, FIG. 21). On a lower surface of the projecting piece portion 1620, there is formed a surface to be guided 1621 formed of an inclined surface whose inclination gradually increases toward a direction in which the projecting piece portion 1620 is projected (corresponding to a direction extending from the near side to the far side when the flow cell base 1600 is mounted to the raising/lowering mechanism 1300).

As shown in FIG. 20 and FIG. 21, on side surfaces of the base main body portion 1610, there are formed mounting screw holes 1641 for mounting the flow cell base 1600 to the arm members 1212. Further, as shown in FIG. 16, by disposing the flow cell base 1600 on the support plate 1240 while making the projecting piece portion 1620 face toward the far side and inserting mounting screws 1250 in the mounting screw holes 1641 from the arm members 1212 sides, the flow cell base 1600 is mounted to the moving mechanism 1200. As shown in FIG. 21, the mounting screw hole 1641 is formed in a long hole shape elongated in a longitudinal direction, and by inserting the mounting screws 1250 in the long holes, the flow cell base 1600 is mounted to the moving mechanism 1200 with an allowance with which it can move in the longitudinal direction.

On a sidewall surface of the base main body portion 1610, cut-out portions 1642 cutting out the sidewall surface toward a lower surface side are formed at positions on the near side and the far side so as to sandwich the aforementioned mounting screw hole 1641. Meanwhile, as shown in FIG. 16, projecting portions 1260 projecting toward these cut-out portions 1642 are provided on an internal surface of the support plate 1240 mounted to the arm members 1212, and these projecting portions 1260 are inserted in the cut-out portions 1642.

Here, these projecting portions 1260 are disposed at a height position slightly lower than that of the mounting screw 1250, and further, the support plate 1240 supporting the flow cell base 1600 has a portion on the far side that is cut out squarely, as shown in FIG. 16. According to these structures, when the flow cell base 1600 is mounted to the arm members 1212 using the mounting screws 1250, the flow cell base 1600 in which the projecting piece portion 1620 side is heavy rotates around the mounting screws 1250 in a direction in which the projecting piece portion 1620 is provided. However, since the projecting portions 1260 are provided on the far side of the mounting screws 1250, the rotation of the flow cell base 1600 is restricted at a position at which the projecting portions 1260 are brought into contact with upper ends of the cut-out portions 1642, resulting in that the flow cell base is stopped in a state of inclining toward the far side, as shown in FIG. 28(*a*).

Further, on a bottom surface of the flow cell base 1600, there is provided an area projecting downward by corresponding to the cut-out of the support plate 1240, and further, the flow cell base 1600 is mounted to the arm members 1212 with an allowance with which it can move in the longitudinal direction, as described above. According to these structures, when the projecting piece portion 1620 side is lifted to make the flow cell base 1600 to be in a horizontal state, a lower surface of the flow cell base 1600 becomes in a state of projecting from the cut-out of the support plate 1240, and the flow cell base 1600 can be in a state of being placed on the guide member 1420.

Further, in FIG. 20, components denoted by 1631 disposed in the concave portion 1630 of the flow cell base 1600 are positioning pins for positioning the piezoelectric sensor 1700 and the micro-channel chip 1730.

Figure 22A:
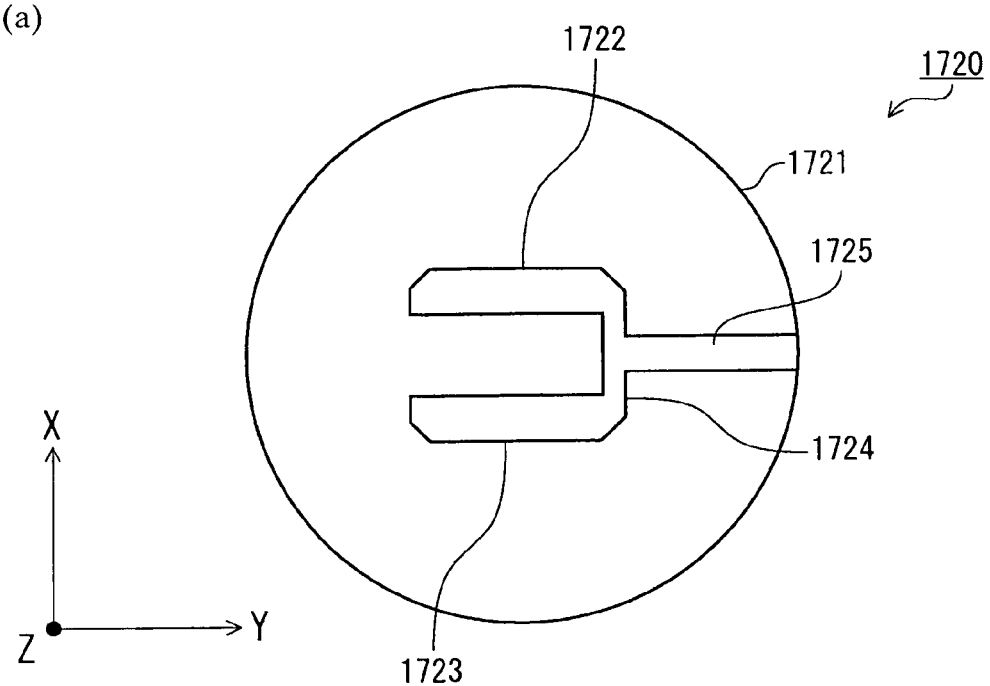
FIGS. 22(a) and 22(b) are explanatory diagrams showing a structural example of a piezoelectric resonator provided to the piezoelectric sensor.
Figure 22B:
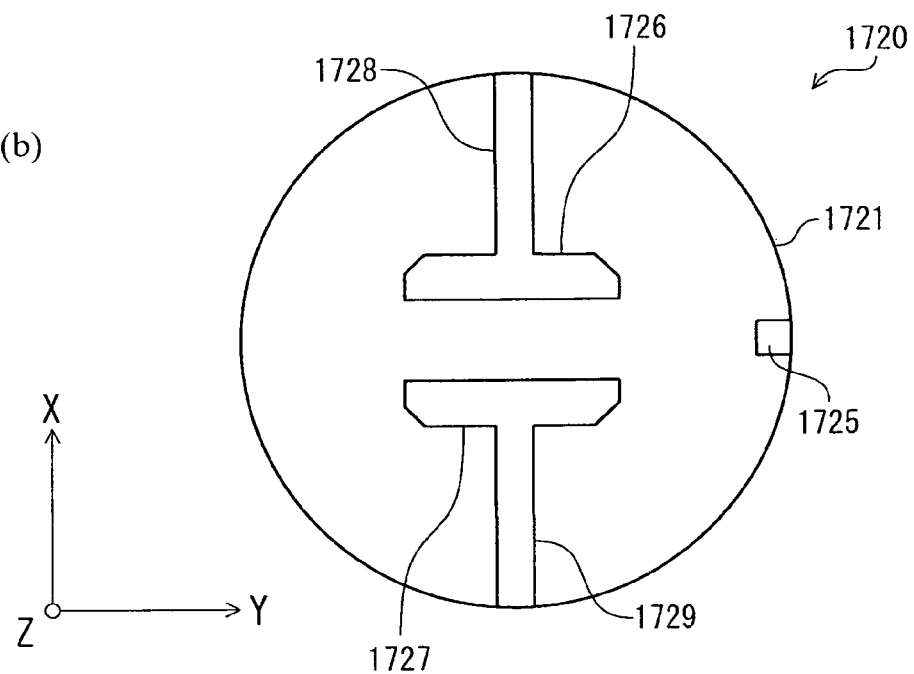

The piezoelectric sensor 1700 is structured by disposing the quartz-crystal resonator 1720 on a wiring board 1710, and as shown in FIG. 22, the quartz-crystal resonator 1720 is formed by providing, on center portions of both front and rear surfaces of a quartz-crystal piece 1721 in a disk shape being a piezoelectric piece, excitation electrodes 1722, 1723, 1726, 1727 for exciting the quartz-crystal piece 1721. FIG. 22(*a*) is a plan view in which the front surface of the quartz-crystal resonator 1720 is seen from an upper surface side, and on the quartz-crystal piece 1721, strip-shaped two excitation electrodes 1722, 1723 extending in a Y direction (corresponding to the left and right lateral direction when the sensing device 1100 is seen from the near side) are disposed in parallel to each other with a space therebetween. These two excitation electrodes 1722, 1723 are mutually connected by a connecting line 1724, and from the connecting line 1724, a lead-out electrode 1725 is led out toward the same direction as a longitudinal direction of the excitation electrodes 1722, 1723, and the lead-out electrode 1725 extends toward the rear surface side of the quartz-crystal piece 1721.

FIG. 22(*b*) is a plan view in which the rear surface of the quartz-crystal resonator 1720 is seen from a lower surface side, and there are disposed strip-shaped excitation electrodes 1726, 1727 at positions opposing the respective excitation electrodes 1722, 1723 on the front surface side, respectively. From the respective excitation electrodes 1726, 1727, lead-out electrodes 1728, 1729 are led out in directions opposite to each other, toward directions orthogonal to these excitation electrodes 1726, 1727.

Figure 23:
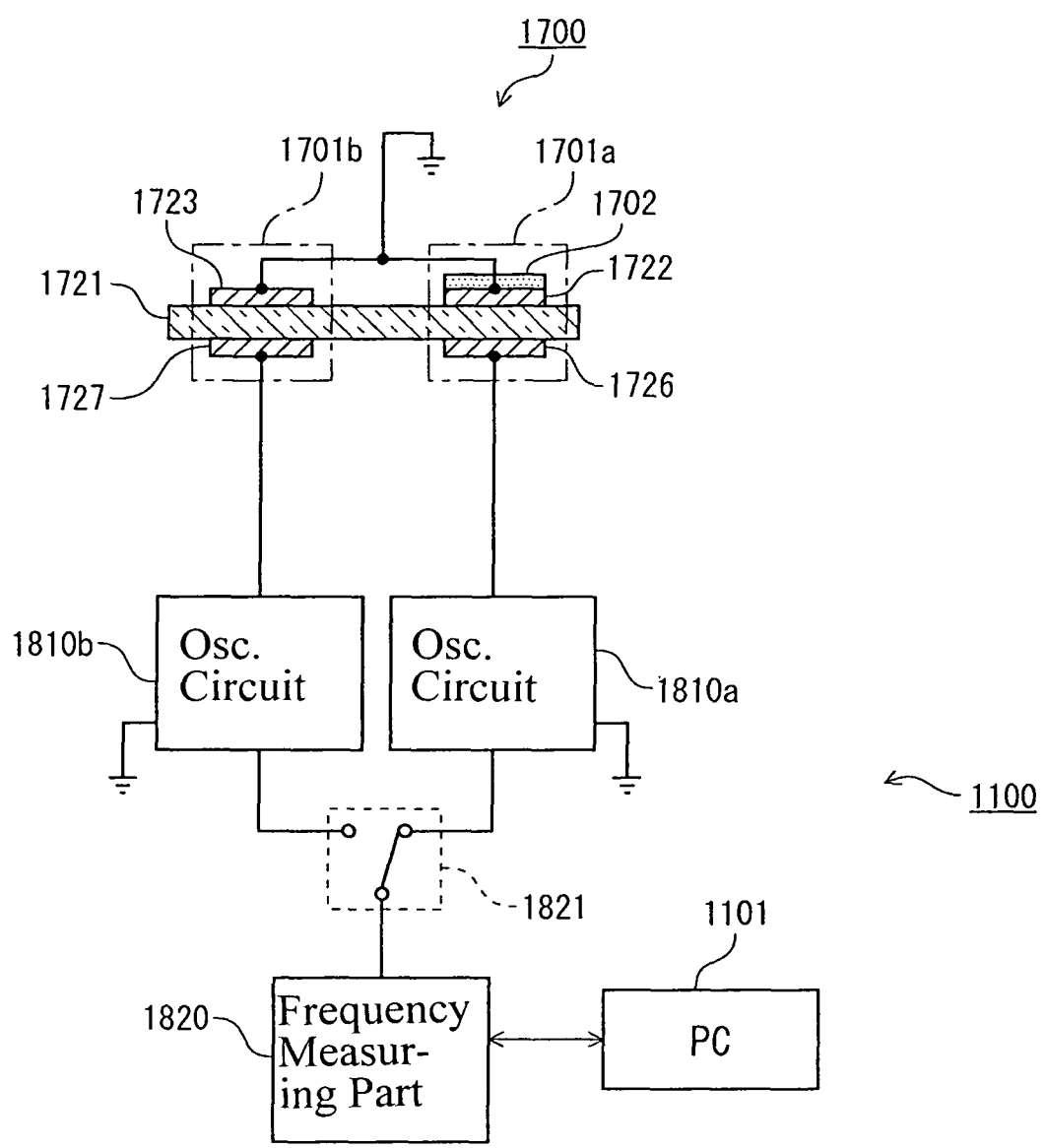
FIG. 23 is an explanatory diagram showing a state where the piezoelectric resonator is connected to oscillator circuits.

As shown in FIG. 23, the vertically opposing excitation electrodes 1722, 1726 on one side and the quartz-crystal piece 1721 sandwiched therebetween form a first oscillation area 1701*a*, and the excitation electrodes 1723, 1727 on the other side and the quartz-crystal piece 1721 sandwiched therebetween form a second oscillation area 1701*b*. Further, these oscillation areas 1701*a*, 1701*b* are mutually elastically insulated, and each of the oscillation areas 1701*a*, 1701*b* operates as an independent quartz-crystal resonator. Further, for example, an absorption layer 1702 for absorbing a substance to be sensed is formed on the excitation electrode 1722 on a front surface side of the first oscillation area 1701*a*, and meanwhile, the second oscillation area 1701*b* is not provided with the absorption layer 1702 and is used as a reference electrode. Further, by obtaining a difference between an oscillation frequency of the first oscillation area 1701*a* in which the substance to be sensed is absorbed and an oscillation frequency of the second oscillation area 1701*b* in which the substance to be sensed is not absorbed, an influence of variation in the frequency caused by a change in viscosity of a sample fluid or an adhesion of substance other than the substance to be sensed is subtracted, resulting in that a variation in the oscillation frequency (decrease in the oscillation frequency) caused only by the absorption of the substance to be sensed in the absorption layer 1702 can be detected. In the piezoelectric sensor 1700 of the present example, the quartz-crystal resonator 1720 is disposed on the wiring board 1710 so that a front surface of the quartz-crystal piece 1721 on which the absorption layer 1702 is formed (referred to as an absorption surface) in the first oscillation area 1701*a* faces the upper surface.

The quartz-crystal resonator 1720 shown in FIGS. 22(*a*) and 22(*b*) corresponds to the quartz-crystal resonator 4 shown in FIGS. 4(*a*) and 4(*b*).

As shown in FIG. 20, the wiring board 1710 is a printed-circuit board whose front portion to be disposed in the concave portion 1630 of the flow cell base 1600 is processed to have a shape of placard with a width wider than that of a rear portion thereof to be similarly disposed on the projecting piece portion 1620 of the flow cell base 1600, and on the front portion, there is formed a through hole 1711 for securing free oscillation of the quartz-crystal resonator 1720. The quartz-crystal resonator 1720 is fixed onto the wiring board 1710 so as to cover the through hole 1711, and the respective excitation electrodes 1722, 1726, 1723, 1727 are disposed inside a contour of the through hole 1711.

In a periphery of the through hole 1711, electrode portions 1712 to 1714 to be connected to the respective lead-out electrodes 1725, 1728, 1729 led out to the rear surface side of the quartz-crystal resonator 1720, are disposed with a space therebetween. In the present example, the electrode portion 1712 disposed on the near side of the front portion of the wiring board 1710 is connected to the lead-out electrode 1728 of the excitation electrode 1726 on the rear surface side of the quartz-crystal resonator 1720, and the electrode portion 1714 disposed on the far side is similarly connected to the lead-out electrode 1729 of the excitation electrode 1727 on the rear surface side of the quartz-crystal resonator 1720. Further, the electrode portion 1713 disposed at an intermediate position between these two electrode portions 1712 and 1714 is connected to the lead-out electrode 1725 connected to the excitation electrodes 1722, 1723 on the front surface and led out to the rear surface side.

The respective electrode portions 1712 to 1714 are led out toward the far side of the wiring board 1710, and on a rear end portion of the wiring board 1710, there are formed terminal portions 1715 to 1717 connected to these electrode portions 1712 to 1714. Further, by inserting the rear end portion of the wiring board 1710 provided with these terminal portions 1715 to 1717 in the connection port 1411 of the chassis part 1410, the piezoelectric sensor 1700 is connected to the sensing device 1100. The terminal portions 1715 to 1717 correspond to terminals to be connected of the present embodiment. Further, components denoted by 1718 formed on the wiring board 1710 are positioning holes for fixing and positioning the piezoelectric sensor 1700 by inserting the positioning pins 1631 on the flow cell base 1600 side in the holes.

Here, explanation will be made on an electrical structure of the sensing device 1100 in a state where the piezoelectric sensor 1700 is connected, while referring to a block diagram shown in FIG. 23. The respective terminal portions 1715 to 1717 of the wiring board 1710 inserted in the connection port 1411 are connected to the terminal portion 1412 on the chassis part 1410 side, and accordingly, in the present example, the excitation electrode 1726 on the rear surface side of the first oscillation area 1701a is connected to a first oscillator circuit portion 1810a, and the excitation electrode 1727 on the rear surface side of the second oscillation area 1701b is connected to a second oscillator circuit portion 1810b. Further, the excitation electrodes 1722, 1723 on the front surface side of both the oscillation areas 1701a, 1701b are grounded.

The first oscillator circuit portion 1810a has a structure in which it is connected to the first oscillation area 1701a to form an oscillator circuit such as a Colpitts circuit, and can take out an oscillation frequency from the first oscillation area 1701a operating as an independent quartz-crystal resonator. Further, in like manner, the second oscillator circuit portion 1810b also forms an oscillator circuit by being connected to the second oscillation area 1701b, and can take out an oscillation frequency of the second oscillation area 1701b. These oscillator circuit portions 1810a, 1810b are connected to a frequency measuring part 1820 via a changeover switch part 1821, and the frequency measuring part 1820 can obtain a frequency signal time-divided by the changeover switch part 1821.

Further, by dividing one second into n (n is an even number), for example, and sequentially obtaining an oscillation frequency of each channel through processing in 1/n seconds, although, strictly speaking, the measurement is not conducted completely at the same time, a frequency signal is obtained at least one time or more during one second, so that it becomes possible to obtain the oscillation frequencies of the respective oscillation areas 1701a, 1701b in a substantially parallel manner.

The oscillation frequencies of the respective oscillation areas 1701a, 1701b obtained by the frequency measuring part 1820 are output to an analyzer such as a personal computer 1101. In the analyzer, by obtaining a difference between the oscillation frequency of the first oscillation area 1701a and that of the second oscillation area 1701b, the influence of variation in the frequency caused by the change in viscosity of the sample fluid or the adhesion of substance other than the substance to be sensed is removed. By measuring, after that, the oscillation frequencies before and after the supply of the sample fluid, it is possible to obtain a variation amount of the oscillation frequency caused only by the absorption of the substance to be sensed. It becomes possible to form a calibration curve representing a correspondence between a concentration of the substance to be sensed in the sample fluid and an amount of decrease in the oscillation frequency based on the variation amount, and further, it becomes possible to determine the concentration of the substance to be sensed in the sample fluid or detect the presence/absence of the substance to be sensed by comparing the calibration curve with a previously formed calibration curve.

Returning to the explanation of FIG. 20, on an upper surface of the piezoelectric sensor 1700 held to the flow cell base 1600, the micro-channel chip 1730 forming a channel forming member of the present embodiment is placed. The micro-channel chip 1730 is made of an elastic material of a silicon rubber such as PDMS (polydimethylsiloxane) or the like, and a size thereof in the longitudinal direction and horizontal direction matches a size of the front portion of the piezoelectric sensor 1700, so that the micro-channel chip 1730 can be disposed in the concave portion 1630 of the flow cell base 1600 in a state of being placed on the piezoelectric sensor 1700.

Figure 24:
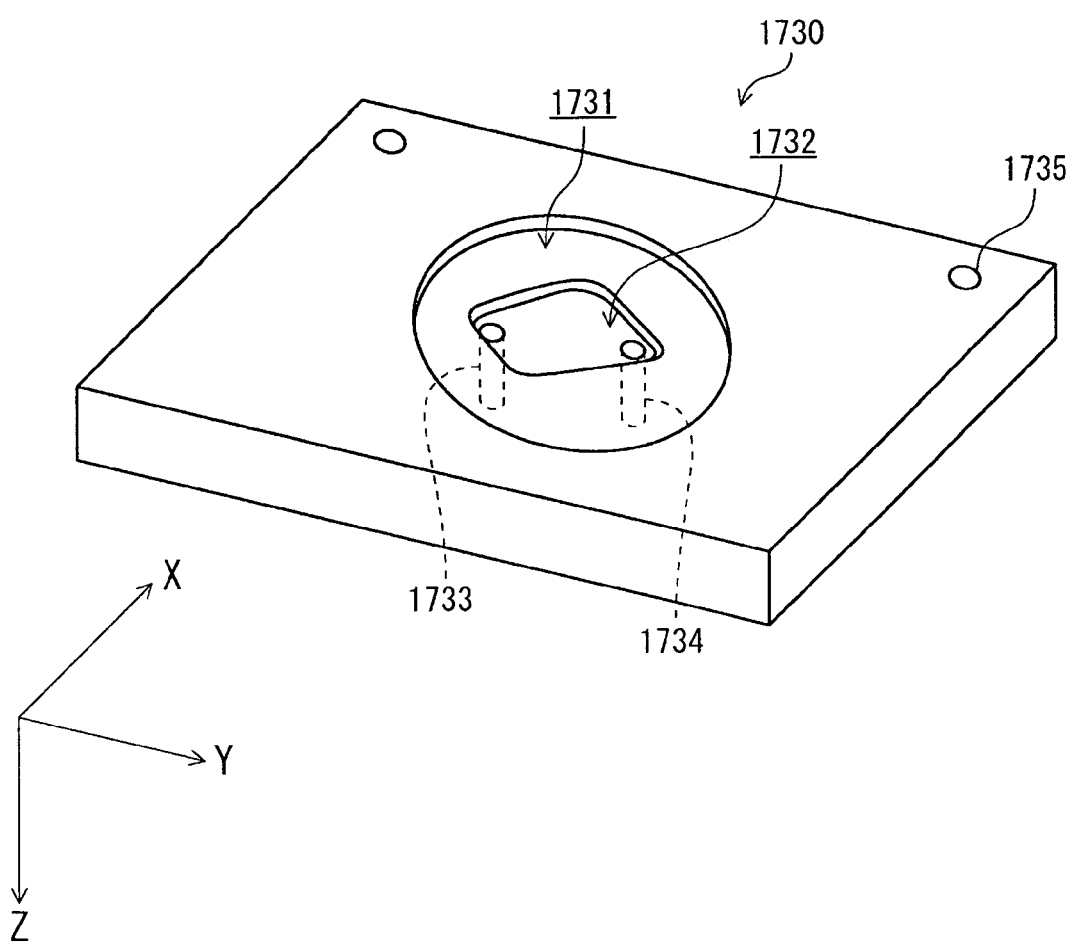
FIG. 24 is a perspective view showing an external appearance structure of a micro-channel chip for forming a passage space of sample fluid between the piezoelectric sensor and the flow cell cover.

The micro-channel chip 1730 is processed in a flake form with a thickness of several mm, and on its lower surface, there is formed a concave portion 1731 as shown in FIG. 24, and by making the quartz-crystal resonator 1720 disposed on the wiring board 1710 fitted in the concave portion 1731, it is possible to seal an upper surface (front surface) of the quartz-crystal resonator 1720. Further, within the concave portion 1731, there is formed a concave portion 1732 through which the sample fluid passes (referred to as a concave portion for passage, hereinafter) which is formed to have a depth of about sub-millimeters to 1 mm. By disposing the micro-channel chip 1730 provided with the concave portion for passage 1732 on the piezoelectric sensor 1700, a passage space (reaction channel) through which the sample fluid passes is formed between the micro-channel chip 1730 and the quartz-crystal resonator 1720.

A planar shape of the concave portion for passage 1732 is formed in a flat rhombus which is long in a horizontal direction, and on both left and right end portions in a major axis direction of the rhombus, there are formed a liquid supply port 1733 for supplying the sample fluid into the passage space and a liquid discharge port 1734 for discharging the sample fluid from the passage space. The passage space formed between the micro-channel chip 1730 and the quartz-crystal resonator 1720 is a minute space of about several microliters, for example, so that even when an amount of sample containing the substance to be sensed is small, it becomes possible to supply the sample fluid to the passage space without diluting the fluid, which enables to enhance a sensitivity in a low-concentration area.

Further, by making the planar shape of the concave portion for passage 1732 in a flat rhombus, the sample fluid supplied from the liquid supply port 1733 flows in the major axis direction of the rhombus while spreading in a minor axis direction thereof, and it soon reaches the liquid discharge port 1734 so as to be guided by the channel whose width in the minor axis direction gradually narrows down. In the passage space formed as above, there exists, on the channel, no narrow angle portion in which the sample fluid hardly reaches or it easily resides, and further, a change in a direction of streamline of the sample fluid flowing through the space is also small. For this reason, even though the portion has a very narrow space of about sub-millimeters, residence of air or the like hardly occurs, resulting in that the sample fluid can be smoothly spread within the entire passage space.

However, the planar shape of the concave portion for passage 1732 is not limited to the flat rhombus shown in FIG. 24, and may also be a shape in which the residence of air or the like hardly occurs, which is, for example, a circular shape or the like.

Further, positioning holes 1735 formed on the micro-channel chip 1730 are positioning holes for fixing and positioning the micro-channel chip 1730 by inserting the positioning pins 1631 on the flow cell base 1600 side in the holes.

The micro-channel chip 1730 shown in FIG. 24 corresponds to the channel forming member 5 shown in FIG. 2, FIGS. 7(*a*) and 7(*b*), FIG. 8 and the like. Therefore, although there are formed, in the concave portion for passage 1732 of the micro-channel chip 1730, the groove portions 55 provided to the channel forming member 5 in FIGS. 7(*a*) and 7(*b*), the description of the groove portions 55 is omitted in FIG. 24. Further, a case where the micro-channel chip 1730 including no groove portions 55 is used, is also not excluded.

Next, explanation will be made on the flow cell cover 1510. As shown in FIG. 20, the flow cell cover 1510 is a member formed in a substantially rectangular parallelepiped shape, and inside thereof, there are formed a supply channel 1511 for supplying the sample fluid and a discharge channel 1512 for discharge. These supply channel 1511 and discharge channel 1512 are opened, on a lower surface of the flow cell cover 1510, at positions capable of being connected to the liquid supply port 1733 and the liquid discharge port 1734 provided on the micro-channel chip 1730 side.

When the piezoelectric sensor 1700 and the micro-channel chip 1730 are vertically laid one on the other and disposed on the concave portion 1630 of the flow cell base 1600, an upper surface of the micro-channel chip 1730 is in the same plane as an upper surface of the flow cell base 1600 or in a state of slightly projecting upward from the upper surface of the flow cell base. By pressing the upper surface of the micro-channel chip 1730 using a bottom surface of the flow cell cover 1510 to press the micro-channel chip 1730 against a plate surface of the piezoelectric sensor 1700, the micro-channel chip 1730 is fixed, resulting in that the passage space is sealed, and at the same time, the supply channel 1511, the discharge channel 1512 on the flow cell cover 1510 side are respectively connected to the liquid supply port 1733, the liquid discharge port 1734 on the micro-channel chip 1730 side.

However, since the height of the passage space formed between the concave portion for passage 1732 of the micro-channel chip 1730 and the quartz-crystal resonator 1720 is very small to be about sub-millimeters as described above, and further, since the micro-channel chip 1730 is made of the elastic material such as the silicon rubber, when the micro-channel chip is pressed with an excessively strong force, the passage space may be flattened. Accordingly, the flow cell cover 1510 of the present example presses the flow cell cover 1510 downward with a uniform force by utilizing the spring plungers 1350 provided on the raising/lowering mechanism 1300 side, as described using FIG. 17, to thereby prevent the passage space from being flattened.

The supply channel 1511 and the discharge channel 1512 of the flow cell cover 1510 are respectively connected to a supply pipe 1131 and a discharge pipe 1132 as shown in FIG. 13, in which the supply pipe 1131 is connected to a not-shown sample supply part that stores the sample solution being the sample fluid containing the substance to be sensed or the like, and further, the discharge pipe 1132 is connected to a not-shown discharge part to be a discharge destination of the sample fluid. The supply of the sample fluid from the sample supply part to the passage space may also be conducted by pushing out the sample fluid from the sample supply part side using a syringe pump or the like, or may also be conducted by drawing the sample fluid from the discharge part side using a vacuum pump or the like.

A component denoted by 1133 shown in FIG. 13 is a guide member that guides the respective pipes 1131, 1132 to prevent the supply pipe 1131 and the discharge pipe 1132 from being bent or mutually entangled even when the flow cell cover 1510 is raised/lowered, and a component denoted by 1134 is a clip member that bundles these pipes to guide them to the sample supply part and discharge part sides.

As described above, the explanation was made, while referring to FIG. 20 to FIG. 24, on the structures of the respective members 1600, 1700, 1730, 1510 for fixing the micro-channel chip 1730 which is used as the channel forming member, by pressing it against the plate surface of the piezoelectric sensor 1700 using the flow cell cover 1510. Here, the sensing device 1100 according to the present example can also form a passage space of sample fluid by using a channel forming member other than the micro-channel chip 1730, by replacing the flow cell base 1600, the piezoelectric sensor 1700, the flow cell cover 1510.

Figure 25:
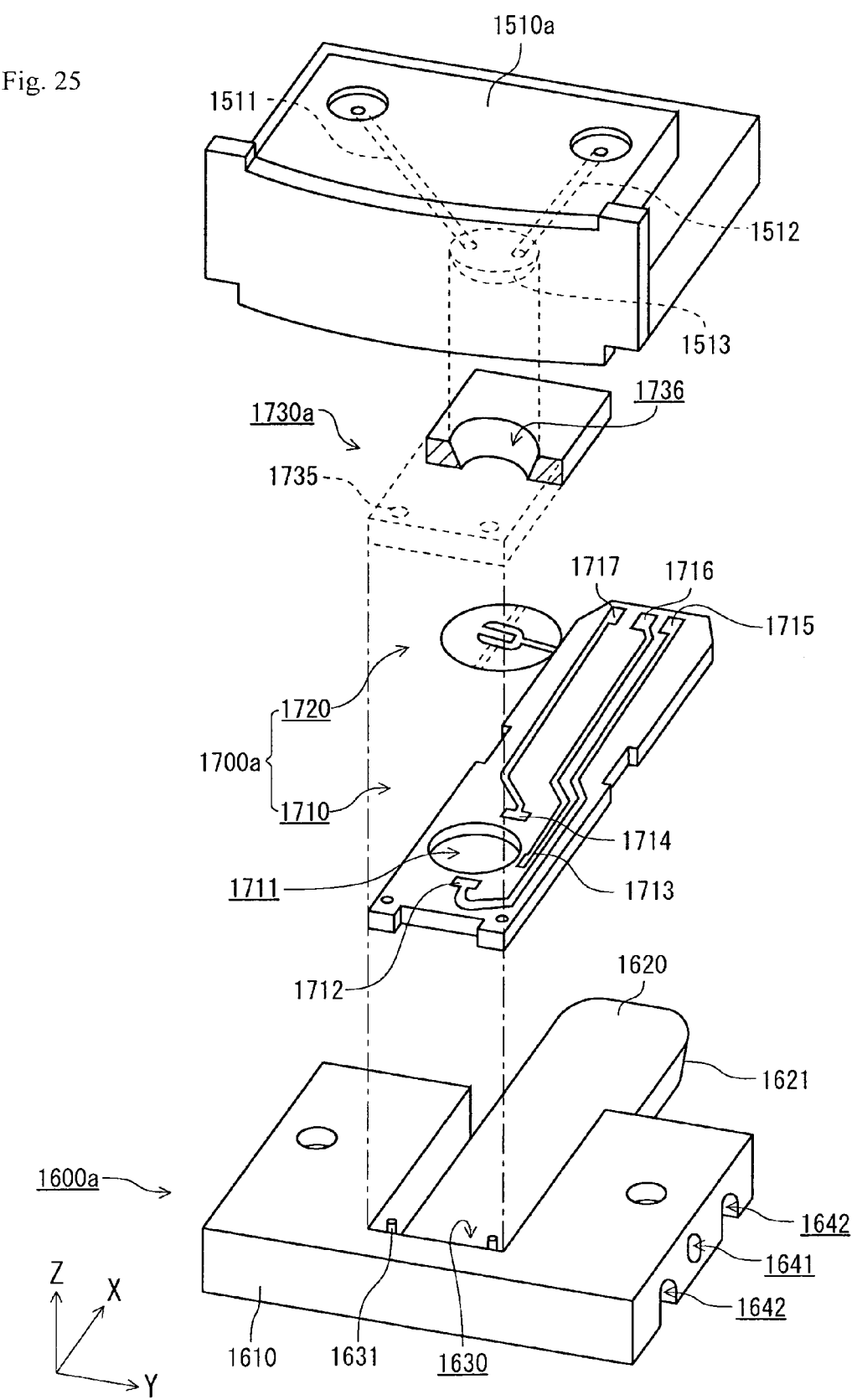
FIG. 25 is an exploded perspective view showing an another structural example of the flow cell base, the flow cell cover and the piezoelectric sensor mounted therebetween.

For instance, FIG. 25 shows an example in which a rubber packing 1730*a* is used to form a passage space with a piezoelectric sensor 1700*a*. In FIG. 25, a component same as that shown in FIG. 20 is denoted by the same reference numeral as that of FIG. 20. In the example shown in FIG. 25, there is formed, on a center portion of the rubber packing 1730*a*, a through hole 1736 having a cone-shaped inclined surface, and when the piezoelectric sensor 1700*a* is held to a flow cell base 1600*a* and the rubber packing 1730*a* is fixed by a flow cell cover 1510*a*, the passage space is formed among an upper surface of the piezoelectric sensor 1700*a* (quartz-crystal resonator 1720), a side peripheral surface of the through hole 1736 and a lower surface of the flow cell cover 1510*a*. In the example using the rubber packing 1730*a*, a volume of the passage space is about several tens of microliters, which is larger than that of the micro-channel chip 1730, and thus the example is selected in a case where analysis of a sample fluid whose available amount is relatively large or a sample fluid whose viscosity is high and thus it is difficult to make the fluid pass through the narrow passage space of the micro-channel chip 1730, or the like.

Here, on the lower surface of the flow cell cover 1510*a* of the present example, a sealing portion 1513 for sealing the passage space by being fitted in an opening portion on an upper surface side of the through hole 1736, is provided to project downward, and the supply channel 1511 and the discharge channel 1512 formed on the flow cell cover 1510*a* are opened to a lower surface of the sealing portion 1513. Further, the quartz-crystal resonator 1720 of the piezoelectric sensor 1700*a* is formed to have a slightly small diameter, compared with the piezoelectric sensor 1700 for the micro-channel chip 1730 that is formed slightly largely, in order to absorb a substance to be sensed contained in a quite small amount of sample fluid as much as possible. In accordance with this, the front portion of the wiring board 1710 and the concave portion 1630 of the flow cell base 1600a are also formed to be slightly small, which is also different from the flow cell base 1600, the piezoelectric sensor 1700 described in FIG. 20.

The sensing device 1100 of the present embodiment including the structures described above is connected to the control unit 1800, as shown in FIG. 26. The control unit 1800 is formed of a computer including not-shown CPU and storage part, and in the storage part, there is recorded a program including a step (instruction) group regarding a control relating to an operation in which the moving mechanism 1200 of the flow cell base 1600 and the raising/lowering mechanism 1300 of the flow cell cover 1510 are operated to mount the piezoelectric sensor 1700 to the sensing device 1100 and the sensing of the substance to be sensed is conducted by supplying the sample fluid into the passage space formed by the micro-channel chip 1730 or the rubber packing 1730a with the quartz-crystal resonator 1720. This program is stored in a storage medium such as, for example, a hard disk, a compact disk, a magneto-optical disk and a memory card, and is installed in the computer from the storage medium.

Here, the moving mechanism 1200 includes a function to stop the moving operation of the flow cell base 1600 when a foreign substance gets stuck on a migration path of the flow cell base 1600, or the like. Further, the raising/lowering mechanism 1300 also includes a function to stop the raising/lowering operation of the flow cell cover 1510 when a foreign substance gets stuck or the like at the time of raising/lowering the flow cell cover 1510 between the fixing position of the micro-channel chip 1730 or the rubber packing 1730a and the retreat position retreating from the fixing position.

As a unit of realizing the function to stop the moving mechanism 1200 and the raising/lowering mechanism 1300, in the sensing device 1100, there is provided a resistor 1850 to a ground line from a motor driver 1830 (which is comprehensively illustrated as one motor driver 1830 for the moving mechanism 1200 and the raising/lowering mechanism 1300, in the block diagram in FIG. 26) that supplies electric power to each of the rotation motors 1235, 1314 of the moving mechanism 1200 and the raising/lowering mechanism 1300, and by monitoring a voltage applied to the resistor 1850, a load applied to each of the rotation motors 1235, 1314 is monitored.

Figure 27:
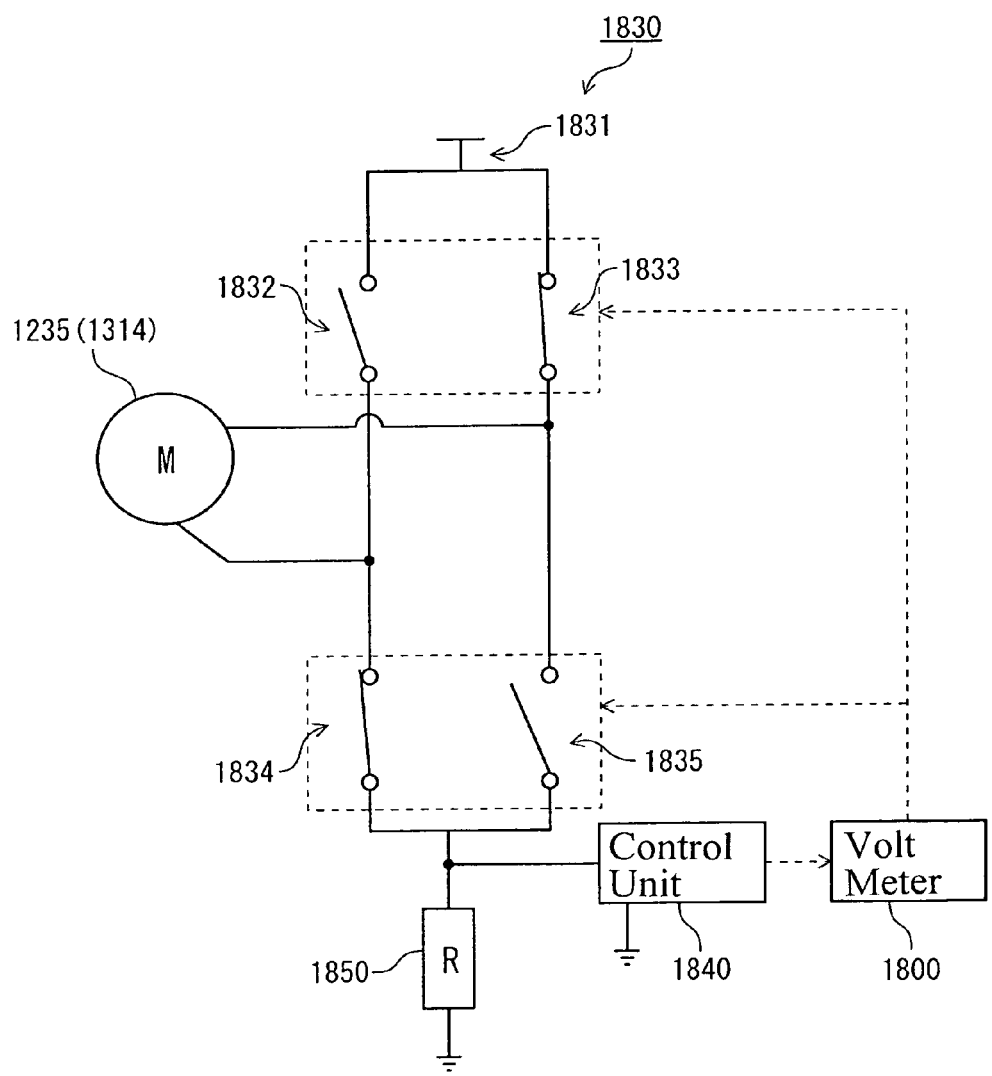
FIG. 27 is an explanatory diagram showing a structural example of a switch circuit relating to driving and stopping of the moving mechanism and the raising/lowering mechanism.

FIG. 27 shows a structural example of a switch circuit provided inside the motor driver 1830 and a stop mechanism for stopping the aforementioned moving mechanism 1200 and raising/lowering mechanism 1300 by being connected to the circuit. The switch circuit has a structure in which switch parts 1832, 1834 and 1833, 1835 are connected in series in two pieces each, and these two systems of switch parts 1832, 1834, 1833, 1835 are mutually connected in parallel with respect to a power supply part 1831, and the switch parts 1834, 1835 at a rear stage are grounded. Further, the rotation motors 1235, 1314 are provided on bridge lines that connect these two systems of switch parts 1832, 1834, 1833, 1835 at intermediate positions.

Each of the switch parts 1832, 1834, 1833, 1835 is designed to execute an opening/closing operation based on an instruction from the control unit 1800. Further, as shown in FIG. 27, for example, when the switch parts 1833, 1834 are "closed", and the switch parts 1832, 1835 are "opened", the rotation motors 1235, 1314 are normally rotated, and on the contrary, when the switch parts 1832, 1835 are "closed", and the switch parts 1833, 1834 are "opened", the motors are reversely rotated.

The resistor 1850 is provided on the ground line of the motor driver 1830, and a voltage value measured by the resistor 1850 is designed to be output to the control unit 1800 at a predetermined time interval. Further, when the operation of the moving mechanism 1200 and the raising/lowering mechanism 1300 is forcibly stopped, when a foreign substance gets stuck or the like, while continuously supplying electric power to the rotation motors 1235, 1314, an excessive load is applied to the rotation motors 1235, 1314, resulting in that electric power supplied to the rotation motors 1235, 1314 increases for obtaining a driving force in accordance with the load, and the increase in the electric power is detected as an increase in voltage applied to the resistor 1850.

The control unit 1800 compares the voltage value obtained from a voltmeter 1840 with a previously stored threshold value, and when the voltage value becomes greater than the threshold value, it turns all of the switch parts 1832, 1834, 1833, 1835 into the "open" state to stop the supply of electric power to the rotation motors 1235, 1314, and it is possible to independently stop each operation of the moving mechanism 1200 or the raising/lowering mechanism 1300.

Figure 28A:
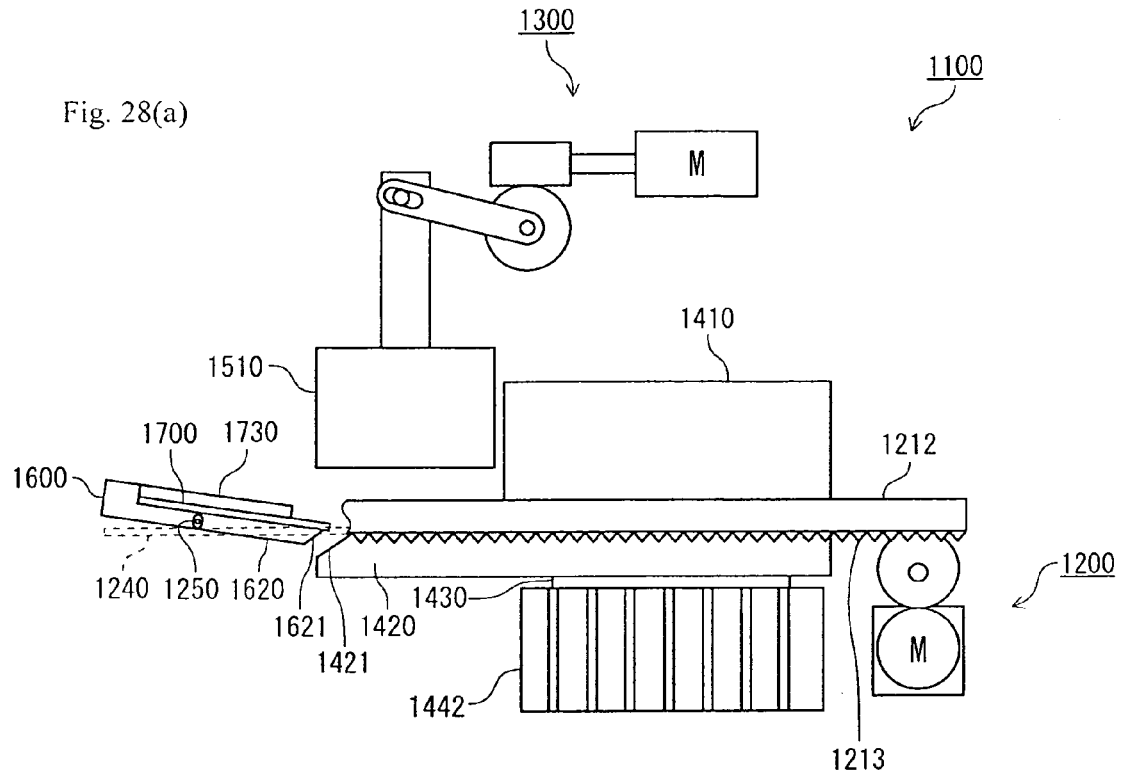
FIGS. 28(a) and 28(b) are first explanatory diagrams showing operations of the sensing device.
Figure 28B:
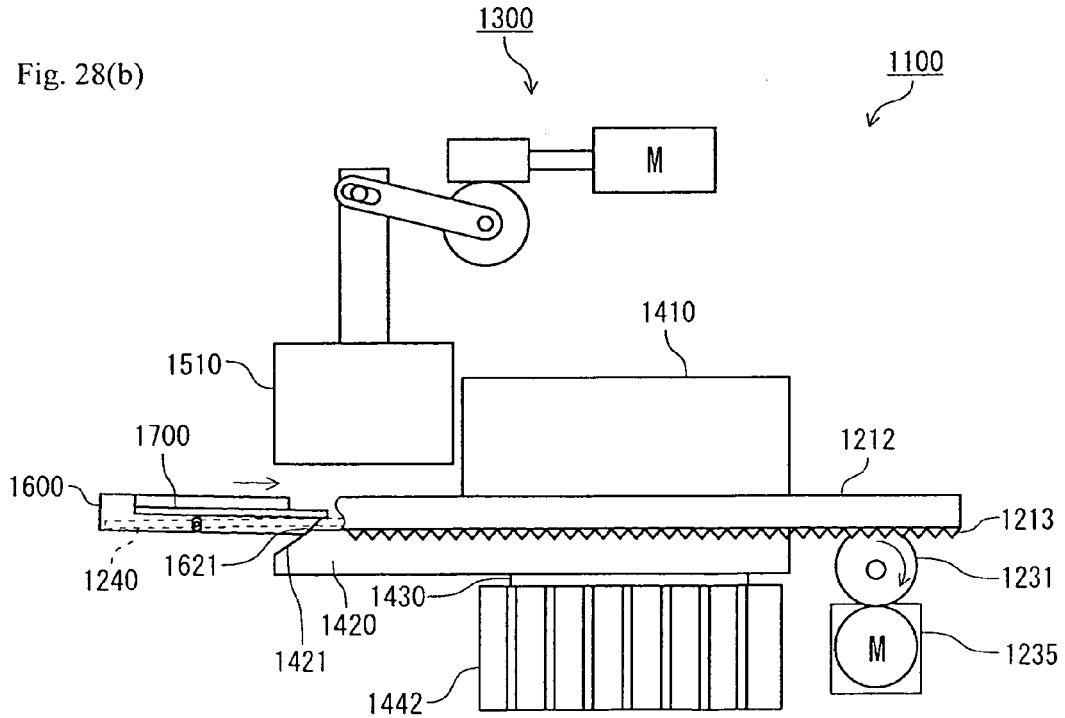
Figure 29A:
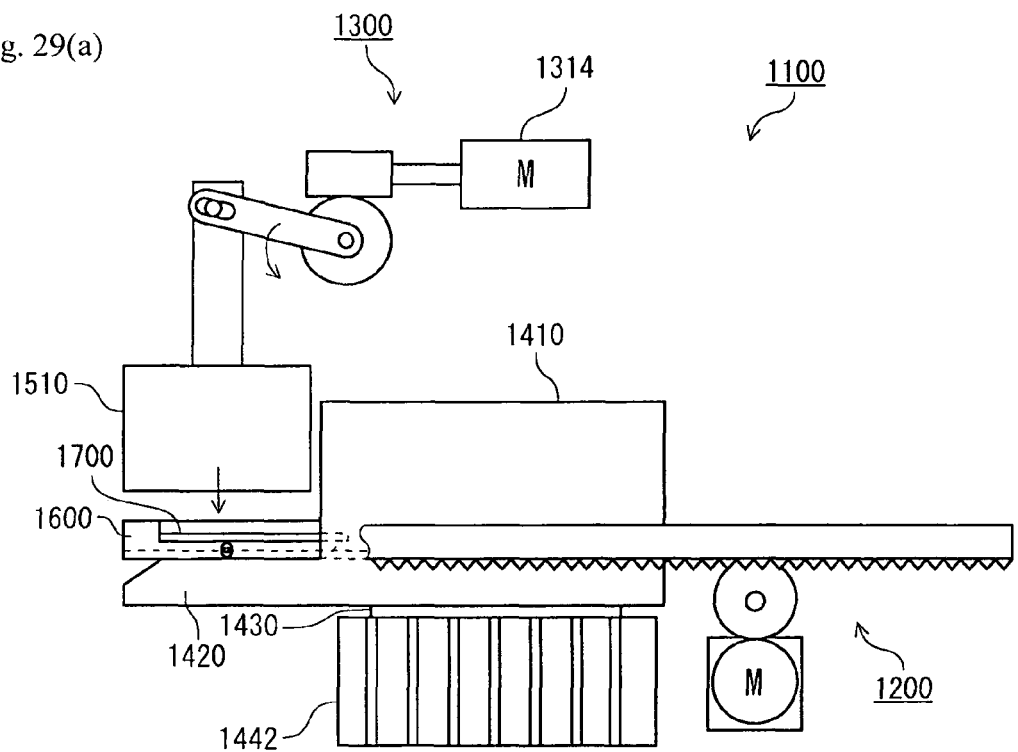
FIGS. 29(a) and 29(b) are second explanatory diagrams showing operations of the sensing device.
Figure 29B:
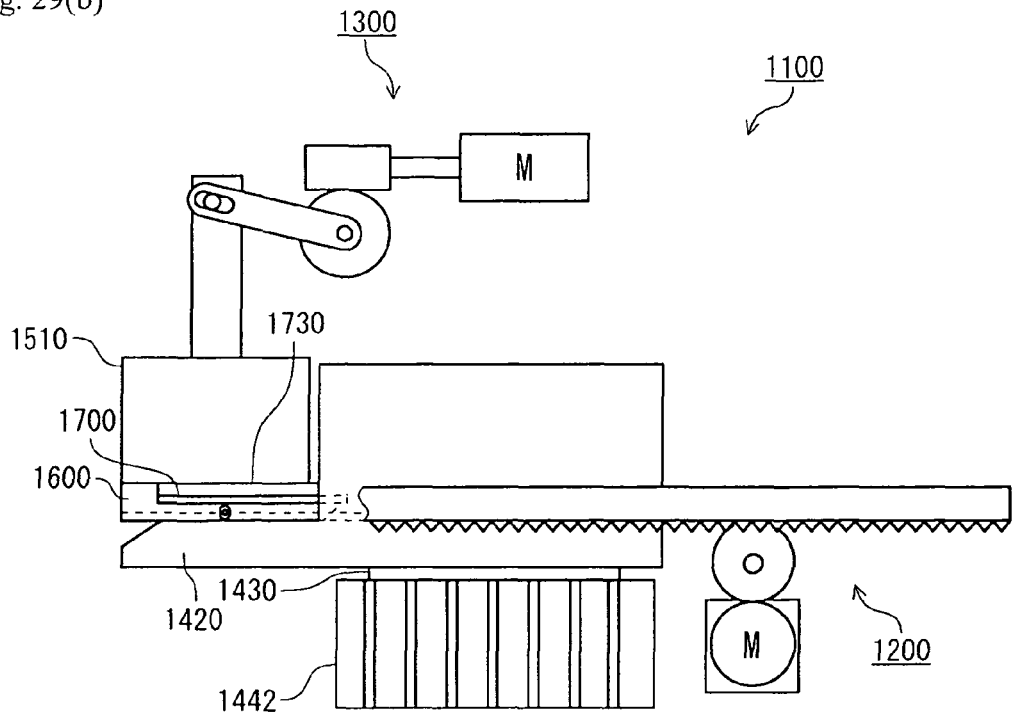

Hereinafter, an operation of the sensing device 1100 will be explained. FIGS. 28 to FIGS. 29 show a case where the micro-channel chip 1730 is used as the channel forming member. In the sensing device 1100, the temperature of the chassis part 1410 and the guide member 1420 is adjusted to a previously set temperature by the Peltier element 1430, and under this state, the flow cell cover 1510 is raised to the retreat position and the flow cell base 1600 is made to move backward to the holding position, as shown in FIG. 28(a). After that, the flow cell base 1600 is made to hold the piezoelectric sensor 1700 and the micro-channel chip 1730 is placed on the upper surface of the piezoelectric sensor, resulting in that the flow cell base 1600 inclines toward the far side around the mounting screws 1250 because of the weight on the projecting piece portion 1620 side, and is in a state where the surface to be guided 1621 of the projecting piece portion 1620 is faced downward. At this time, at least a lower end portion of the projecting piece portion 1620 moves to a position lower than a position of an upper end portion of the guide surface 1421 of the guide member 1420.

Thereafter, when the rotation motor 1235 of the moving mechanism 1200 is operated to make the flow cell base 1600 move forward toward the connecting position side, the surface to be guided 1621 of the projecting piece portion 1620 abuts on the guide surface 1421 of the guide member 1420. At this time, since the flow cell base 1600 is mounted to the arm members 1212 with an allowance with which it can move in the longitudinal direction as described above, the projecting piece portion 1620 moves diagonally upward so as to be guided by the guide surface 1421 (FIG. 28(b)).

Further, when the bottom surface of the flow cell base 1600 reaches the upper end portion of the guide surface 1421, the flow cell base 1600 runs upon the upper surface of the guide member 1420, resulting in that the flow cell base 1600 is in a state of being placed on the guide member 1420. The flow cell base 1600 moves, under this state, on the guide member 1420 in the horizontal direction, and when the piezoelectric sensor 1700 reaches the connecting position, the moving mechanism 1200 stops the movement of the flow cell base 1600. As a result of this, there is created a state where the terminal portions 1715 to 1717 provided on the rear end portion of the wiring board 1710 are brought into contact with the terminal portion 1412 on the oscillator circuit portions 1810a, 1810b sides in the chassis part 1410, and the respective oscillation areas 1701a, 1701b are connected to the oscillator circuit portions 1810a, 1810b, as shown in FIG. 29(*a*).

Here, if a foreign substance gets stuck or the like until when the flow cell base 1600 moves from the holding position to the connecting position, an excessive load is applied to the rotation motor 1235, resulting in that the switch circuit in the motor driver 1830 operates to stop the movement of the flow cell base 1600. Further, for example, when a user removes a cause of the stop such as the foreign substance, and an operation start instruction is received from a not-shown operation switch or the like, the movement of the flow cell base 1600 is started again.

Further, since the flow cell base 1600 is placed on the guide member 1420 and mounted to the arm members 1212 with an allowance with which it can move in the longitudinal direction, even in a case of using the moving mechanism 1200 including a mechanism such as the pinion-rack mechanism (the rack gear 1213, the pinion member 1231) in which a backlash in the longitudinal direction is likely to occur, the flow cell base 1600 is guided toward the connection port 1411 at the same height position every time in a state of being positioned on the upper surface of the guide member 1420. For this reason, when compared with a case where the piezoelectric sensor 1700 is connected to the connection port 1411 by hand, a smooth mounting can be realized without carelessly bumping the piezoelectric sensor 1700 against peripheral devices.

In the operation described above, the flow cell base 1600 moves in a state of being pressed on the guide member 1420 side by the own weights of the flow cell base 1600, the piezoelectric sensor 1700 and the micro-channel chip 1730, so that it does not incline to an unnecessary direction, resulting in that the piezoelectric sensor 1700 can be connected to the first and second oscillator circuit portions 1810a, 1810b while keeping the quartz-crystal resonator 1720 in a horizontal state. As a result of this, when compared with a case where, for example, the mounting operation is conducted by hand, the piezoelectric sensor 1700 is mounted to the chassis part 1410 in a state of being inclined due to a displacement in an insertion direction in the connection port 1411 or the like, and the piezoelectric sensor is pressed, under that state, from the upper surface side by the flow cell cover 1510, a stress applied to the quartz-crystal resonator 1720 is small, and there is a small possibility of deterioration of characteristic at the time of sensing the substance to be sensed.

Figure 30A:
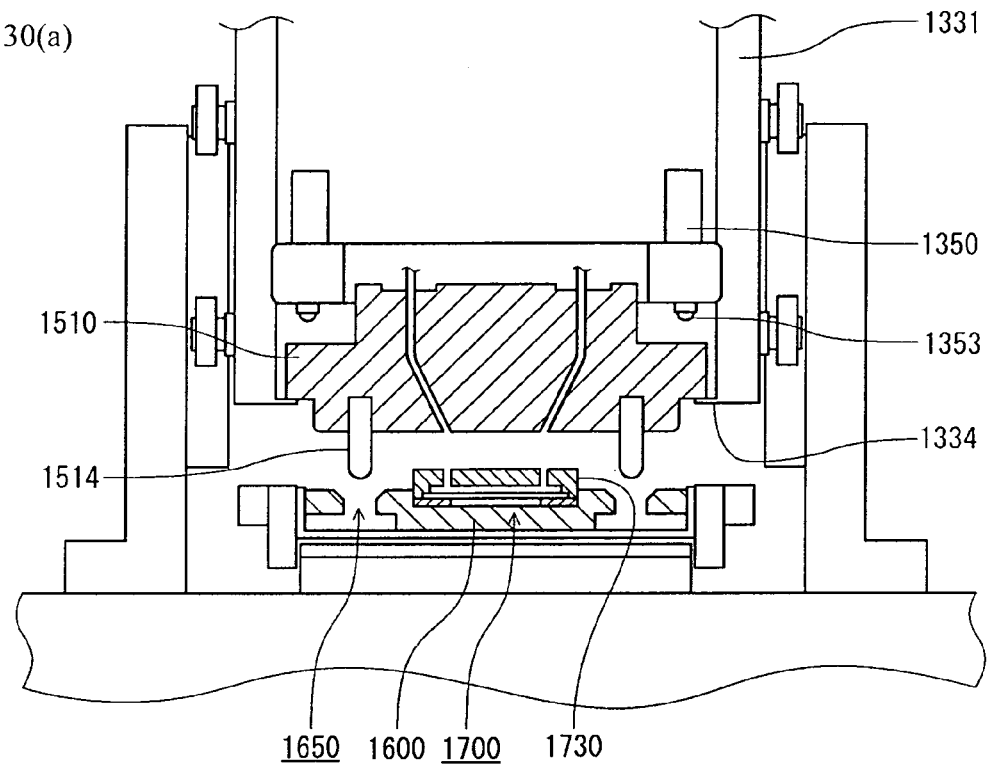
FIGS. 30(a) and 30(b) are third explanatory diagrams showing operations of the sensing device.
Figure 30B:
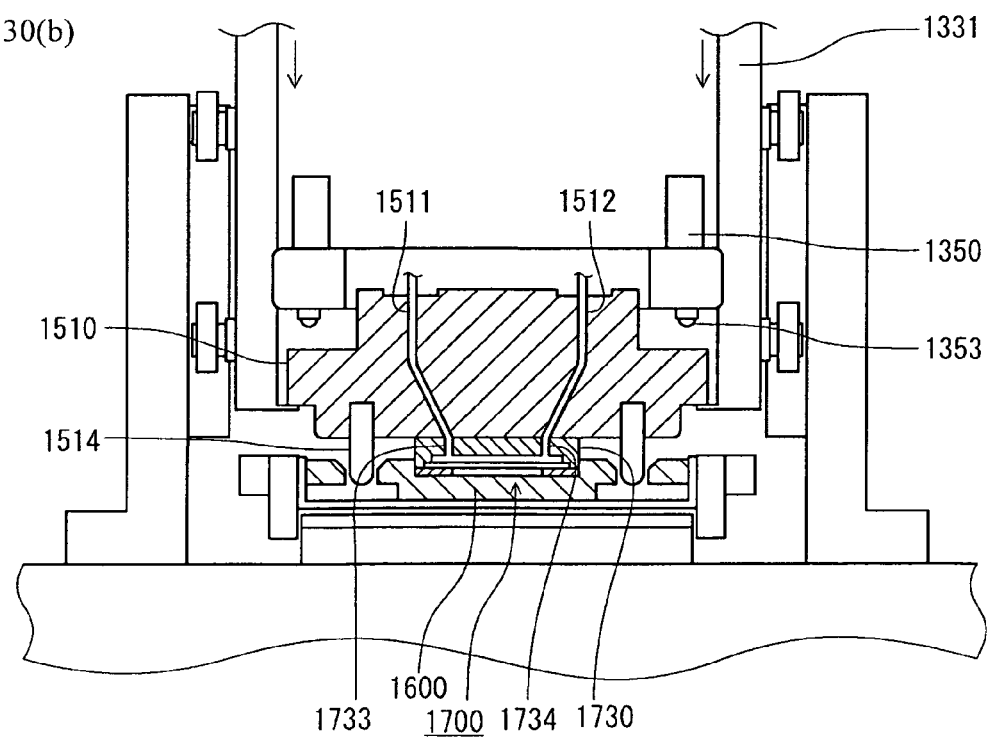

When the piezoelectric sensor 1700 is connected to the first and second oscillator circuit portions 1810a, 1810b as above, the support members 1331 stand by in a state where they raise the flow cell cover 1510 to an attaching/detaching position and raise the spring plungers 1350 to a release position, as shown in FIG. 30(*a*). At this time, the flow cell cover 1510 has guide shafts 1514 projecting from the lower surface thereof which retreat to a height position at which they do not interfere with the flow cell base 1600 that conveys the piezoelectric sensor 1700 to the connecting position, and the lower surface of the flow cell cover is not brought into contact with the micro-channel chip 1730. Further, in the present example, the spring plungers 1350 also retreat to a position further above the flow cell cover 1510 positioned at the release position, and the abutting members 1353 are separated from the upper surface of the flow cell cover 1510. However, it is also possible that, when the flow cell cover 1510 is at the release position, a positional displacement of the flow cell cover 1510 at the time of performing the raising/lowering is prevented by making the abutting members 1353 abut on the upper surface of the flow cell cover 1510 while sufficiently securing the moving range of the abutting members 1353.

As above, when the piezoelectric sensor 1700 reaches the connecting position and is connected to the oscillator circuit portions 1810a, 1810b, the rotation motor 1314 is operated to lower the support members 1331, and the flow cell cover 1510 retreated to the release position is lowered (FIG. 29(*a*)). When the flow cell cover 1510 is lowered, as shown in FIG. 30(*b*), the guide shafts 1514 first enter positioning holes 1650 of the flow cell base 1600 and guided by the positioning holes 1650, thereby realizing the positioning of the flow cell cover 1510 with respect to the flow cell base 1600.

Subsequently, when the flow cell cover 1510 is further lowered, the flow cell cover 1510 is placed on the micro-channel chip 1730. At this time, since the positioning is realized between the flow cell base 1600 and the flow cell cover 1510, there is created a state where the supply channel 1511 and the discharge channel 1512 on the flow cell cover 1510 side communicate with the liquid supply port 1733 and the liquid discharge port 1734 on the micro-channel chip 1730 side, respectively.

Figure 31:
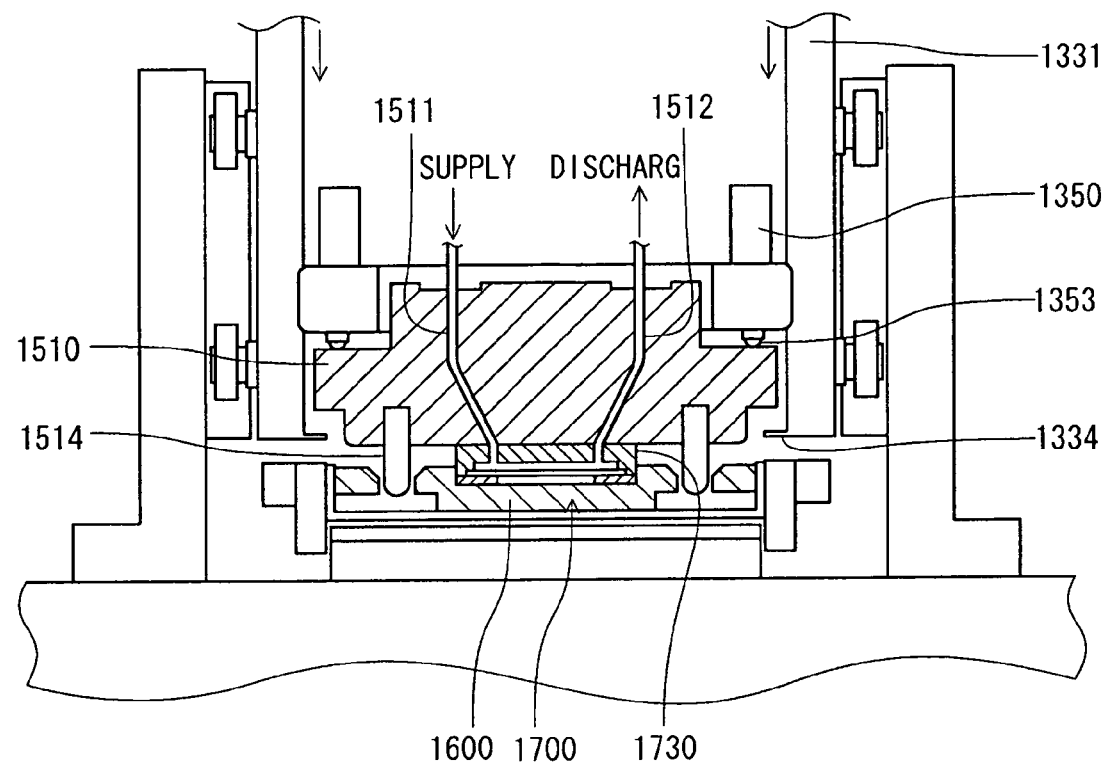
FIG. 31 is a fourth explanatory diagram showing an operation of the sensing device.

Furthermore, when the support members 1331 are lowered, the chuck portions 1334 are separated from the lower surface of the flow cell cover 1510, which releases a state of holding the flow cell cover 1510, and meanwhile, the abutting members 1353 of the spring plungers 1350 reach the upper surface of the flow cell cover 1510, as shown in FIG. 31. Thereafter, when the support members 1331 are lowered to a position at which a lower limit sensor 1373 shown in FIG. 18 operates, the rotation motor 1314 stops to stop the movement of the support members 1331 (FIG. 29(*b*)).

At this time, a position at which the support members 1331 stop is set to, for example, an intermediate height position in the moving range of the abutting members 1353 explained using FIG. 19. For this reason, the four spring plungers 1350 apply an even pressing force in accordance with the spring constant of the spring members 1352 to the flow cell cover 1510. Further, at this time, even when the height of the piezoelectric sensor 1700, the micro-channel chip 1730 or the like is varied within a range of about sub-millimeters, for example, due to a processing tolerance, or the like, if the variation width is within the moving range of the abutting members 1353, the pressing force of the spring plungers 1350 does not change.

As above, by pressing the flow cell cover 1510 on the micro-channel chip 1730 side using the spring plungers 1350, the close-contact between the micro-channel chip 1730 and the piezoelectric sensor 1700 is secured. Further, since the flow cell cover 1510 can be pressed with a constant force within the moving range of the abutting members 1353 of the spring plungers 1350, even when the height position of the upper surface of the micro-channel chip 1730 is shifted upward due to the reason of the processing tolerance or the like, an excessive force is prevented from being applied to the micro-channel chip 1730 to flatten or distort the passage space, which reduces a possibility of imposing an adverse effect on the characteristic of sensing the substance to be sensed of the quartz-crystal resonator 1720. Further, on the contrary, even when the aforementioned height position of the upper surface is shifted downward, it is possible to suppress the occurrence of problems such that the force to press the micro-channel chip 1730 becomes weak and the sufficient close-contact between the micro-channel chip and the piezoelectric sensor 1700 cannot be maintained, resulting in that the sample fluid leaks.

Also at this time, if a foreign substance or the like gets stuck until when the flow cell cover 1510 moves from the retreat position to the fixing position, an excessive load is applied to the rotation motor 1314, and the switch circuit in the motor driver 1830 operates to stop the lowering operation of the flow cell cover 1510. Further, when a cause of the stop such as the foreign substance is removed, a start instruction of operation is received to start the lowering of the flow cell cover 1510 again.

Also in this operation, the flow cell cover 1510 is stopped at the previously set fixing position, so that a force applied to the micro-channel chip 1730 becomes constant, compared with a case where the flow cell cover 1510 is disposed on the piezoelectric sensor 1700 by hand. For this reason, there is a small possibility of imposing an adverse effect on the characteristic of sensing the substance to be sensed of the quartz-crystal resonator 1720 by flattening or distorting the channel.

When the flow cell cover 1510 is lowered to the fixing position to fix the micro-channel chip 1730, and the supply and discharge channels 1511, 1512 on the flow cell cover 1510 side and the liquid supply and liquid discharge ports 1733, 1734 on the micro-channel chip 1730 side are connected, a buffer solution is started to be supplied into the passage space from the supply pipe 1131, and at the same time, the respective oscillator circuit portions 1810a, 1810b are operated to start obtaining the oscillation frequencies of the respective oscillation areas 1701a, 1701b, for example.

Thereafter, for example, when the temperature of the quartz-crystal resonator 1720 is stabilized and the oscillation frequency becomes constant, a sample solution being a sample fluid is supplied to the supply pipe 1131, and the sample solution reaches the passage space, in which when a substance to be sensed is contained in the sample solution, the substance to be sensed is absorbed in the absorption layer 1702. As a result of this, the oscillation frequency of the oscillation area on which the absorption layer 1702 is provided (the first oscillation area 1701a, in the example shown in FIG. 23) is decreased, which enables to sense the existence of the substance to be sensed, and further, it is also possible to quantify an absorption amount of the substance to be sensed based on an amount of decrease in the oscillation frequency.

After the sensing of the substance to be sensed is completed, the sample fluid is removed from the passage space by supplying purge gas from the supply pipe 1131 or the like, and the flow cell cover 1510 and the spring plungers 1350 are raised to the attaching/detaching position and the release position, respectively, contrary to the time of the connection. Thereafter, by making the flow cell base 1600 move to the holding position, the piezoelectric sensor 1700 after completing the sensing operation can be detached from the flow cell base 1600. Also at this time, in a case where a foreign substance gets stuck or the like, it is of course that the raising operation of the flow cell cover 1510 and the moving operation of the flow cell base 1600 are stopped.

The sensing device 1100 according to the present embodiment provides the following effects. There are provided the spring plungers 1350 pressing the flow cell cover 1510 with a previously set force when the piezoelectric sensor 1700 provided with the quartz-crystal resonator 1720 and the channel forming member (the micro-channel chip 1730 or the rubber packing 1730a) being placed on the piezoelectric sensor 1700 and forming, on the upper surface side of the quartz-crystal resonator 1720, the passage space through which the sample fluid passes, are held to the flow cell base 1600 in a state of being vertically stacked, and the flow cell cover 1510 for realizing the close-contact between the channel forming member and the piezoelectric sensor is placed on the channel forming member. For this reason, by properly adjusting the aforementioned previously set force, it is possible to realize the close-contact between the piezoelectric sensor 1700 and the channel forming member to prevent the sample fluid from leaking from the passage space, and at the same time, it is possible to suppress the occurrence of problems such that the passage space is flattened so that the sample fluid cannot pass through the space or the sensing characteristic is changed, by suppressing an excessive deformation of the channel forming member made of the elastic material.

Figure 32A:
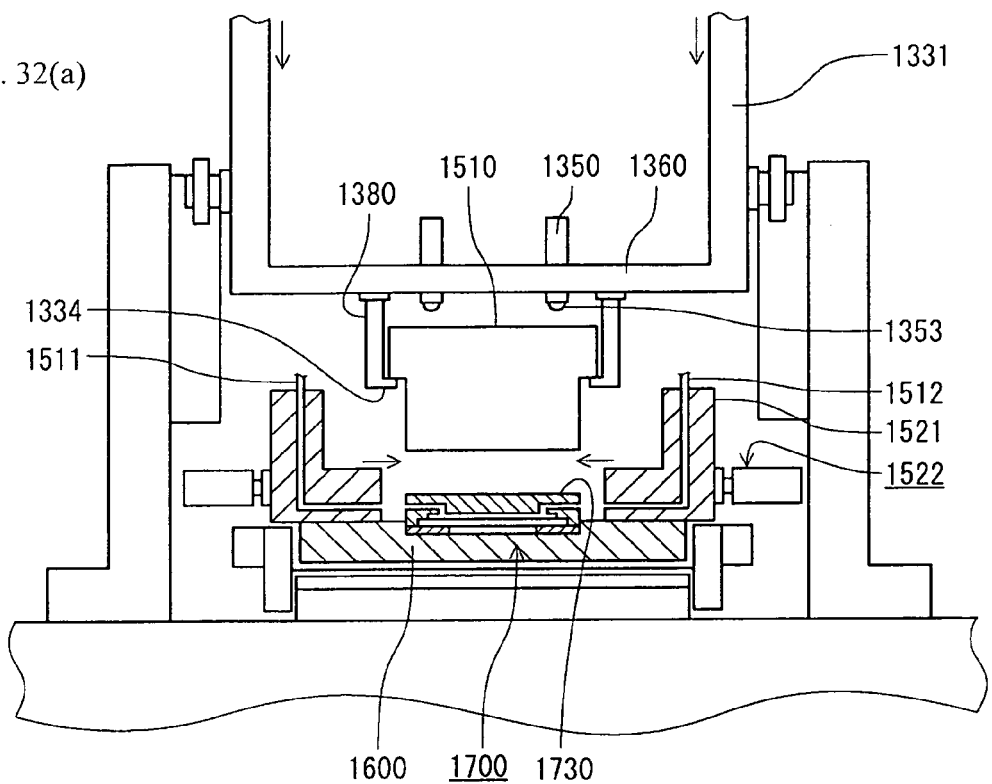
FIGS. 32(a) and 32(b) are explanatory diagrams showing an another example of the flow cell cover.
Figure 32B:
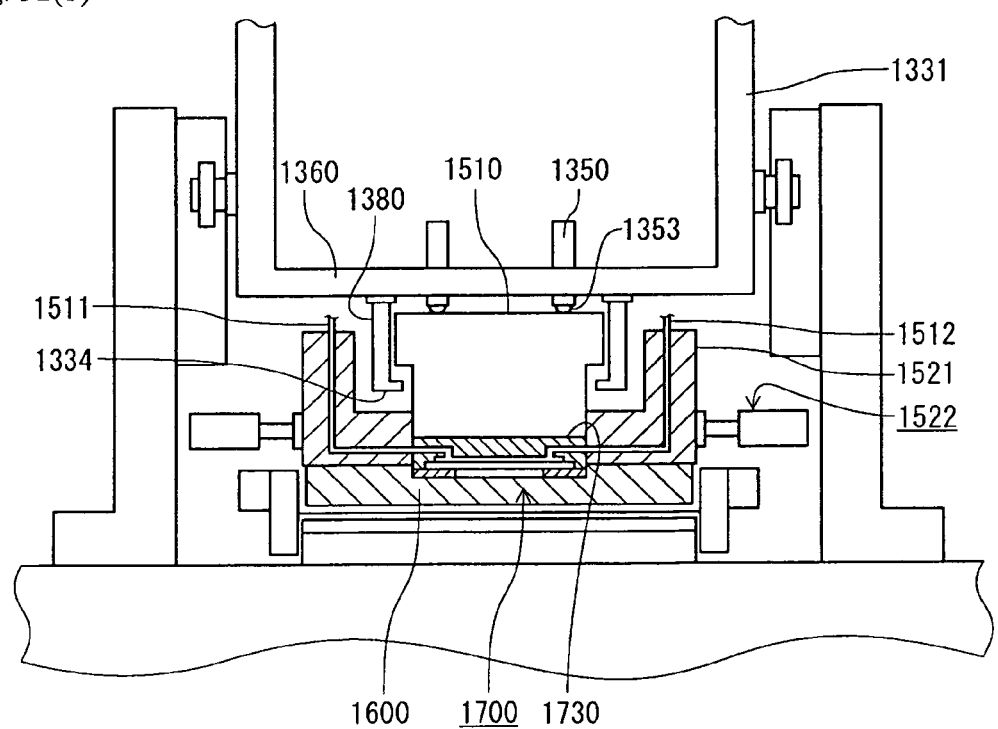

Here, the aforementioned embodiment explained an example in which, as shown in FIG. 18 and FIG. 20, the supply channel 1511 and the discharge channel 1512 of the sample fluid are formed in the flow cell cover 1510, and the sample solution supply part and the sample solution discharge part are made common with the flow cell cover 1510, but, it is also possible to structure such that these elements are provided independently. In the sensing device 1100 shown in FIG. 32(a) and FIG. 32(b), the liquid supply port 1731 and the liquid discharge port 1732 of the sample fluid are provided on side surfaces of the micro-channel chip 1730, and the device includes a sample solution supply part 1523, a sample solution discharge part 1521 structured separately from the flow cell cover 1510. In FIG. 32, the components same as those shown in FIG. 13 to FIG. 31 are denoted by the same reference numerals as those in these drawings.

In this example, the supply channel 1511, the discharge channel 1512 which are communicated with the liquid supply port 1731, the liquid discharge port 1732 are formed in the sample solution supply part 1523, the sample solution discharge part 1521, respectively, and meanwhile, these channels 1511, 1512 are not formed in the flow cell cover 1510. Further, the holder 1360 that holds the spring plungers 1350 is structured as a bar-shaped member bridged laterally on the lower end portions of the raised/lowered two support members 1331, and from the lower surface of the holder 1360, two raising/lowering arms 1380 for raising/lowering the flow cell cover 1510 extend downward. On lower end portions of these raising/lowering arms 1380, there are provided the chuck portions 1334 which lift the flow cell cover 1510 by being locked to the lower surface of the flow cell cover 1510. Further, with the use of the common raising/lowering mechanism 1300 (in FIG. 32, only a part thereof such as the support members 1331 is illustrated), the raising/lowering arms 1380 are vertically moved to raise/lower the flow cell cover 1510 between an attaching/detaching position and a placing position. Further, by raising/lowering the holder 1360 by similarly using the raising/lowering mechanism 1300, the spring plungers 1350 are raised/lowered between a release position and a pressing position.

Meanwhile, the sample solution supply part 1523 and the sample solution discharge part 1521 are provide with moving mechanisms 1522 that move these parts in a horizontal direction. Further, at the time of carrying-in/out the piezoelectric sensor 1700 with the use of the flow call base 1600, these members 1523, 1521 are retreated to the outside in the horizontal direction, as shown in FIG. 32(a). On the other hand, when the piezoelectric sensor 1700 is mounted to the sensing device 1100, the sample solution supply part 1523 and the sample solution discharge part 1521 are moved to the inside as shown in FIG. 32(b), to make the supply channel 1511, the discharge channel 1512 communicate with the liquid supply port 1731, the liquid discharge port 1732, respectively.

Further, the raising/lowering mechanism 1300 is not limited to the case where it is made common to the flow cell cover 1510 and the spring plungers 1350, and it is also possible to conduct the raising/lowering operation of these members 1510, 1350 using separate raising/lowering mechanisms. Furthermore, the flow cell cover 1510 is not limited to the case where it is raised/lowered by the raising/lowering mechanism 1300. For example, it is also possible to place the flow cell cover 1510, by hand, on the micro-channel chip 1730 that is stacked on the piezoelectric sensor 1700 moved to the connecting position, and to operate, after that, the raising/lowering mechanism 1300 to move the spring plungers 1350 to the pressing position.

Besides, the pressing part pressing the flow cell cover 1510 is not limited to the case where it is structured by the spring plungers 1350. For example, the pressing part may also have a structure in which the lower end portion of the spring member 1352 which is biased in an expansion direction and is in an exposed state without being housed in the plunger main body 1351, is abutted on the flow cell cover 1510. Further, it is also possible to design such that, by utilizing cushion pieces formed of elastic bodies made of rubber, sponge or the like, the flow cell cover 1510 is pressed within a range in which a spring constant of these cushion pieces becomes substantially constant.

Further, the sensing device 1100 according to the present embodiment provides the following effects. The flow cell base 1600 holding the piezoelectric sensor 1700 is mounted to the arm members 1212 with an allowance with which it can move in the longitudinal direction, and when the arm members 1212 are moved in the horizontal direction to mount the piezoelectric sensor 1700 to the chassis part 1410, the flow cell base 1600 is guided toward the chassis part 1410 in a state of being placed on the guide member 1420. At this time, the flow cell base 1600 keeps a state of being pressed against the guide member 1420 because of its own weight, so that the piezoelectric sensor 1700 can be mounted to the chassis part 1410 without inclining in an unnecessary direction. As a result of this, when compared with a case where the piezoelectric sensor 1700 is mounted by hand or the like, for example, it is possible to achieve a correct sensing result by suppressing an occurrence of mounting failure such that the piezoelectric sensor 1700 floats or inclines because of the application of force in an unnecessary direction.

Here, in the aforementioned embodiment, although the pinion-rack mechanism (the pinion member 1231, the rack gear 1213) is used as the moving mechanism 1200 for moving the flow cell base 1600, the mechanism for moving the flow cell base 1600 is not limited to this example, and it is also possible to move the flow cell base 1600 by using a cylinder mechanism, a ball screw mechanism or the like. Further, regarding the raising/lowering mechanism 1300 for raising/lowering the flow cell cover 1510 as well, the mechanism is not limited to the case of using the crank mechanism (the arm members 1321, the crankshafts 1332 and the support members 1331), and it is of course possible to use a cylinder mechanism and other mechanisms.

Figure 33A:
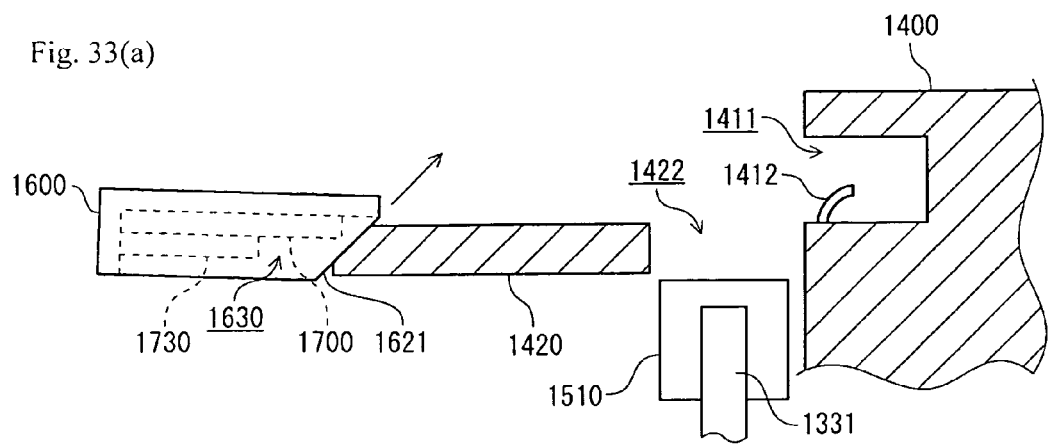
FIGS. 33(a), 33(b) and 33(c) are explanatory diagrams showing an another example of the sensing device.
Figure 33B:
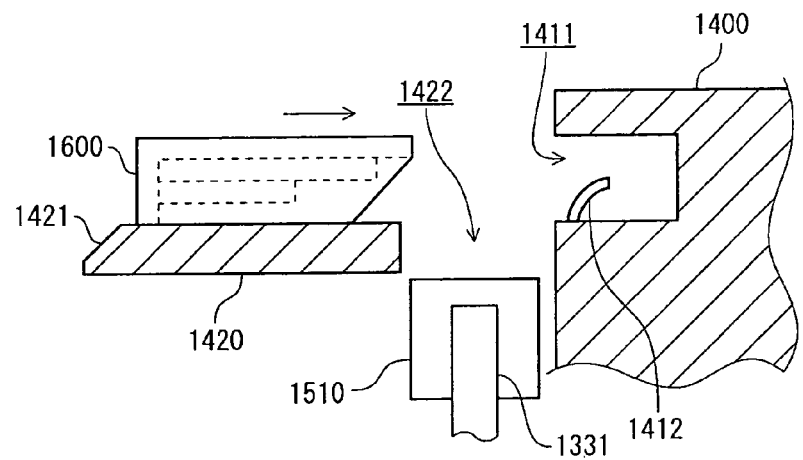
Figure 33C:
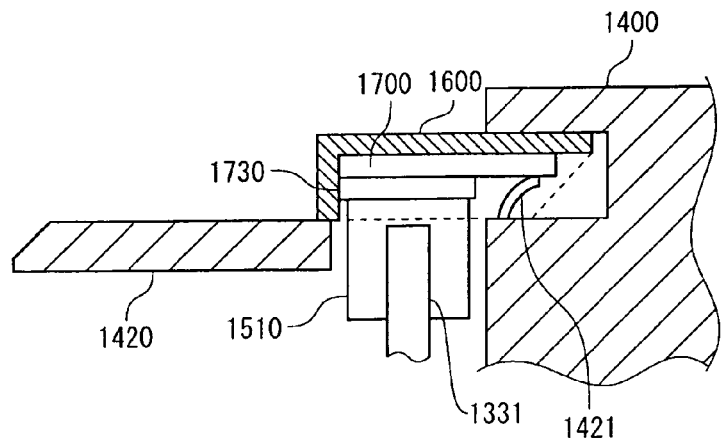
Figure 34:
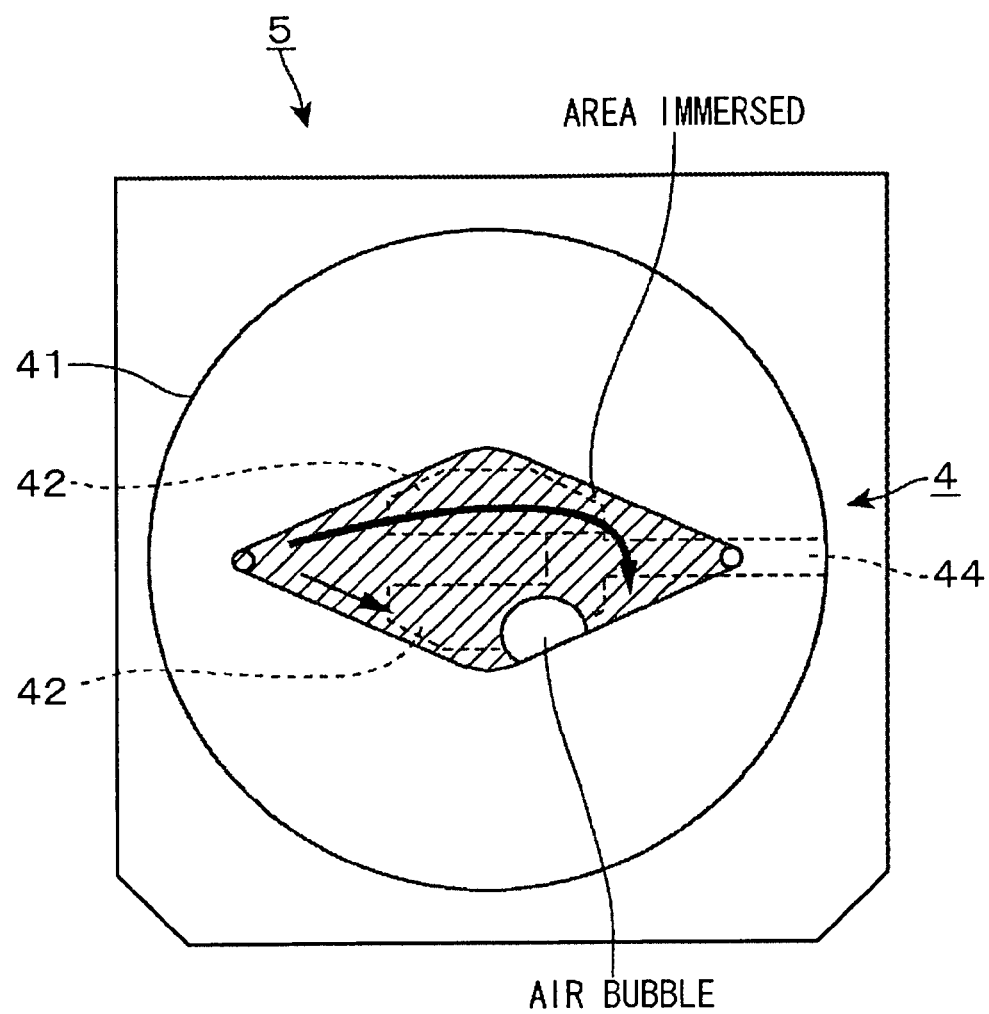
FIG. 34 is a plan view for explaining a state where a sample solution is inflowed through a sensor unit including a channel forming member with no groove portion.

Further, in the aforementioned sensing device 1100 explained using FIG. 13 to FIG. 32, explanation was made on the case where the flow cell base 1600 holds the piezoelectric sensor 1700 in a state where the quartz-crystal resonator 1720 is faced toward the upper surface side, and is moved on the guide member 1420 toward the connecting position, but, the flow cell base may also hold the piezoelectric sensor 1700 in a state where the quartz-crystal resonator 1720 is faced toward the lower surface side. In such a case, as shown in FIG. 33(*a*) to FIG. 33(*c*), for example, the concave portion 1630 capable of housing the entire piezoelectric sensor 1700 and micro-channel chip 1730 and opening to the lower surface side, is formed on the flow cell base 1600, and the piezoelectric sensor 1700 and the micro-channel chip 1730 are held in the concave portion 1630 while making the absorption surface of the quartz-crystal resonator 1720 face toward the lower surface side. Also in the present example, although the flow cell base 1600 is mounted to the movable body such as the arm members 1212 provided to the moving mechanism 1200 with an allowance with which it can move in the longitudinal direction, the description of the arm members 1212 is omitted in the respective drawings in FIG. 33(*a*) to FIG. 33(*c*).

At this time, the piezoelectric sensor 1700 and the micro-channel chip 1730 are locked by a not-shown locking member so that they do not fall from the flow cell base 1600, and further, the entire piezoelectric sensor 1700 and micro-channel chip 1730 is housed in the concave portion 1630, which prevents the lower surface of the micro-channel chip 1730 from being brought into contact with the upper surface of the guide member 1420 when the flow cell base 1600 is made to travel on the guide member 1420. Further, the surface to be guided 1621 of the flow cell base 1600 which is guided by the guide surface 1421 of the guide member 1420 is formed on the side surface on the front side of the flow cell base 1600. As a result of this, as shown in FIG. 33(*a*), FIG. 33(*b*), the flow cell base 1600 runs upon the guide member 1420 by being guided by the guide surface 1421, and then moves on the guide member 1420 toward the connecting position in a state of being placed on the upper surface of the guide member 1420.

Further, when the flow cell base 1600 reaches the connecting position and the piezoelectric sensor 1700 is connected to the connection port 1411 of the chassis part 1410, the flow cell cover 1510 retreated at the retreat position on the lower side of the guide member 1420 is raised to the upper surface side of the guide member 1420 through an access hole provided to the guide member 1420. As above, when the flow cell cover 1510 reaches the fixing position, the micro-channel chip 1730 is fixed by being pressed against the plate surface of the piezoelectric sensor 1700. Also in this case, by supplying the sample fluid to the passage space formed between the piezoelectric sensor 1700 and the micro-channel chip 1730, the sensing of substance to be sensed can be performed.

In addition, the sensing device 1100 which does not include the flow cell cover 1510 and the raising/lowering mechanism 1300 thereof is also included in the technical scope of the present invention. For instance, it is also possible that the flow cell base 1600 is structured in a shape of container to which the supply pipe 1131, the discharge pipe 1132 are connected, and the flow cell base 1600 is moved from the holding position to the connecting position in a state where the piezoelectric sensor 1700 is housed in the flow cell base 1600. In this case, by structuring the flow cell base 1600 so that the passage space is formed between the flow cell base 1600 and the piezoelectric sensor 1700, it becomes possible to form the passage space without using the micro-channel chip 1730 or the rubber packing 1730*a*.

Further, the structure such that the guide surface 1421 is provided at the tip portion of the guide member 1420, the surface to be guided 1621 is provided at the rear end portion of the flow cell base 1600, and when the flow cell base 1600 is moved from the holding position set on the near side of the guide member 1420 to the connecting position, the flow cell base 1600 is made to run upon the guide member 1420 in a manner that the guide surface 1421 on the guide member 1420 side guides the surface to be guided 1621, is not essential. For example, it is also possible to design such that the holding position is set on the guide member 1420, the flow cell base 1600 is made to hold the piezoelectric sensor 1700 in a state where the flow cell base 1600 is placed on the guide member 1420, and the movement of the flow cell base is started from that position toward the connecting position.

Furthermore, in the present invention, the guide member 1420 may also have an inclination gradually decreasing from the near side to the far side, for example, and on the contrary, it may also have an inclination gradually increasing in the same direction. It is possible to achieve the effect of the present invention as long as there is provided a structure in which the holding member 1600 mounted to the moving mechanism 1200 with an allowance with which it can move in the longitudinal direction is guided in the horizontal direction toward the connecting part (the terminal portion 1412, in the present example) while being pressed on the guide member 1420 side because of its own weight.

Further, the piezoelectric sensor 1700 capable of being adopted to the present sensing device 1100 is not limited to the aforementioned examples, and, for instance, the number of oscillation areas 1701a, 1701b provided to the quartz-crystal resonator 1720 is not limited to the example of two, and it may also be one or three or more. In this case, the sensing device 1100 preferably includes the oscillator circuit portions 1810a, 1810b in accordance with the number of oscillation areas, but, it is also possible that a plurality of oscillation areas share one oscillator circuit. Further, it is also possible to structure the piezoelectric resonator using a piezoelectric material other than the quartz-crystal, and the shape of the piezoelectric sensor 1700, the flow cell base 1600, the channel forming member (the micro-channel chip 1730 or the rubber packing 1730a) and the flow cell cover 1510 can also be appropriately changed according to need.

Besides, the sample fluid supplied to the passage space is not limited to liquid, and it may also be gas as a matter of course.

What is claimed is:

1. A sensing device that senses a substance to be sensed in a sample solution by using a piezoelectric sensor having a common piezoelectric piece on which a piezoelectric resonator is formed by providing two pairs of excitation electrodes arranged in an X direction to form a first oscillation area and a second oscillation area, in which an absorption layer absorbing the substance to be sensed in the sample solution is formed on the first oscillation area of the excitation electrodes on one surface side of the piezoelectric piece, and the absorption layer is not formed on the second oscillation area on said one surface side, the sensing device comprising:
    a channel forming member being contacted on said one surface side of the piezoelectric sensor, having an opposing surface opposing said one surface side having the first oscillation area and the second oscillation area via a gap, and forming a reaction channel which is a height of 0.3 mm or less on an area facing said one surface side;
    a liquid supply port being provided on one end side in a Y direction orthogonal to the X direction in the reaction channel and supplying the sample solution to the reaction channel;
    a liquid discharge port being provided on another end side in the Y direction in the reaction channel and discharging the sample solution from the reaction channel; and
    a groove part formed by stretching out along a flow direction of a liquid flow in the reaction channel on the opposing surface to control a liquid flow that suppresses a concentration of liquid flow caused because the first oscillation area has a hydrophilic property and the second oscillation area has a hydrophobic property due to the presence/absence of the absorption layer,
    wherein the first oscillation area and the second oscillation area are provided to sense, when the piezoelectric sensor is oscillated by oscillator circuits, the substance to be sensed based on oscillation frequencies of these oscillation areas.

2. The sensing device according to claim 1, wherein said groove part has a first groove portion extending from said liquid discharge port side toward the first oscillation area, and a second groove portion extending from said liquid discharge port side toward the second oscillation area, in which end portions on the sides of the oscillation areas of the first groove portion and the second groove portion are respectively positioned not to overlap with the first oscillation area and the second oscillation area.

3. The sensing device according to claim 2, wherein the first groove portion and the second groove portion are formed to have a distance therebetween gradually increasing toward the sides of the oscillation areas from said liquid discharge port, when seen from above.

4. The sensing device according to claim 3, wherein:
    the first groove portion is on a side of a line connecting said liquid supply port and said liquid discharge port, from an edge of the reaction channel extending from said liquid discharge port to the first oscillation area side; and
    the second groove portion is on a side of a line, from an edge of the reaction channel extending from said liquid discharge port to the second oscillation area side.

5. A sensing device that senses a substance to be sensed in a sample solution by using a piezoelectric sensor having a common piezoelectric piece on which a piezoelectric resonator is formed by providing two pairs of excitation electrodes arranged in an X direction to form a first oscillation area and a second oscillation area, in which an absorption layer absorbing the substance to be sensed in the sample solution is formed on the first oscillation area of the excitation electrodes on one surface side of the piezoelectric piece, and the absorption layer is not formed on the second oscillation area on said one surface side, the sensing device comprising:
    a channel forming member being contacted on said one surface side of the piezoelectric sensor, having an opposing surface opposing said one surface side having the first oscillation area and the second oscillation area via a gap, and forming a reaction channel on an area facing said one surface side;
    a liquid supply port being provided on one end side in a Y direction orthogonal to the X direction in the reaction channel and supplying the sample solution to the reaction channel;
    a liquid discharge port being provided on another end side in the Y direction in the reaction channel and discharging the sample solution from the reaction channel; and
    a groove part formed on the opposing surface to control a liquid flow that suppresses a concentration of liquid flow caused because the first oscillation area has a hydrophilic property and the second oscillation area has a hydrophobic property due to the presence/absence of the absorption layer;
    wherein the first oscillation area and the second oscillation area are provided to sense, when the piezoelectric sensor is oscillated by oscillator circuits, the substance to be sensed based on oscillation frequencies of these oscillation areas; and
    wherein said groove part has a first groove portion extending from said liquid discharge port side toward the first oscillation area, and a second groove portion extending from said liquid discharge port side toward the second oscillation area, in which end portions on the sides of the oscillation areas of the first groove portion and the second groove portion are respectively positioned not to overlap with the first oscillation area and the second oscillation area.

6. The sensing device according to claim 5, wherein the first groove portion and the second groove portion are formed to have a distance therebetween gradually increasing toward the sides of the oscillation areas from said liquid discharge port, when seen from above.

7. The sensing device according to claim 6, wherein:
the first groove portion is on a side of a line connecting said liquid supply port and said liquid discharge port, from an edge of the reaction channel extending from said liquid discharge port to the first oscillation area side; and
the second groove portion is on a side of a line, from an edge of the reaction channel extending from said liquid discharge port to the second oscillation area side.

* * * * *